(12) United States Patent
McAnulty et al.

(10) Patent No.: US 8,709,393 B2
(45) Date of Patent: Apr. 29, 2014

(54) METHODS AND COMPOSITIONS FOR WOUND HEALING

(75) Inventors: Jonathan F. McAnulty, Oregon, WI (US); Christopher Murphy, Davis, CA (US); Nicholas Abbott, Madison, WI (US)

(73) Assignee: Wound Engineering LLC, Oregon, WI (US)

( * ) Notice: Subject to any disclaimer, the term of this patent is extended or adjusted under 35 U.S.C. 154(b) by 601 days.

(21) Appl. No.: 12/363,044

(22) Filed: Jan. 30, 2009

(65) Prior Publication Data

US 2009/0263468 A1    Oct. 22, 2009

Related U.S. Application Data

(60) Provisional application No. 61/024,725, filed on Jan. 30, 2008.

(51) Int. Cl.
  *A61K 31/785* (2006.01)
  *A61K 9/00* (2006.01)

(52) U.S. Cl.
  USPC ............ 424/78.06; 424/400; 424/78.05

(58) Field of Classification Search
  CPC . A61L 26/00; A61L 26/0009; A61L 26/0019; A61K 9/0014; A61Q 19/00; A61Q 90/00
  USPC .................... 424/400, 78.08, 78.05
  See application file for complete search history.

(56) References Cited

U.S. PATENT DOCUMENTS

| | | | |
|---|---|---|---|
| 5,660,692 A * | 8/1997 | Nesburn et al. | 204/157.68 |
| 5,861,149 A * | 1/1999 | Ritter | 424/78.06 |
| 5,885,960 A * | 3/1999 | Nies | 514/9.1 |
| 6,095,148 A * | 8/2000 | Shastri et al. | 128/898 |
| 6,559,119 B1 * | 5/2003 | Burgess et al. | 514/2.3 |
| 6,696,077 B2 | 2/2004 | Scherr | |
| 6,716,452 B1 * | 4/2004 | Piccariello et al. | 424/457 |
| 6,855,860 B2 | 2/2005 | Ruszczak et al. | |
| 7,045,146 B2 | 5/2006 | Caruso et al. | |
| 7,118,761 B2 | 10/2006 | Canada et al. | |
| 7,595,355 B2 | 9/2009 | Trogolo | |
| 2003/0143335 A1 | 7/2003 | Qiu et al. | |
| 2003/0157260 A1 | 8/2003 | Rubner et al. | |
| 2004/0149572 A1 * | 8/2004 | Schlenoff et al. | 204/296 |
| 2005/0249791 A1 | 11/2005 | Hobbs et al. | |
| 2005/0249818 A1 * | 11/2005 | Sawan et al. | 424/618 |
| 2006/0172956 A1 * | 8/2006 | Bonner et al. | 514/35 |
| 2007/0129792 A1 | 6/2007 | Picart et al. | |
| 2007/0154448 A1 | 7/2007 | Reid et al. | |
| 2008/0131493 A1 | 6/2008 | Matloub | |
| 2009/0263468 A1 | 10/2009 | McAnulty | |

FOREIGN PATENT DOCUMENTS

| | | |
|---|---|---|
| WO | 01/64258 | 9/2001 |
| WO | WO 2005/025548 A1 | 3/2005 |
| WO | WO 2007035296 A2 * | 3/2007 |

OTHER PUBLICATIONS

Elbert et al., Langmuir, 1999, 15, 5355-5362.*
Thompson et al., Biomaterials, 2005, 26, 6386-6845.*
Agarwal, A., et al., "Surfaces modified with nanometer-thick silver-impregnated polymeric films that kill bacteria but support growth of mammalian cells," Biomaterials, Feb. 2010. (online published on Oct. 28, 2009), vol. 31, No. 4, pp. 680-690.
Huang, et al., "Chitosan mediated assembly of gold nanoparticles multilayer," Colloids and Surfaces A: Physicochem. Eng. Aspects 226 (2003) pp. 77-86.
Wang, Tom C., et al., "Polyelectrolyte Multilayer Nanoreactors for Preparing Silver Nanoparticle Composites: Controlling Metal Concentration and Nanoparticle Size," Langmuir, vol. 18, No. 8, Apr. 1, 2002, pp. 3370-3375.
Lee, Daeyeon, et al., "Antibacterial properties of Ag nanoparticle loaded multilayers and formation of magnetically directed antibacterial microparticles," Langmuir, American Chemical Society, New York, NY US, vol. 21, No. 21, Oct. 11, 2005, pp. 9651-9659.
Atiyeh, et al., "Effect of silver on burn wound infection control and healing: Review of the Literature," Burns, Butterworth Heinemann, GB, vol. 33, No. 2, Feb. 3, 2007, pp. 139-148.
EP Supplemental Search mailed Feb. 26, 2013, EP Patent Application No. 09 748 927.2.

* cited by examiner

Primary Examiner — Abigail Fisher
(74) Attorney, Agent, or Firm — Casimir Jones, S.C.

(57) ABSTRACT

The present invention relates to methods and compositions for wound healing. In particular, the present invention relates to promoting and enhancing wound healing by utilizing cross-linker covalent modification molecules to attach and deliver wound active agents to a wound. In addition, the present invention provides methods and compositions utilizing oppositely charged polymers to form a polyelectrolyte layer on a wound surface. The invention further relates to incorporating wound active agents into a polyelectrolyte layer for delivery to a wound.

4 Claims, 22 Drawing Sheets

FIGURE 7

ID: AAP_BOMMA
DE: ANIONIC ANTIMICROBIAL PEPTIDE.

ID: ABAE_APIME
DE: ABAECIN PRECURSOR; INSECT DEFENCE PEPTIDE

ID: ABAE_BOMPA
DE: ABAECIN; INSECT DEFENCE PEPTIDE.

ID: ABAS_BASAL
DE: ALPHA-BASRUBRIN (FRAGMENT).

ID: ABF1_CAEEL
DE: ABF-1, ANTIBACTERIAL FACTOR PRECURSOR; NEMATODE DEFENSIN, INSECT DEFENSIN-LIKE

ID: ABF2_CAEEL
DE: ABF-2, ANTIBACTERIAL FACTOR PRECURSOR; NEMATODE DEFENSIN, INSECT DEFENSIN-LIKE

ID: ABF5_CAEEL
DE: ABF-5, ANTIBACTERIAL FACTOR PRECURSOR; NEMATODE DEFENCE PEPTIDE

ID: ABF6_CAEEL
DE: ABF-6, ANTIBACTERIAL FACTOR PRECURSOR; NEMATODE DEFENCE PEPTIDE

ID: ABP2_RIPCL
DE: ANTIBACTERIAL PEPTIDE PRECURSOR (PUTATIVE); INSECT DEFENCE PEPTIDE.

ID: ABPP_RIPCL
DE: ANTIBACTERIAL PEPTIDE PRECURSOR (PUTATIVE); INSECT DEFENCE PEPTIDE

ID: ACA1_ACALU
DE: ACALOLEPTIN A1; INSECT DEFENCE PEPTIDE; COLEPTERICIN

ID: ACAN_ACAGO
DE: ACANTHOSCURRIN PRECURSOR.

ID: ACHC_ACHFU
DE: ACHACIN PRECURSOR; GASTROPOD DEFENCE PROTEIN.

ID: AFP2_GASEL
DE: ANTIFUNGAL PROTEIN.

ID: AFP3_BRANA
DE: CYSTEIN-RICH ANTIFUNGAL PEPTIDE PRECURSOR; PLANT DEFENSIN

ID: AFP_ASPGI

DE: MOULD ANTIFUNGAL PEPTIDE PRECURSOR

ID: AFP_GASEL
DE: ANTIFUNGAL PROTEIN.

ID: ALO1_ACRLO
DE: ANTIMICROBIAL PEPTIDE ALO-1.

ID: ALO2_ACRLO
DE: ANTIMICROBIAL PEPTIDE ALO-1.

ID: ALO3_ACRLO
DE: ANTIMICROBIAL PEPTIDE ALO-1.

ID: ALPS_LIMPO
DE: ANTI-LIPOPOLYSACCHARIDE (LPS) FACTOR.

ID: ALPS_TACTR
DE: ANTI-LIPOPOLYSACCHARIDE (LPS) FACTOR.

ID: AMP1_ALLCE
DE: ANTIMICROBIAL PROTEIN ACE-AMP1 PRECURSOR; PLANT DEFENCE PEPTIDE

ID: AMP1_MACIN
DE: ANTIMICROBIAL PEPTIDE 1 PRECURSOR (AMP1); PLANT DEFENCE PEPTIDE;

ID: AMP1_MESCR
DE: ANTIMICROBIAL PEPTIDE 1 PRECURSOR, PLANT DEFENCE PEPTIDE;

ID: AMP1_MIRJA
DE: ANTIMICROBIAL PEPTIDE 1 (AMP1); PLANT DEFENCE PEPTIDE

ID: AMP2_MIRJA
DE: ANTIMICROBIAL PEPTIDE 2 (AMP2); PLANT DEFENCE PEPTIDE
ID: AMP_AMACA
DE: ANTIMICROBIAL PEPTIDE (AMP1 AND AMP2); PLANT DEFENCE PEPTIDE.

ID: AMP_AMAHY
DE: ANTIMICROBIAL PROTEIN PRECURSOR. PLANT DEFENSE PEPTIDE

ID: AMP_CARMA
DE: CARCININ, 11 KDA ATIMICROBIAL PROTEIN; CRUSTACEAN DEFENSE PROTEIN

ID: AMSH_BOVIN
DE: MELANOTROPIN ALPHA (ALPHA-MSH)

ID: ANDP_DROME

DE: ANDROPIN PRECURSOR. INSECT DEFENCE PEPTIDE.

ID: ANDP_DROOR
DE: ANDROPIN PRECURSOR. INSECT DEFENCE PEPTIDE.

ID: ANDP_DROSE
DE: ANDROPIN PRECURSOR. INSECT DEFENCE PEPTIDE

ID: ANDP_DROSI
DE: ANDROPIN PRECURSOR, INSECT DEFENCE PEPTIDE.

ID: ANDP_DROTE
DE: ANDROPIN PRECURSOR, INSECT DEFENCE PEPTIDE.

ID: ANDP_DROYA
DE: ANDROPIN PRECURSOR, INSECT DEFENCE PEPTIDE.

ID: ANDT_ANDAU
DE: ANDROCTONIN; CHELICERATE DEFENCE PEPTIDE

ID: ANPL_ANOSA
DE: ANOPLIN

ID: ANSA_STRCZ
DE: ANTIBACTERIAL SUBSTANCE A.

ID: ANTF_SARPE
DE: ANTIFUNGAL PROTEIN PRECURSOR (AFP). INSECT DEFENCE PEPTIDE
ID: AP14_APIME
DE: APIDAECIN PRECURSOR. TYPE 14. INSECT DEFENCE PEPTIDE

ID: AP22_APIME
DE: APIDAECIN PRECURSOR. TYPE 22. INSECT DEFENCE PEPTIDE

ID: AP39_PIG
DE: ANTIBACTERIAL PEPTIDE 3910. MAMMALIAN DEFENCE PEPTIDE

ID: AP73_APIME
DE: INSECT ANTIMICROBIAL PEPTIDE

ID: APA2_BOVIN
DE: APOLIPOPROTEIN A-II (APO-AII) (ANTIMICROBIAL PEPTIDE BAMP-1).

ID: API2_APIME
DE: APIDAECIN II. INSECT DEFENCE PEPTIDE

ID: APIA_APIME
DE: PRO-APIDAECIN IA. INSECT DEFENCE PEPTIDE

ID: APIB_APIME

FIGURE 7 (cont.)

DE: PRO-APIDAECIN IB. INSECT DEFENCE PEPTIDE

ID: API_BOMPA
DE: APIDAECIN, INSECT DEFENCE PEPTIDE

ID: APLY_APLKU
DE: APLYSIANIN-A PRECURSOR. GASTROPOD DEFENCE PROTEIN.

ID: APRFR_BOVIN
DE: APROTININ ANTIBACTERIAL FRAGMENTS

ID: ARIN_CICAR
DE: ARIETIN (FRAGMENT); PLANT DEFENCE PEPTIDE.

ID: ASABF_ASCSU
DE: AS ANTIBACTERIAL FACTOR PRECURSOR; NEMATODE DEFENSIN, INSECT DEFENSIN-LIKE

ID: ASCP2_ASCTR
DE: ASCAPHIN-1, -2. AND 3. FROG DEFENCE PEPTIDES

ID: ASCP4_ASCTR
DE: ASCAPHIN-4, -5, -6 AND 7. FROG DEFENCE PEPTIDES

ID: ASCP8_ASCTR
DE: ASCAPHIN-8, FROG DEFENCE PEPTIDES

ID: ATT1_DROME
DE: ATTACIN B1 PRECURSOR.

ID: ATTA_DROME
DE: ATTACIN A PRECURSOR.

ID: ATTA_GLOMO
DE: ANTIMICROBIAL PEPTIDE ATTACIN ATTA, INSECT DEFENCE PROTEIN

ID: ATTA_TRINI
DE: ATTACIN A PRECURSOR. INSECT DEFENCE PROTEIN

ID: ATTB_HYACE
DE: PROATTACIN B PRECURSOR (IMMUNE PROTEIN P5); INSECT DEFENCE PROTEIN

ID: ATTE_HYACE
DE: ATTACIN E AND F (IMMUNE PROTEIN P5). INSECT DEFENCE PROTEINS

ID: ATT_BOMMO
DE: ATTACIN PRECURSOR. INSECT DEFENCE PROTEIN

ID: BAB1B_MAIZE
DE: BASAL LAYER ANTIFUNGAL PEPTIDE PRECURSOR..

ID: BAP1A_MAIZE
DE: BASAL LAYER ANTIFUNGAL PEPTIDE PRECURSOR.

ID: BAP3A_MAIZE
DE: BASAL LAYER ANTIFUNGAL PEPTIDE PRECURSOR.

ID: BAP3B_MAIZE
DE: BASAL LAYER ANTIFUNGAL PEPTIDE PRECURSOR.

ID: BCT1PRC_BOVIN
DE: CYCLIC DODECAPEPTIDE PRECURSOR (BCT1)(CATHELICIDIN)
ID: BCT1PRC_SHEEP
DE: CYCLIC DODECAPEPTIDE PRECURSOR (BCT1)(CATHELICIDIN).

ID: BCT1_BOVIN
DE: CYCLIC DODECAPEPTIDE

ID: BCT1_SHEEP
DE: SHEEP CYCLIC DODECAPEPTIDE .

ID: BCT5PRC_BOVIN
DE: BACTENECIN 5 (BAC5) PRECURSOR(CATHELICIDIN).

ID: BCT5PRC_CAPHI
DE: BACTENECIN 5 PRECURSOR (CHBAC5)(CATHELICIDIN).

ID: BCT5PRC_SHEEP
DE: BACTENECIN 5 PRECURSOR (BAC5)(CATHELICIDIN).

ID: BCT5_BOVIN
DE: BACTENECIN 5, BAC5.

ID: BCT6PRC_SHEEP
DE: BACTINECIN 6 PRECURSOR (CATHELICIDIN)

ID: BCT7PRC_BOVIN
DE: BACTENECIN 7 (BAC7) PRECURSOR (CATHELICIDIN).

ID: BCT7PRC_SHEEPDE:
BACTENECIN 7.5 (BAC7.5) PRECURSOR (CATHELICIDIN).

ID: BCT7_BOVINDE: BACTENECIN 7, BAC7.

ID: BCT7_CARMADE:
CRUSTACEAN BACTENECIN (FRAGMENT)

ID: BCT7_SHEEPDE: SHEEP BACTENECIN, BAC7.5.

ID: BD01A_CHICK

DE: GALLINACIN 1 ALPHA, AVIAN BETA-DEFENSIN

ID: BD01B_PREOB
DE: DEFB1-LIKE PROTEIN.

ID: BD01P_MOUSE
DE: PROSTATE BETA-DEFENSIN 1.

ID: BD01_APTPA
DE: SPHENISCIN 1 (SPHE-1) (PBD-1)(AVIAN BETA-DEFENSIN).

ID: BD01_BOVIN
DE: BOVINE BETA-DEFENSIN 1 (BNDB-1).

ID: BD01_CAPHI
DE: BETA-DEFENSIN 1 PRECURSOR (BD-1).

ID: BD01_CERAE
DE: CERCOPITHECUS AETHIOPS CERCOPITHECUS BETA-DEFENSIN 1 (CAEBD-1).

ID: BD01_CERER
DE: CERCOPITHECUS ERYTHROGASTER BETA-DEFENSIN 1 (CERBD-1).

ID: BD01_CERPR
DE: CERCOPITHECUS PREUSSI BETA-DEFENSIN 1 (CPRBD-1).

ID: BD01_CHICK
DE: GALLINACIN 1, AVIAN BETA-DEFENSIN.

ID: BD01_CHILA

ID: BD01_DOG
DE: BETA-DEFENSIN-LIKE PEPTIDE 1 [CANIS

ID: BD01_EQUCA
DE: HORSE BETA-DEFENSIN 1

ID: BD01_GORGO
DE: GORILLA GORILLA BETA-DEFENSIN 1 (GGOBD-1).

ID: BD01_HUMAN
DE: HUMAN BETA-DEFENSIN 1 (HBD-1).

ID: BD01_HYLCO

ID: BD01_HYLLA
DE: HYLOBATES LAR BETA-DEFENSIN 1 (HLARBD-1).

ID: BD01_HYLMO
DE: HYLOBATES MOLOCH BETA-DEFENSIN 1 (HMOLBD-1).

ID: BD01_MACFA

FIGURE 7 (cont.)

DE: MACACA FASCICULARIS
BETA-DEFENSIN 1 (MFABD-1).

ID: BD01_MACMU
DE: BETA-DEFENSIN 1 PRECURSOR
(RHBD-1) (DEFENSIN, BETA 1).

ID: BD01_MELGA
DE: ANTIMICROBIAL PEPTIDE 1
(AMP1); THP1 (TURKEY
HETEROPHIL PEPTIDE 1), BETA-
DEFENSIN.

ID: BD01_MOUSEDE: BETA-
DEFENSIN 1 HOMOLOG
PRECURSOR (BD).

ID: BD01_PANTR
DE: BETA-DEFENSIN 1.

ID: BD01_PAPAN
DE: PAPIO ANUBIS BETA-
DEFENSIN 1 (PAPBD-1).

ID: BD01_PIG
DE: BETA-DEFENSIN 1 PRECURSOR
(RHBD-1) (DEFENSIN, BETA 1).

ID: BD01_PONPY
DE: PONGO PYGMAEUS BETA-
DEFENSIN 1 (PPYBD-1).

ID: BD01_PRECR
DE: PRESBYTIS CRISTATA BETA-
DEFENSIN 1 (PCRBD-1).

ID: BD01_PREMEDE:
PRESBYTIS MELALOPHOS BETA-
DEFENSIN 1 (PMEBD-1).

ID: BD01_PREOBDE: PRESBYTIS
OBSCURUS BETA-DEFENSIN 1
(POBBD-1).

ID: BD01_RAT
DE: BETA-DEFENSIN 1 PRECURSOR
(BD-1).

ID: BD01_SAGOE
DE: SAGUINUS OEDIPUS BETA-
DEFENSIN 1 (SOEBD-1).

ID: BD01_SHEEP
DE: BETA-DEFENSIN 1
PRECURSOR.

ID: BD02A_MACMU
DE: CERCOPITHECIDAE/MACACA
BETA-DEFENSIN 2.

ID: BD02B_MACMU
DE: BETA-DEFENSIN 2.

ID: BD02_APTPA
DE: SPHENISCIN 1 (SPHE-1) (PBD-
1)(AVIAN BETA-DEFENSIN).

ID: BD02_BOVIN
DE: BOVINE BETA-DEFENSIN 2
(BNDB-2).

ID: BD02_CAPHI
DE: BETA-DEFENSIN 2
PRECURSOR.

ID: BD02_CERPR
DE: CERCOPITHECUS BETA-
DEFENSIN 2.

ID: BD02_CHICK
DE: GALLINACIN 2, AVIAN BETA-
DEFENSIN.

ID: BD02_GORGO
DE: GORILLA BETA-DEFENSIN

ID: BD02_HUMAN
DE: BETA-DEFENSIN 2 PRECURSOR
(HBD-2)(DEFB2)(SKIN-
ANTIMICROBIAL PEPTIDE
1)(SAP1).

ID: BD02_HYLLA
DE: HYLOBATES BETA-DEFENSIN
2

ID: BD02_MELGA
DE: ANTIMICROBIAL PEPTIDE 2
(AMP2), THP2 (TURKEY
HETEROPHIL PEPTIDE 2)
(FRAGMENT), BETA-DEFENSIN.

ID: BD02_MOUSE
DE: BETA-DEFENSIN 2
PRECURSOR.

ID: BD02_PANTR
DE: CHIMPANZEE BETA-DEFENSIN
2

ID: BD02_PONPY
DE: PONGO PYGMAEUS BETA-
DEFENSIN 2 (PPYBD-2).

ID: BD02_PREME
DE: PRESBYTIS BETA-DEFENSIN 2.

ID: BD02_RAT
DE: BETA-DEFENSIN 2
PRECURSOR; RBD-2.

ID: BD02_SHEEP
DE: BETA-DEFENSIN 2
PRECURSOR.

ID: BD03_BOVIN
DE: BOVINE BETA-DEFENSIN 3
(BNDB-3).

ID: BD03_CERPR
DE: BETA-DEFENSIN-3 HUMAN
AND NON HUMAN PRIMATES.

ID: BD03_CHICK
DE: GALLINACIN 3, AVIAN BETA-
DEFENSIN.

ID: BD03_GORGO
DE: BETA-DEFENSIN-3 HUMAN
AND NON HUMAN PRIMATES.

ID: BD03_HUMAN
DE: BETA-DEFENSIN-3.

ID: BD03_HYLCO
DE: BETA-DEFENSIN-3 HUMAN
AND NON HUMAN PRIMATES.

ID: BD03_HYLLA
DE: BETA-DEFENSIN-3 HUMAN
AND NON HUMAN PRIMATES.

ID: BD03_MACFA
DE: BETA-DEFENSIN-3 HUMAN
AND NON HUMAN PRIMATES.

ID: BD03_MELGA
DE: ANTIMICROBIAL PEPTIDE 3
(AMP3) THP3 (TURKEY
HETEROPHIL PEPTIDE 3), BETA-
DEFENSIN (FRAGMENT).

ID: BD03_MOUSE
DE: BETA-DEFENSIN 3 PRECURSOR
(BD-3).

ID: BD03_PANTR
DE: BETA-DEFENSIN-3.

ID: BD03_PAPAN
DE: BETA-DEFENSIN-3 HUMAN
AND NON HUMAN PRIMATES.

ID: BD03_PONPY
DE: BETA-DEFENSIN-3 HUMAN
AND NON HUMAN PRIMATES.

ID: BD03_PREOB
DE: BETA-DEFENSIN-3 HUMAN
AND NON HUMAN PRIMATES

ID: BD03_PRIMATE
DE: BETA-DEFENSIN-3 HUMAN
AND NON HUMAN PRIMATES.

ID: BD03_SAGOE
DE: BETA-DEFENSIN-3 HUMAN
AND NON HUMAN PRIMATES.

ID: BD04_BOVIN
DE: BOVINE BETA-DEFENSIN 4
(BNDB-4).

ID: BD04_HUMAN
DE: BETA-DEFENSIN 4 PRECURSOR
(BD-4) (HBD-4).

ID: BD04_MELGA
DE: GALLOPAVIN 1, AVIAN BETA-
DEFENSIN.

ID: BD04_MOUSE
DE: BETA-DEFENSIN 4 PRECURSOR
(MBD-4).

ID: BD05_BOVIN
DE: BOVINE BETA-DEFENSIN 5
(BNDB-5).

FIGURE 7 (cont.)

ID: BD05_MOUSE
DE: BETA-DEFENSIN 5.

ID: BD06_BOVIN
DE: BOVINE BETA-DEFENSIN 6
(BNDB-6).

ID: BD06_MOUSE
DE: BETA-DEFENSIN 6.

ID: BD07_BOVIN
DE: BOVINE BETA-DEFENSIN 7
(BNDB-7).

ID: BD07_MOUSE
DE: BETA-DEFENSIN 7
PRECURSOR.

ID: BD08_BOVIN
DE: BOVINE BETA-DEFENSIN 8
(BNDB-8).

ID: BD08_MOUSE
DE: BETA-DEFENSIN 8 (BETA-
DEFENSIN 6).

ID: BD09_BOVIN
DE: BOVINE BETA-DEFENSIN 9
(BNDB-9).

ID: BD10_BOVIN
DE: BOVINE BETA-DEFENSIN 10
(BNDB-10).

ID: BD11_BOVIN
DE: BOVINE BETA-DEFENSIN 11
(BNDB-11).

ID: BD12_BOVIN
DE: BOVINE BETA-DEFENSIN 12
(BNDB-12).

ID: BD13_BOVIN
DE: BOVINE BETA-DEFENSIN 13
(BNDB-13).

ID: BD40_MOUSE
DE: MOUSE BETA DEFENSIN 40
PRECURSOR.

ID: BDC7_BOVIN
DE: BETA-DEFENSIN C7
PRECURSOR; BBD-C7
(FRAGMENT).

ID: BHP_BOVIN;
DE: BOVIN ALPHA HEMOGLOBIN
ANTIMICROBIAL FRAGMENT
FROM TICK GUT

ID: BIGDEF_LIMPO
DE: LIMULUS BIG DEFENSIN

ID: BIN1_RAT
DE: ANTI-MICROBIAL-LIKE
PROTEIN BIN-1B [RATTUS
NORVEGICUS].

ID: BLP1_BOMOR
DE: BOMBININ-LIKE PEPTIDE 1
PRECURSOR (BLP-1).

ID: BLP2_BOMOR
DE: BOMBININ-LIKE PEPTIDE 2
(BLP-2).

ID: BLP3_BOMOR
DE: BOMBININ-LIKE PEPTIDE 3
PRECURSOR (BLP-3).

ID: BLP4_BOMOR
DE: BOMBININ-LIKE PEPTIDE 4
(BLP-4).

ID: BLP_BOMVA
DE: BOMBININ-LIKE PEPTIDE
PRECURSOR (BLP).

ID: BMAP27PRC_BOVIN
DE: ANTIBACTERIAL PEPTIDE
BMAP-27 PRECURSOR;
CATHELICIDIN; MB 27 IN
SWISSPROT

ID: BMAP28PRC_BOVIN
DE: ANTIBACTERIAL PEPTIDE
BMAP-28 PRECURSOR;
CATHELICIDIN, MP28 IN
SWISSPROT

ID: BMAP34_BOVIN
DE: ANTIBACTERIAL PEPTIDE
BMAP-34 PRECURSOR, MB34.

ID: BMKBPP_BUTMA
DE: BMKBPP (PARABUTOPORIN).

ID: BNP32_HUMAN
DE: BRAIN NATRIURETIC PEPTIDE
(BNP-32).

ID: BOL1_MEGPE
DE: BOMBOLITIN I.

ID: BOL2_MEGPE
DE: BOMBOLITIN II.

ID: BOL3_MEGPE
DE: BOMBOLITIN III.

ID: BOL4_MEGPE
DE: BOMBOLITIN IV.

ID: BOL5_MEGPE
DE: BOMBOLITIN V.

ID: BOMH1_BOMVA
DE: BOMBININ H1.

ID: BOMH2_BOMVA
DE: BOMBININ H2

ID: BOMH3_BOMVA
DE: BOMBININ H3.

ID: BOMH4_BOMVA
DE: BOMBININ H4.

ID: BOMH5_BOMVA
DE: BOMBININ H5

ID: BOMN_BOMVA
DE: BOMBININ.

ID: BPI_BOVIN
DE: BOVINE BACTERICIDAL
PERMEABILITY-INCREASING
PROTEIN(BPI).

ID: BPI_HUMAN
DE: HUMAN BACTERICIDAL
PERMEABILITY INCREASING
PROTEIN PRECURSOR (BPI)
(CAP57).

ID: BPI_RABIT
DE: RABBIT BACTERICIDAL
PERMEABILITY-INCREASING
PROTEIN (BPI) (FRAGMENT).

ID: BPT1_BOVIN
DE: BACTERICIDAL FRAGMENTS
FROM BPTI, APROTININ

ID: BR1A_RANES
DE: BREVININ-1EA.

ID: BR1A_RANTE
DE: BREVININ-1TA.

ID: BR1BA_RANBE
DE: BREVININ-1BA.

ID: BR1BB_RANBE
DE: BREVININ-1BB.

ID: BR1BC_RANBE
DE: BREVININ-1BC.

ID: BR1BD_RANBE
DE: BREVININ-1BD.

ID: BR1BE_RANBE
DE: BREVININ-1BE.

ID: BR1BF_RANBE
DE: BREVININ-1BF.

ID: BR1BYA_RANBO
DE: BREVININ-1BYA, -1BYB AND -
1BYC.

ID: BR1B_RANES
DE: BREVININ-1EB.

ID: BR1EC_RANES
DE: BREVININ-1EC.

ID: BR1E_RANES
DE: BREVININ-1E PRECURSOR.

ID: BR1LA_RANLU
DE: BREVININ-1LA.

ID: BR1LB_RANLU

FIGURE 7 (cont.)

ID: BREVININ-1LB.

ID: BR1PB_RANPI
DE: BREVININ-1PB.

ID: BR1SC_RANSP
DE: BREVININ 1SC

ID: BR1S_RANSP
DE: BREVININ 1SA AND 1SB

ID: BR1TRA_RANTA
DE: BREVININ-1TRA.

ID: BR1T_RANTE
DE: BREVININ-1T.

ID: BR1_RANBP
DE: BREVININ-1.

ID: BR1_RANDA
DE: BREVININ-1 DA.

ID: BR20A_RANOR
DE: BREVININ-20A.

ID: BR20B_RANOR
DE: BREVININ-20B.

ID: BR2A_RANES
DE: BREVININ-2EA.

ID: BR2B_RANES
DE: BREVININ-2EB.

ID: BR2C_RANES
DE: BREVININ-2EC.

ID: BR2D_RANES
DE: BREVININ-2ED.

ID: BR2E_RANES
DE: BREVININ-2E.

ID: BR2F_RANES
DE: BREVININ-2EF PRECURSOR.

ID: BR2G_RANES
DE: BREVININ-2EG; AMPHIBIAN DEFENCE PEPTIDE

ID: BR2H_RANES
DE: BREVININ-2EH; AMPHIBIAN DEFENCE PEPTIDE

ID: BR2_RANBP
DE: BREVININ-2.

ID: BRE1E_RANES
DE: BREVININ-1E.

ID: BREE_RANES
DE: BREVININ-2EE.

ID: BRKM_BOMMA
DE: MAXIMAKININ [CONTAINS: BRADYKININ].

ID: BRTA_RANTE
DE: BREVININ-2TA PRECURSOR.

ID: BRTB_RANTE
DE: BREVININ-2TB PRECURSOR.

ID: BUTH_ANDAU
DE: BUTHININ; CHELICERATE DEFENCE PEPTIDE

ID: C18PRC_RABIT
DE: 18 KD LIPOPOLYSACCHARIDE-BINDING PROTEIN PRECURSOR (18 KD CATIONIC PROTEIN) (CAP18-A) (CATHELICIDIN).

ID: C18_RABIT
DE: CAP18

ID: CAE1_XENLA
DE: PREPROCAERULEIN TYPE I. (ANTIMICROBIAL CPF PRECURSOR)

ID: CAE2_XENLA
DE: PREPROCAERULEIN TYPE I (FRAGMENT). (ANTIMICROBIAL CPF PRECURSOR)

ID: CAE3_XENLA
DE: PREPROCAERULEIN TYPE III. (ANTIMICROBIAL CPF PRECURSOR)

ID: CAE4_XENBO
DE: PREPROCAERULEIN TYPE IV (ANTIMICROBIAL CPF PRECURSOR)

ID: CAE4_XENLA
DE: PREPROCAERULEIN TYPE IV. (ANTIMICROBIAL CPF PRECURSOR)

ID: CAE5_XENLA
DE: PREPROCAERULEIN (CLONE PXC202) (FRAGMENT) (ANTIMICROBIAL CPF PRECURSOR).

ID: CALN_UNKW
DE: CALLIVICIN.

ID: CALT_BOVIN
DE: CALTRIN (SEMINAL PLASMIN)PRECURSOR FRAGMENT).

ID: CAP7A_HUMAN
DE: FRAGMENT 20-44 OF CAP7-HUMAN.

ID: CAP7_HUMAN
DE: AZUROCIDIN PRECURSOR (CATIONIC ANTIMICROBIAL PROTEIN CAP37)(HEPARIN-BINDING PROTEIN) (HBP) (FRAGMENT).

ID: CAP7_PIG
DE: AZUROCIDIN (CATIONIC ANTIMICROBIAL PROTEIN CAP37) (HEPARIN-BINDING PROTEIN) (HBP).

ID: CASN1_BOVIN
DE: CASOCIDIN-I; ALPHA-S2 CASEIN FRAGMENT (165-203).

ID: CATG_HUMAN
DE: CATHEPSIN G PRECURSOR (EC 3.4.21.20).

ID: CATH29_MYXGL
DE: HEMATOPOIETIC ANTIMICROBIAL PEPTIDE-29 PRECURSOR (CATH29)(HFIAP)(FRAGMENT)(CATHELICIDIN)

ID: CATH37_MYXGL
DE: HEMATOPOIETIC ANTIMICROBIAL PEPTIDE-37 PRECURSOR (CATH37)(HFIAP)(CATHELICIDIN)

ID: CATH_DOG
DE: DOG CATHELICIDIN.

ID: CEC1_CERCA
DE: CECROPIN 1 PRECURSOR.

ID: CEC1_MUSDO
DE: CECROPIN 1.

ID: CEC1_PIG
DE: CECROPIN P1.

ID: CEC2_CERCA
DE: CECROPIN 2 PRECURSOR.

ID: CEC2_MANSE
DE: BACTERICIDIN B-2 (CECROPIN-LIKE PEPTIDE B-2).

ID: CEC3_MANSE
DE: BACTERICIDIN B-3 (CECROPIN-LIKE PEPTIDE B-3).

ID: CEC4_BOMMO
DE: CECROPIN (ANTIBACTERIAL PEPTIDE CM-IV).

ID: CEC4_MANSE
DE: BACTERICIDIN B-4 (CECROPIN-LIKE PEPTIDE B-4).

ID: CEC5_MANSE
DE: BACTERICIDIN B-5P PRECURSOR (CECROPIN-LIKE PEPTIDE B-5).

ID: CECA1_AEDAL
DE: ANTIBIOTIC PEPTIDE

ID: CECA1_DROSE
DE: CECROPIN A1 PRECURSOR.

ID: CECA1_HYPCU
DE: HYPHANCIN IIIE PRECURSOR, HYPHANTIA CECROPIN A1.

FIGURE 7 (cont.)

ID: CECA2_AEDAL
DE: ANTIBIOTIC PEPTIDE
CECROPIN A2.

ID: CECA2_HYPCU
DE: HYPHANCIN IIIF PRECURSOR,
HYPHANTIA CECROPIN A2

ID: CECA3_HYPCU
DE: HYPHANCIN IIIG PRECURSOR.
HYPHANTRIA CECROPIN A3

ID: CECA_AEDAE
DE: CECROPIN A

ID: CECA_AEDAL
DE: CECROPIN A (AALCECA).

ID: CECA_BOMMO
DE: CECROPIN A PRECURSOR.

ID: CECA_DROME
DE: CECROPIN A1/A2 PRECURSOR.

ID: CECA_HYACE
DE: CECROPIN A AND C
PRECURSOR.

ID: CECA_HYPCU
DE: HYPHANCIN IIID PRECURSOR.
HYPHANTRIA CECROPIN A

ID: CECA_TRINI
DE: CECROPIN A PRECURSOR.

ID: CECB1_AEDAL
DE: ANTIBIOTIC PEPTIDE
CECROPIN B1.

ID: CECB2_AEDAL
DE: ANTIBIOTIC PEPTIDE
CECROPIN B2.

ID: CECB_ANTPE
DE: CECROPIN B.

ID: CECB_BOMMO
DE: CECROPIN B PRECURSOR
(LEPIDOPTERAN A AND B) (CECB1
AND CECB2).

ID: CECB_DROMA
DE: CECROPIN B PRECURSOR.

ID: CECB_DROME
DE: CECROPIN B PRECURSOR.

ID: CECB_DROSE
DE: CECROPIN B PRECURSOR.

ID: CECB_HYACE
DE: CECROPIN B PRECURSOR
(IMMUNE PROTEIN P9).

ID: CECC1_AEDAL
DE: ANTIBIOTIC PEPTIDE
CECROPIN C1.

ID: CECC2_AEDAL
DE: ANTIBIOTIC PEPTIDE
CECROPIN C2.

ID: CECC_DROME
DE: CECROPIN C PRECURSOR.

ID: CECD_AGRCO
DE: CECROPINS D1 AND D2
(FRAGMENT). INSECT DEFENCE
PEPTIDES

ID: CECD_ANTPE
DE: CECROPIN D.

ID: CECD_HYACE
DE: CECROPIN D PRECURSOR.

ID: CECM_BOMMO
DE: (BOMBYX MORI CECROPIN
PRECURSOR)(CECROPIN).

ID: CEC_ANOGA
DE: CECROPIN PRECURSOR.

ID: CERA_CERCA
DE: CERATOTOXIN A.

ID: CERB_CERCA
DE: CERATOTOXIN B.

ID: CERC_CERCA
DE: CERATOTOXIN C PRECURSOR.

ID: CERI_CICAR
DE: CICERIN (FRAGMENT); PLANT
DEFENCE PEPTIDE.

ID: CG1_HUMAN
DE: CATHEPSIN G FRAGMENT (230-
255).

ID: CGA_HUMAN
DE: CATHEPSIN G FRAGMENT (82-
101).

ID: CGB_HUMAN
DE: CATHEPSIN G FRAGMENT (137-
158).

ID: CGC_HUMAN
DE: CATHEPSIN G FRAGMENT (210-
235).

ID: CHICATH_CHICK
DE: AVIAN CATHELICIDIN.

ID: CHY1_PAGMA
DE: CHRYSOPHSINS 1 AND
2.(PLEUROCIDIN-LIKE PEPTIDE)

ID: CHY3_PAGMA
DE: CHRYSOPHSIN
3.(PLEUROCIDIN-LIKE PEPTIDE)

ID: CICN_CICFL
DE: CICADIN (FRAGMENT).

ID: CIRA_CHAPA
DE: CIRCULIN A (CIRA).

ID: CIRB_CHAPA
DE: CIRCULIN B (CIRB).

ID: CLVAPRC_STYCL
DE: CLAVANIN A PRECURSOR;
TUNICATE ANTIMICROBIAL
PEPTIDE

ID: CLVA_STYCL
DE: CLAVANIN A; TUNICATE
DEFENCE PEPTIDE

ID: CLVD_STYCL
DE: CLAVANIN D PRECURSOR.

ID: COLE_ZOPAT
DE: COLEOPTERICIN; INSECT
DEFENCE PEPTIDE.

ID: CR10_LITSP
DE: CAERIN 1.10.

ID: CR11_LITSP
DE: CAERIN 1.1.

ID: CR12_LITCE
DE: CAERIN 1.2.

ID: CR13_LITCE
DE: CAERIN 1.3.

ID: CR14_LITGI
DE: CAERIN 1.4.

ID: CR15_LITCE
DE: CAERIN 1.5.

ID: CR16_LITXA
DE: CAERIN 1.6.

ID: CR17_LITXA
DE: CAERIN 1.7.

ID: CR18_LITCH
DE: CAERIN 1.8.

ID: CR19_LITCH
DE: CAERIN 1.9.

ID: CR21_LITSP
DE: CAERIN 2.1.

ID: CR22_LITGI
DE: CAERIN 2.2 (CONTAINS
CAERIN 2.2.1).

ID: CR23_LITCE
DE: SPLENDIPHERIN (CAERIN 2.3).

ID: CR24_LITCE
DE: CAERIN 2.4.

ID: CR25_LITGI
DE: CAERIN 2.5.

ID: CR31_LITSP
DE: CAERIN 3.1.

ID: CR32_LITCE

FIGURE 7 (cont.)

DE: CAERIN 3.2.

ID: CR33_LITCE
DE: CAERIN 3.3.

ID: CR34_LITCE
DE: CAERIN 3.4.

ID: CR41_LITCE
DE: CAERIN 4.1.

ID: CR42_LITCE
DE: CAERIN 4.2.

ID: CR43_LITCE
DE: CAERIN 4.3.

ID: CRAMPPRC_MOUSE
DE: MOUSE CATHELIN RELATED PROTEIN. MOUSE CATHELIN LIKE PROTEIN.

ID: CRAMP_MOUSE
DE: MCLP (MOUSE CATHELIN RELATED PEPTIDE), CRAMP (CATHELIN RELATED AMP)

ID: CRAMP_RAT
DE: CRAMP (FRAGMENT); (CATHELIN RELATED AMP); CATHELICIDIN

ID: CRBL_VESCR
DE: CRABROLIN.

ID: CRN_LITVA
DE: CRUSTIN, 11 KDA ATIMICROBIAL PROTEIN; CRUSTACEAN DEFENSE PROTEIN

ID: CRYP_MOUSE
DE: CRIPTDINES, CRYP 1-17, CRYPT DEFENSINS SEE DEFENSINS (DEF1_- DEFx_MOUSE).

ID: CT11_LITCI
DE: [EXTENDED TO CITROPIN 1.1.3; CITROPIN 1.1.4;]

ID: CT12_LITCI
DE: 1.2.3].

ID: CT21_LITCI
DE: 2.1].

ID: CTM_HUMAN
DE: CALCITERMIN (FRAGMENT OF CALGRANULIN C)

ID: CUP1A_CUPSA
DE: CUPIENNIN 1A

ID: CYLA_PSYLO
DE: CYCLOPSYCHOTRIDE A (CPT).

ID: DBB2_DOLAU
DE: DOLABELLANIN B2.

ID: DBIF_PIG
DE: DIAZEPAM BINDING INHIBITOR (DBI) FRAGMENT (32-86).

ID: DCD_HUMAN
DE: [CONTAINS: DCD-1].

ID: DEF10_MOUSE
DE: CRYPTDIN-10 PRECURSOR (FRAGMENT), DEFENSIN.

ID: DEF11_MOUSE
DE: CRYPTDIN-11 PRECURSOR (FRAGMENT), DEFENSIN.

ID: DEF13_MOUSE
DE: CRYPTDIN-13 PRECURSOR (FRAGMENT), DEFENSIN.

ID: DEF14_MOUSE
DE: CRYPTDIN-14 PRECURSOR (FRAGMENT), DEFENSIN.

ID: DEF15_MOUSE
DE: CRYPTDIN-15 PRECURSOR (FRAGMENT), DEFENSIN.

ID: DEF16_MOUSE
DE: CRYPTDIN-16 PRECURSOR (FRAGMENT), DEFENSIN.

ID: DEF17_MOUSE
DE: CRYPTDIN-17 PRECURSOR (CRYP17); ALPHA-DEFENSIN 17.

ID: DEF1A_STOCA
DE: DEFENSIN 1A PRECURSOR. INSECT DEFENSIN

ID: DEF1_ANOGA
DE: DEFENSIN PRECURSOR. INSECT DEFENSIN

ID: DEF1_ATEGE
DE: PRIMATE ALPHA DEFENSIN (FRAGMENT).

ID: DEF1_BOMIG
DE: INSECT DEFENSIN.

ID: DEF1_CENLL
DE: SCORPION DEFENSIN PRECURSOR.

ID: DEF1_DERVA
DE: DERMACENTOR DEFENSIN (PRECURSOR); VARISIN; INSECT DEFENSIN

ID: DEF1_MACMU
DE: NEUTROPHIL DEFENSINS 1, 3 AND 8 PRECURSOR (RMAD).

ID: DEF1_MESAU
DE: HAMSTER NEUTROPHIL PEPTIDE 1 (HANP-1); NEUTROPHIL DEFENSIN;

ID: DEF1_MOUSE

ID: DEF1_MYTGA
DE: MYTILUS DEFENSIN 1 (MGD1)

ID: DEF1_RABIT
DE: (ANTIADRENOCORTICOTROPIN PEPTIDE I)

ID: DEF1_RAT
DE: RAT NEUTROPHIL PEPTIDE (RTNP-1)(RTNP-2), RAT CORTICOSTATIN (R1, R2), DEFENSIN

ID: DEF1_SAGLA
DE: PRIMATE ALPHA DEFENSIN (FRAGMENT).

ID: DEF1_STOCA
DE: DEFENSIN 1 PRECURSOR (INSECT DEFENSIN).

ID: DEF2A_MACMU
DE: MACACA MULATTA ALPHA-DEFENSIN-2, RMAD-2

ID: DEF2A_STOCA
DE: DEFENSIN 2A PRECURSOR. INSECT DEFENSIN

ID: DEF2B_MACMU
DE: MACACA MULATTA ALPHA-DEFENSIN 2 (NAME CONFLICT WITH DEF2A_MACMU).

ID: DEF2_ANOGA
DE: DEFENSIN.

ID: DEF2_APIME
DE: DEFENSIN (FRAGMENT).

ID: DEF2_MESAU
DE: HAMSTER NEUTROPHIL PEPTIDE 2 (HANP-2); NEUTROPHIL DEFENSIN;

ID: DEF2_MOUSE
DE: CRYPTDIN 2 PRECURSOR. DEFENSIN.

ID: DEF2_MYTGA
DE: MYTILUS DEFENSIN 2 PRECURSOR (MGD2)

ID: DEF2_RABIT
DE: (ANTIADRENOCORTICOTROPIN PEPTIDE II).

ID: DEF2_RAT
DE: RAT NEUTROPHIL ANTIBIOTIC PEPTIDE NP-2 PRECURSOR; DEFENSIN

ID: DEF2_STOCA
DE: DEFENSIN 2 PRECURSOR (INSECT DEFENSINE).

FIGURE 7 (cont.)

ID: DEF3_MACMU
DE: NEUTROPHIL DEFENSINS 1, 3 AND 8 PRECURSOR (RMAD).

ID: DEF3_MESAU
DE: HAMSTER NEUTROPHIL PEPTIDE 3 (HANP-3); NEUTROPHIL DEFENSIN;

ID: DEF3_MOUSE
DE: CRYPTDIN 3 PRECURSOR, DEFENSIN.

ID: DEF3_RABIT
DE: (ANTIADRENOCORTICOTROPIN PEPTIDE III).

ID: DEF3_RAT
DE: RAT NEUTROPHIL PEPTIDE (RTNP-3), RAT CORTICOSTATIN (R3), DEFENSIN

ID: DEF4_ANDAU
DE: ANDROCTONUS DEFENSIN(INSECT-DEFENSIN-LIKE)

ID: DEF4_HUMAN
DE: NEUTROPHIL DEFENSIN 4 (HNP-4) (HP4).

ID: DEF4_MESAU
DE: HAMSTER NEUTROPHIL PEPTIDE 4 (HANP-4); NEUTROPHIL DEFENSIN;

ID: DEF4_MOUSE
DE: CRYPTDIN 4 PRECURSOR (FRAGMENT), DEFENSIN.

ID: DEF4_RABIT
DE: (ANTIADRENOCORTICOTROPIN PEPTIDE III).

ID: DEF4_RAT
DE: RAT NEUTROPHIL PEPTIDE (RTNP-4), RAT CORTICOSTATIN (R4), DEFENSIN

ID: DEF5_HUMAN
DE: DEFENSIN 5 PRECURSOR.

ID: DEF5_MACMU
DE: MACACA MULATTA DEFENSIN-4 AND DEFENSIN-5

ID: DEF5_MOUSE
DE: CRYPTDIN 5, DEFENSIN.

ID: DEF5_RABIT
DE: (MICROBICIDAL PEPTIDE NP-4).

ID: DEF5_RAT
DE: DEFENSIN 5 PRECURSOR (RD-5).

ID: DEF6_HUMAN
DE: DEFENSIN 6 PRECURSOR, HD6.

ID: DEF6_MOUSE
DE: CRYPTDIN-6/12 PRECURSOR (DEFENSIN).

ID: DEF6_RABIT
DE: (MICROBICIDAL PEPTIDE NP-5).

ID: DEF7_MACMU
DE: MACACA MULATTA DEFENSIN-6 AND DEFENSIN-7

ID: DEF7_MOUSE
DE: CRYPTDIN-7 PRECURSOR (FRAGMENT). DEFENSIN

ID: DEF7_RABIT
DE: DEFENSIN

ID: DEF8_MOUSE
DE: CRYPTDIN-8 PRECURSOR (FRAGMENT), DEFENSIN.

ID: DEF9_MOUSE
DE: CRYPTDIN-9 PRECURSOR (FRAGMENT), DEFENSIN.

ID: DEFA_AEDAE
DE: DEFENSIN A PRECURSOR (AADEF)(ARTHROPOD DEFENSIN).

ID: DEFA_ANOCP
DE: DEFENSIN A (INSECT DEFENSIN).

ID: DEFA_MAMBR
DE: DEFENSIN A, INSECT DEFENSIN.

ID: DEFA_MOUSE
DE: TESTIS DEFENSIN PRECURSOR (FRAGMENT).

ID: DEFA_MYTED
DE: MYTILUS DEFENSIN A; MULLUSC DEFENSIN

ID: DEFA_ORNMO
DE: DEFENSIN A.

ID: DEFA_RHOPR
DE: RHODNIUS DEFENSINS A AND B (INSECT DEFENSINS)

ID: DEFA_ZOPAT
DE: INSECT DEFENSIN, ISOFORMS B AND C.

ID: DEFB_AEDAE
DE: DEFENSIN B; INSECT DEFENSIN.

ID: DEFB_ANOCP
DE: DEFENSIN B(INSECT DEFENSIN).

ID: DEFB_MOUSE
DE: TESTIS DEFENSIN PRECURSOR (FRAGMENT).

ID: DEFB_MYTED
DE: DEFENSIN B

ID: DEFB_ORNMO
DE: DEFENSIN B.

ID: DEFC_AEDAE
DE: DEFENSIN C; INSECT DEFENSIN.

ID: DEFC_ORNMO
DE: DEFENSIN C.

ID: DEFC_RHOPR
DE: RHODNIUS DEFENSINS C (INSECT DEFENSINS)

ID: DEFD_AEDAL
DE: DEFENSIN D PRECURSOR (AALDEFD) (FRAGMENT).INSECT DEFENSIN

ID: DEFD_ORNMO
DE: DEFENSIN D.

ID: DEFI_AESCY
DE: INSECT DEFENSIN.

ID: DEFI_ALLDI
DE: INSECT DEFENSIN.

ID: DEFI_APIME
DE: ROYALISIN, INSECT DEFENSIN.

ID: DEFI_BOMPA
DE: INSECT DEFENSIN.

ID: DEFI_DROME
DE: INSECT DEFENSIN PRECURSOR.

ID: DEFI_PALPR
DE: INSECT DEFENSIN.

ID: DEFI_PHLDU
DE: INSECT DEFENSIN.

ID: DEFI_PHOTE
DE: PHORMICIN PRECURSOR (INSECT DEFENSINS A AND B).

ID: DEFI_PYRAP
DE: INSECT DEFENSIN.

ID: DEFI_TENMO
DE: TENECIN 1 PRECURSOR - INSECT DEFENSIN-LIKE.

ID: DEFN_HELVI
DE: HELIOMICIN, INSECT DEFENSIN.

ID: DEFN_HUMAN

FIGURE 7 (cont.)

DE: DEF1_HUMAN, DEF2_HUMAN, DEF3_HUMAN

ID: DEFV_MOUSE
DE: DEFENSIN-LIKE PROTEIN 4C-5 PRECURSOR.

ID: DEFW_MOUSE
DE: DEFENSIN-LIKE PROTEIN 4C-2 PRECURSOR.

ID: DEFX_MOUSE
DE: MOUSE DEFENSIN, CRYPTDIN-RELATED PROTEIN 4C-4 PRECURSOR (CRS4C).

ID: DEFY_MOUSE
DE: CRYPTDIN-RELATED 4C PRECURSOR (CRS4C), DEFENSIN.

ID: DEFZ_MOUSE
DE: CRYPTDIN-RELATED 1C PRECURSOR (CRS1C), DEFENSIN.

ID: DEF_ACALU
DE: DEFENSIN 1 PRECURSOR.

ID: DEF_AEDAL
DE: DEFENSIN (FRAGMENT).
INSECT DEFENSIN

ID: DEF_ANOCP
DE: DEFENSINS A AND B INSECT DEFENSIN

ID: DEF_CAVPO
DE: DEF1_CAVPO; DEDF2_CAVPO (CORTICOSTATIC PEPTIDE GP-CS1) (CP-1)].

ID: DEF_ERITE
DE: INSECT DEFENSIN.

ID: DEF_GALME
DE: ANTIFUNGAL PEPTIDE GALLERIMYCIN, INSECT DEFENSIN (?).

ID: DEF_LEIQU
DE: SCORPION DEFENSIN (INSECT DEFENSIN-LIKE)

ID: DEF_ORYRH
DE: DEFENSIN PRECURSOR.
INSECT DEFENSIN

ID: DERB_PHYBI
DE: DERMATOXIN PRECURSOR.

ID: DIPA_PROTE
DE: DIPTERICIN A; INSECT DEFENCE PEPTIDE

ID: DIPD_PHOTE
DE: DIPTERICIN D PRECURSOR; INSECT DEFENCE PEPTIDE

ID: DIP_DROME

DE: DIPTERICIN PRECURSOR.
INSECT DEFENCE PEPTIDE

ID: DISA_PHYDI
DE: DISA, CHAIN 1 OF DISTINCTIN, HETERODIMERIC ANTIMICROBIAL PEPTIDE

ID: DISB_PHYDI
DE: DISB, CHAIN 2 OF DISTINCTIN, HETERODIMERIC ANTIMICROBIAL PEPTIDE

ID: DLP1_ORNAN
DE: DEFENSIN-LIKE PEPTIDE 1 (DLP-1).

ID: DLP2_ORNAN
DE: DEFENSIN-LIKE PEPTIDE 2 (DLP-2).

ID: DLP3_ORNAN
DE: DEFENSIN-LIKE PEPTIDE 3 (DLP-3).

ID: DMS1_PACDA
DE: DERMASEPTIN PD-1-5 PRECURSOR.

ID: DMS1_PHYBI
DE: DERMASEPTIN B1 PRECURSOR

ID: DMS1_PHYSA
DE: DERMASEPTIN 1 (DS I)

ID: DMS2_AGAAN
DE: DERMASEPTIN AA-2-5 PRECURSOR.

ID: DMS2_PACDA
DE: DERMASEPTIN PD-2-2 PRECURSOR.

ID: DMS2_PHYBI
DE: ADENOREGULIN (DERMASEPTIN B2).

ID: DMS2_PHYSA
DE: DERMASEPTIN 2 (DS II).

ID: DMS3_AGAAN
DE: DERMASEPTIN AA-3-1 PRECURSOR.

ID: DMS3_PACDA

ID: DMS3_PHYBI
DE: DERMASEPTIN B3.

ID: DMS3_PHYSA
DE: DERMASEPTIN 3 (DS III).

ID: DMS4_AGAAN
DE: DERMASEPTIN AA-3-3 PRECURSOR.

ID: DMS4_PACDA
DE: DERMASEPTIN PD-3-6 PRECURSOR.

ID: DMS4_PHYBI

DE: DERMASEPTIN B3.

ID: DMS4_PHYSA
DE: DERMASEPTIN 4 (DS IV).

ID: DMS5_AGAAN
DE: DERMASEPTIN AA-3-4 PRECURSOR.

ID: DMS5_PACDA
DE: DERMASEPTIN PD-3-7 PRECURSOR.

ID: DMS5_PHYBI
DE: DERMASEPTIN B5.

ID: DMS5_PHYSA
DE: DERMASEPTIN 5 (DS V).

ID: DMS6_AGAAN
DE: DERMASEPTIN AA-3-6 PRECURSOR.

ID: DMS6_PHYBI
DE: DERMASEPTIN B6.

ID: DMS7_PHYBI
DE: DERMASEPTIN DRG3 PRECURSOR.

ID: DMS8_PHYBI
DE: PHYLLOXIN PRECURSOR; DERMASEPTIN-DERIVED PEPTIDE.

ID: DMYC_DROME
DE: DROSOMYCIN PRECURSOR (CYSTEINE-RICH PEPTIDE); INSECT DEFENCE PEPTIDE

ID: DMYC_DROTI
DE: DROSOMYCIN-LIKE PEPTIDE.

ID: DROS_DROME
DE: DROSOCIN PRECURSOR; INSECT DEFENCE PEPTIDE

ID: DTH_HALAU
DE: CHAIN OF DICYNTHAURIN

ID: EAFP_EUCUL
DE: EAFP1, PLANT ANTIFUNGAL PEPTIDE

ID: EAP_BOVIN
DE: ENTERIC BETA-DEFENSIN PRECURSOR.

ID: EBCN_BOMMO
DE: ENBOCIN - INSECT DEFENCE PEPTIDE

ID: ECAT1_EQUCA
DE: ECATH-3, HORSE MYELOID CATHELICIDIN 3

ID: ECAT2_EQUCA
DE: ECATH-2, HORSE MYELOID CATHELICIDIN 3

ID: ECAT3_EQUCA

FIGURE 7 (cont.)

DE: ECATH-3, HORSE MYELOID
CATHELICIDIN 3

ID: ELAF_HUMAN
DE: ANTILEUKOPROTEINASE)
(SKALP).

ID: EMB1_CAVPO
DE: EOSINOPHIL GRANULE MAJOR
BASIC PROTEIN 1 PRECURSOR
(MBP-1).

ID: EMB2_CAVPO
DE: EOSINOPHIL GRANULE MAJOR
BASIC PROTEIN 2 PRECURSOR
(MBP-2).

ID: EMBP_HUMAN
DE: ASSOCIATED MAJOR BASIC
PROTEIN).

ID: ENAP1_HORSE
DE: ENAP-1 (ANTIBACTERIAL
PEPTIDE) GRANULIN.
INCOMPLETE.

ID: ENAP2_HORSE
DE: ANTIMICROBIAL PEPTIDE
ENAP-2 (FRAGMENT).

ID: ENK_BOVIN
DE: ENKELYTIN; DERIVED FROM
PROENKEPHALIN A PRECURSOR
[CONTAINS: DE MET-
ENKEPHALIN; LEU-ENKEPHALIN]

ID: ENTA_ENTDI
DE: NONPATHOGENIC PORE-
FORMING PEPTIDE PRECURSOR
(APNP).DISPARPORE-A

ID: ENTB_ENTDI
DE: PORE-FORMING PROTEIN
ISOFORM B PRECURSOR.
DISPARPORE-B

ID: ENTC_ENTDI
DE: PORE-FORMING PROTEIN
ISOFORM B PRECURSOR.
DISPARPORE-B

ID: ES1A_RANES
DE: ESCULENTIN-1A.

ID: ES1B_RANES
DE: ESCULENTIN-1B PRECURSOR.

ID: ES1_RANES
DE: ESCULENTIN-1.

ID: ES2A_RANES
DE: ESCULENTIN-2A.

ID: ES2B_RANES
DE: ESCULENTIN-2B.

ID: ES2L_RANLU
DE: ESCULENTIN-2L.

ID: ESC2B_RANBE
DE: ESCULENTIN-2B.

ID: FACTD_TACTR
DE: FACTOR.D PRECURSOR;
CHELICERATE DEFENCE PROTEIN

ID: FOR1_MYRGU
DE: FORMAECIN 1, INSECT
DEFENCE PEPTIDE

ID: FOR2_MYRGU
DE: FORMAECIN 2, INSECT
DEFENCE PEPTIDE

ID: GAE1_RANRU
DE: GAEGURIN-1.

ID: GAE2_RANRU
DE: GAEGURIN-2.

ID: GAE3_RANRU
DE: GAEGURIN-3.

ID: GAE4_RANRU
DE: GAEGURIN-4.

ID: GAE5_RANRU
DE: GAEGURIN-5.

ID: GAE6_RANRU
DE: GAEGURIN-6.

ID: GALN_KASSE
DE: GALENSIN PRECURSOR, FROG
ANTIMICROBIAL PEPTIDE.

ID: GAM_ANOGA
DE: GAMBICIN; PUTATIVE
INFECTION RESPONSIVE SHORT
PEPTIDE (PRECURSOR)

ID: GKBL_GINBI
DE: GINKBILOBIN (GNL)
(FRAGMENT).

ID: GLOV_HYACE
DE: GLOVERIN, INSECT DEFENCE
PEPTIDE

ID: GMAP43PRC_CAVPO
DE: GUINEA PIG MYELOID
ANTIBACTERIAL PEPTIDE
PRECURSOR; CAP 11 ;
CATHELICIDIN

ID: GMAP43_CAVPO
DE: GUINEA PIG MYELOID
ANTIBACTERIAL POLYPEPTIDE (11
KDA POLYPEPTIDE) CAP 11

ID: GNLY_HUMAN
DE: ACTIVATION PROTEIN 519).

ID: GOME_ACAGO
DE: GOMESIN, ARTHROPOD
DEFENSE PEPTIDE

ID: H1_SALSA
DE: HISTONE H1. (NB THE
ACCESSION NUMBER PROVIDED
IS FOR SALMO GAIRDNERI)

ID: H2AX_ONCMY
DE: HISTONE H2A (FRAGMENT).

ID: H2A_BUFBG
DE: HISTONE H2A (CONTAINS:
BUFORINS I AND II) (FRAGMENT).

ID: H2A_HIPHI
DE: HISTONE H2A [CONTAINS:
HIPPOSIN] (FRAGMENT).

ID: HALN_HALAU
DE: CHAINS OF HALOCIDIN

ID: HDRN_HADAZ
DE: HARDRURIN

ID: HEMI_PYRAP
DE: HEMIPTERICIN; INSECT
DEFENCE PROTEIN

ID: HEMO_HYACE
DE: HEMOLIN PRECURSOR (P4
PROTEIN) (HEMOCYTE
AGGREGATION
INHIBITOR),INSECT DEFENCE
PROTEIN

ID: HEMO_MANSE
DE: HEMOLIN PRECURSOR (P4
PROTEIN) (HEMOCYTE
AGGREGATION
INHIBITOR),INSECT
ANTIMICROBIAL PEPTIDE

ID: HEPC_HUMAN
DE: ANTIMICROBIAL PEPTIDE
HEPCIDIN PRECURSOR (LIVER-
EXPRESSED ANTIMICROBIAL
PEPTIDE), LEAP-1 .

ID: HEPC_MORCH
DE: HEPCIDIN.

ID: HEPC_MOUSE
DE: PROHEPCIDIN.

ID: HEPC_ONCMY
DE: PUTATIVE HEPCIDIN
ANTIBACTERIAL PEPTIDE
(FRAGMENT).

ID: HEPC_PIG
DE: ANTIMICROBIAL PEPTIDE
HEPCIDIN. LIVER EXPRESSED

ID: HEPC_RAT
DE: PROHEPCIDIN.

ID: HFIAP1_MYXGL
DE: HAG FISH INTESTINAL
ANTIMICROBIAL PEPTIDES
(HFIAP-1 AND -2). CRANIATE
DEFENSE PEPTIDE
(CATHELICIDIN)

FIGURE 7 (cont.)

ID: HFIAP3_MYXGL
DE: HAG FISH INTESTINAL
ANTIMICROBIAL PEPTIDE (HFIAP-
3). CRANIATE DEFENSE PEPTIDE
(CATHELICIDIN)

ID: HIS1_HUMAN
DE: HISTATIN 1 PRECURSOR
(HISTIDINE-RICH PROTEIN 1)
(POST-PB PROTEIN) (PPB).

ID: HIS1_MACFA
DE: HISTATIN 1.

ID: HIS3_HUMAN
DE: HISTATIN 3 PRECURSOR
(HISTIDINE-RICH PROTEIN 3) (PB)
(BASIC HISTIDINE RICH PROTEIN)
(CONTAINS: HISTATINS 4 TO 12).

ID: HIS5_HUMAN
DE: HISTATIN 5 (HISTIDINE-RICH
PROTEINS5) (PB) (BASIC
HISTIDINE-RICH PROTEIN).

ID: HLT_HUMAN
DE: LACTOFERRIN FRAGMENT
HLT1 AND 2.

ID: HOL2_HOLDI
DE: HOLOTRICIN 2 PRECURSOR;
INSECT DEFENCE PEPTIDE;
COLEOPTERICIN

ID: HOL3_HOLDI
DE: HOLOTRICIN 3 PRECURSOR;
INSECT DEFENCE PEPTIDE;
COLEOPTERICIN

ID: HPA1_RANES
DE: HEMOLYTIC PROTEIN A1
(FRAGMENT).

ID: HPB9_RANES
DE: HEMOLYTIC PROTEIN B9
(FRAGMENT).

ID: HRCYC_HUMAN
DE: RETROCYCLIN.

ID: HYP_ARAHY
DE: HYPOGIN; PLANT
ANTIFUNGAL PPOLYPEPTIDE
(FRAGMENT)

ID: HYTA_APIME
DE: HYMENOPTAECIN; INSECT
DEFENCE PEPTIDE

ID: IAAT_MAIZE
DE: ALPHA-AMYLASE/TRYPSIN
INHIBITOR (PLANT ANTIFUNGAL
PROTEIN).

ID: IBAMP_IMPBA
DE: ANTIMICROBIAL PEPTIDES
PRECURSOR: IBAMP1 - IBAMP4,
PLANT DEFENCE PEPTIDES

ID: INDPRC_BOVIN
DE: INDOLICIDIN
PRECURSOR(CATHELICIDIN)

ID: IND_BOVIN
DE: INDOLICIDIN.

ID: ISCT_OPIMA
DE: ISCT CYTOTOXIC SCORPION
PEPTIDE

ID: JAP1_RANJA
DE: JAPONICIN-1.

ID: JAP2_RANJA
DE: JAPONICIN-2.

ID: KAB1_OLDAF
DE: KALATA B1.

ID: LAP_BOVIN
DE: LINGUAL ANTIMICROBIAL
PEPTIDE PRECURSOR, BOVINE
BETA-DEFENSIN.

ID: LBP_HUMAN
DE: LIPOPOLYSACCHARIDE-
BINDING PROTEIN PRECURSOR.

ID: LBP_RABIT
DE: LIPOPOLYSACCHARIDE-
BINDING PROTEIN PRECURSOR
(LBP).

ID: LCFB_BOVIN
DE: LACTOFERRICIN B RELATED
FRAGMENTS
(LACTOFERRIN/LACTOTRANSFER
RIN FRAGMENTS).

ID: LCFH_HUMAN
DE: LACTOFERRICIN H
(LACTOFERRIN FRAGMENT).

ID: LCRP_PETMA
DE: CORTICOSTATIN-RELATED
PROTEIN LCRP.

ID: LEAP2_PIG

ID: LEB1_BOMMO
DE: LEBOCIN 1/2 PRECURSOR;
INSECT ANTIMICROBIAL PROTEIN

ID: LEB3_BOMMO
DE: LEBOCIN 3; INSECT DEFENCE
PEPTIDE

ID: LEB4_BOMMO
DE: LEBOCIN 4 PRECURSOR (FROM
GENE); INSECT ANTIMICROBIAL
PROTEIN

ID: LEVI_XENLA
DE: PROLEVITIDE PRECURSOR.

ID: LL37PRC_HUMAN
DE: 19 KD LIPOPOLYSACCHARIDE-
BINDING PROTEIN PRECURSOR (FALL39, LL37,
HCAP18)(CATHELICIDIN).

ID: LL37_HUMAN
DE: HCAP-18, FALL-39, LL-37.

ID: LLP1_HIV
DE: LLP1 (LENTIVIRUS LYTIC
PEPTIDE 1)

ID: LLP_EIAV
DE: LLP (LENTIVIRUS LYTIC
PEPTIDE)

ID: LLP_SIV
DE: LLP (LENTIVIRUS LYTIC
PEPTIDE)

ID: LTX1_LYCCA
DE: LYCOTOXIN 1

ID: LTX2_LYCCA
DE: LYCOTOXIN 2

ID: LUM1_LUMRU
DE: LUMBRICIN 1; WORM
DEFENSE PEPTIDE

ID: LYS_EISFO
DE: FETIDIN, LYSENIN-RELATED
PROTEIN (HEMOLYSIN).

ID: MAC11_LITGE
DE: MACULATIN 1.1, AMPHIBIAN
DEFENCE PEPTIDE

ID: MAC12_LITGE
DE: MACULATIN 1.2, AMPHIBIAN
DEFENCE PEPTIDE

ID: MAC21_LITGE
DE: MACULATIN 2.1, AMPHIBIAN
DEFENCE PEPTIDE

ID: MAC31_LITGE
DE: MACULATIN 3.1, AMPHIBIAN
DEFENCE PEPTIDE

ID: MAG1_XENLA
DE: MAGAININ 1.

ID: MAG2_XENLA
DE: MAGAININ 2.

ID: MAGA_XENLA
DE: MAGAININS PRECURSOR.

ID: MAP34_CAPHI
DE: GAOAT MAP34-A (MAP34-B);
CATHELICIDIN.

ID: MAST_POLJA
DE: POLISTES MASTOPARAN.

ID: MAST_VESBA
DE: MASTOPARAN B.

ID: MAST_VESCR
DE: MASTOPARAN C.

FIGURE 7 (cont.)

ID: MAST_VESLE
DE: MASTOPARAN.

ID: MAST_VESMA
DE: MASTOPARAN M (MAST CELL-DEGRANULATING PEPTIDE).

ID: MAST_VESOR
DE: MASTOPARAN (HISTAMINE RELEASING PEPTIDE I) (HR-I).

ID: MAST_VESXA
DE: MASTOPARAN X.

ID: MAX1_BOMMA
DE: MAXIMIN 1 PRECURSOR [CONTAINS: MAXIMIN-1].

ID: MAX2_BOMMA
DE: MAXIMIN 2 PRECURSOR [CONTAINS: MAXIMIN-2].

ID: MAX3_BOMMA
DE: MAXIMIN 3 PRECURSOR [CONTAINS: MAXIMIN-3].

ID: MAX4_BOMMA
DE: MAXIMIN 4 PRECURSOR CONTAINS: MAXIMIN-4]

ID: MAX5_BOMMA
DE: MAXIMIN 5 PRECURSOR [CONTAINS: MAXIMIN-5].

ID: MAX6_BOMMA
DE: MAXIMIN-6.

ID: MAX7_BOMMA
DE: MAXIMIN-7.

ID: MAX8_BOMMA
DE: MAXIMIN-8.

ID: MBP1_MAIZE
DE: ANTIMICROBIAL PEPTIDE MBP-1; PLANT DEFENCE PEPTIDE

ID: MCDP_APIME
DE: MAST CELL DEGRANULATING PEPTIDE (MCD) (PEPTIDE 401).

ID: MCDP_MEGPE
DE: MAST CELL DEGRANULATING PEPTIDE (MCD).

ID: MEL1_APIME
DE: MELITTIN MAJOR PRECURSOR.

ID: MEL2_APIME
DE: MELITTIN MINOR.

ID: MEL_APIDO
DE: MELITTIN.

ID: MEL_APIFL
DE: MELITTIN.

ID: MIS_MISAN
DE: MISGURIN

ID: MK1_PALPR
DE: METALNIKOWIN I; INSECT DEFENCE PEPTIDE

ID: MK2A_PALPR
DE: METALNIKOWIN II-A; INSECT DEFENCE PEPTIDE

ID: MK2B_PALPR
DE: METALNIKOWIN II-B; INSECT DEFENCE PEPTIDE

ID: MK3_PALPR
DE: METALNIKOWIN III; INSECT DEFENCE PEPTIDE

ID: MRCN_BOMMO
DE: MORICINS 1 AND 2 PRECURSOR (INSECT DEFENCE PEPTIDE)(NAME CONFLICT)

ID: MRP_RATAG
DE: FROG MELITTIN-RELATED PEPTIDE (MRP)

ID: MSGP_MOUSE
DE: MYELOID SECONDARY GRANULE PROTEIN (MRNA) (CLONE B6).

ID: MTK_DROME
DE: METCHNIKOWIN PRECURSOR; INSECT DEFENCE PEPTIDE

ID: MYCA_MYTGA
DE: MYTICIN A PRECURSOR, MULLUSC DEFENSE PEPTIDE

ID: MYCB_MYTGA
DE: MYTICIN B PRECURSOR, MULLUSC DEFENCE PEPTIDE

ID: MYMY_MYTED
DE: MYTIMYCIN (FRAGMENT).

ID: MYTA_MYTED
DE: MYTILIN A; MULLUSC DEFENCE PEPTIDE

ID: MYTB_MYTED
DE: MYTILIN B; MULLUSC DEFENCE PEPTIDE

ID: MYTB_MYTGA
DE: MYTILIN B; MULLUSC DEFENCE PEPTIDE

ID: MYTC_MYTGA
DE: MYTILIN C; MULLUSC DEFENCE PEPTIDE

ID: MYTD_MYTGA
DE: MYTILIN D; MULLUSC DEFENCE PEPTIDE

ID: MYTG_MYTGA
DE: MYTILIN G1; MULLUSC DEFENCE PEPTIDE

ID: NGC1_RANNI
DE: NIGROCIN-1

ID: NGC2_RANNI
DE: NIGROCIN-2

ID: NKK1_PIG
DE: NK-LYSIN 1.

ID: NKK2_PIG
DE: NK-LYSIN 2.

ID: NKL_EQUCA
DE: ANTIMICROBIAL PEPTIDE NK-LYSIN.

ID: NKL_PIG
DE: NK-LYSIN PRECURSOR (NKL) (FRAGMENT).PORE-FORMING PEPTIDE

ID: NPA_NAEFO
DE: NAEGLERIAPORE A PORE-FORMING PEPTIDE.

ID: NPB_NAEFO
DE: NAEGLERIAPORE B PORE-FORMING PEPTIDE.

ID: OLPA_TOBAC
DE: OSMOTIN-LIKE PROTEIN PRECURSOR (PATHOGENESIS-RELATED PROTEIN PR-5D).

ID: ONCIII_ONCMY
DE: HISTONE H6-LIKE PROTEIN (FRAGMENT).

ID: ONCII_ONCMY
DE: III].

ID: OP01_OXYKI
DE: OXYOPININ 1 (OXKI1).

ID: OP2_OXYKI
DE: OXYOPININ 2 (2A, 2B, 2C & 2D).

ID: OPO1_OPICA
DE: OPISTOPORIN 1 & 2.

ID: P15A_RABIT
DE: 15 KD PROTEIN A PRECURSOR (P15A).

ID: P15B_RABIT
DE: 15 KD PROTEIN B PRECURSOR (P15B).

ID: PAFP_PHYAM
DE: ANTI-FUNGAL PROTEIN 1 PRECURSOR (PAFP-S; AFPS-1). PLANT DEFENSE PEPTIDE

ID: PAL1C_RANPA
DE: PALUSTRIN-1C. INSULIN-RELEASING PEPTIDE

ID: PAN1_PANIM
DE: PANDININ 1; SCORPRION VENOM ANTIMICROBIAL PEPTIDE

FIGURE 7 (cont.)

ID: PAN2_PANIM
DE: PANDININ 1; SCORPRION VENOM ANTIMICROBIAL PEPTIDE

ID: PAR1_PARAS
DE: PARASIN 1 (HISTONE 2A DERIVED DEFENSE PEPTIDE).

ID: PARDX_PARMA
DE: PARDAXIN.

ID: PARDX_PARPV
DE: PARDAXINS P-1, P-2 AND P3

ID: PBPO_PARSC
DE: PARABUTOPORIN; BMKBPP.

ID: PCG1_PACGO
DE: PONERICIN G1.

ID: PCG2_PACGO
DE: PONERICIN G2.

ID: PCG3_PACGO
DE: PONERICIN G3.

ID: PCG4_PACGO
DE: PONERICIN G4.

ID: PCG5_PACGO
DE: PONERICIN G5.

ID: PCG6_PACGO
DE: PONERICIN G6.

ID: PCG7_PACGO
DE: PONERICIN G7.

ID: PCL1_PACGO
DE: PONERICIN L1.

ID: PCW1_PACGO
DE: PONERICIN W1.

ID: PCW3_PACGO
DE: PONERICIN W3.

ID: PCW4_PACGO
DE: PONERICIN W4.

ID: PCW5_PACGO
DE: PONERICIN W5.

ID: PCW6_PACGO
DE: PONERICIN W6.

ID: PDEF1_AESHI
DE: CYS-RICH ANTIFUNGAL PROTEIN 1 (AH-AMP1), PLANT DEFENSIN

ID: PDEF1_ARATH
DE: ANTIFUNGAL PEPTIDE PDF1, PLANT DEFENCE PEPTIDE

ID: PDEF1_BETVU
DE: ANTIFUNGAL PROTEIN AX1, PLANT DEFENSIN

ID: PDEF1_BRANA
DE: CYS-RICH ANTIFUNGAL PROTEIN 1 (AFP1) PLANT DEFENSIN (FRAGMENT).

ID: PDEF1_BRARA
DE: CYS-RICH ANTIFUNGAL PROTEIN 1 (AFP1) PLANT DEFENSIN (FRAGMENT).

ID: PDEF1_CAJCA
DE: PLANT DEFENSINS (PUTATIVE).

ID: PDEF1_CAPAN
DE: DEFENSIN J1-1 PRECURSOR.

ID: PDEF1_CLITE
DE: CYS-RICH ANTIFUNGAL PROTEIN 1(CT-AMP1), PLANT DEFENSIN

ID: PDEF1_DAHME
DE: CYS-RICH ANTIFUNGAL PROTEIN 1 (DM-AMP1), PLANT DEFENSIN

ID: PDEF1_HEUSA
DE: CYS-RICH ANTIFUNGAL PROTEIN 1 (HS-AFP1), PLANT DEFENSIN

ID: PDEF1_ORYSA
DE: PLANT DEFENSIN (PUTATIVE)

ID: PDEF1_PETHY
DE: FLORAL DEFENSIN-LIKE PROTEIN 1 PRECURSOR (PHD1)(PLANT DEFENSIN)

ID: PDEF1_PICGL
DE: PLANT DEFENSIN (PUTATIVE)

ID: PDEF1_PISSA
DE: DISEASE RESISTANCE RESPONSE PROTEIN 39 PRECURSOR, PLANT DEFENSIN

ID: PDEF1_RAPSA
DE: CYS-RICH ANTIFUNGAL PROTEIN 1 (RS-AFP1), PLANT DEFENSIN

ID: PDEF1_SINAL
DE: CYS-RICH ANTIFUNGAL PROTEIN 1 (AFP1)(M1) PLANT DEFENSIN

ID: PDEF1_SORBI
DE: SMALL PROTEIN INHIBITOR OF INSECT ALPHA-AMYLASES 1 (SI ALPHA-1).

ID: PDEF1_SPIOL
DE: CYS-RICH ANTIFUNGAL PROTEIN 2 (SO-D1) PLANT DEFENSIN FRAGMENT

ID: PDEF1_VICFA
DE: FABATIN; PLANT DEFENSIN

ID: PDEF1_VIGRA
DE: PLANT DEFENSIN (PUTATIVE)

ID: PDEF1_WHEAT
DE: GAMMA-1 PUROTHIONIN (THG-1)PLANT DEFENSIN.

ID: PDEF2A_SINAL
DE: CYS-RICH ANTIFUNGAL PROTEIN 2 (AFP2A) (M2A)PLANT DEFENSIN

ID: PDEF2B_SINAL
DE: CYS-RICH ANTIFUNGAL PROTEIN 2B (AFP2B) (M2B) PLANT DEFENSIN.

ID: PDEF2_ARATH
DE: PUTATIVE ANTIFUNGAL PROTEIN (CYSTEINE-RICH ANTIFUNGAL PROTEIN), PLANT DEFENSIN

ID: PDEF2_BETVU
DE: ANTIFUNGAL PROTEIN AX2.

ID: PDEF2_BRANA
DE: CYS-RICH ANTIFUNGAL PROTEIN 2 (AFP2); PLANT DEFENSIN (FRAGMENT).

ID: PDEF2_BRARA
DE: CYS-RICH ANTIFUNGAL PROTEIN 2 (AFP2) PLANT DEFENSIN (FRAGMENT).

ID: PDEF2_CAPAN
DE: DEFENSIN J1-2 PRECURSOR

ID: PDEF2_PETHY
DE: FLORAL DEFENSIN-LIKE PROTEIN 2 PRECURSOR (PHD2).

ID: PDEF2_PISSA
DE: CYS-RICH ANTIFUNGAL PROTEIN (p1230), PLANT DEFENSIN

ID: PDEF2_RAPSA
DE: CYS-RICH ANTIFUNGAL PROTEIN 1 (RS-AFP2), PLANT DEFENSIN

ID: PDEF2_SORBI
DE: CYS-RICH ANTIFUNGAL PROTEIN (SI-ALFA-2), PLANT DEFENSIN

ID: PDEF2_SPIOL
DE: CYS-RICH ANTIFUNGAL PROTEIN 2 (SO-D2) PLANT DEFENSIN

ID: PDEF2_VICFA
DE: FABATIN-2 (PLANT DEFENSIN)

FIGURE 7 (cont.)

ID: PDEF2_WHEAT
DE: Gamma-2 purothionin (TIIG-2), PLANT DEFENSIN.

ID: PDEF3_ARATH
DE: GAMMA-THIONIN HOMOLOG AT2G02100 PRECURSOR (THG1), PLANT DEFENSIN (PUTATIVE)

ID: PDEF3_BRARA
DE: CYS-RICH ANTIFUNGAL PROTEIN 3 (AFP3) PLANT DEFENSIN (PUTATIVE).

ID: PDEF3_PISSA
DE: (ANTIFUNGAL PROTEIN PSD1).

ID: PDEF3_SORBI
DE: PLANT DEFENSIN.

ID: PDEF3_SPIOL
DE: CYS-RICH ANTIFUNGAL PROTEIN 2 (SO-D3) PLANT DEFENSIN, FRAGMENT

ID: PDEF4_ARATH
DE: GAMMA-THIONIN HOMOLOG AT2G02120 PRECURSOR(THG-2); PLANT DEFENSIN

ID: PDEF4_PISSA
DE: DEFENSE-RELATED PEPTIDE 2 (DEFENSIN 2) (ANTIFUNGAL PROTEIN PSD2).

ID: PDEF4_SPIOL
DE: CYS-RICH ANTIFUNGAL PROTEIN 2 (SO-D5) PLANT DEFENSIN, FRAGMENT

ID: PDEF5_SPIOL
DE: CYS-RICH ANTIFUNGAL PROTEIN 2 (SO-D6) PLANT DEFENSIN, FRAGMENT

ID: PDEF6_SPIOL
DE: CYS-RICH ANTIFUNGAL PROTEIN 2 (SO-D7) PLANT DEFENSIN, FRAGMENT

ID: PDEF7_SPIOL
DE: GAMMA-THIONIN 5 (DEFENSIN D5) (FRAGMENT).

ID: PDEFA_HELAN
DE: FLOWER-SPECIFIC GAMMA-THIONIN PRECURSOR (DEFENSIN SD2).

ID: PDEFB_HELAN
DE: DEFENSIN (FRAGMENT).

ID: PDEFC_HELAN
DE: DEFENSIN CUA1 (FRAGMENT).

ID: PDEF_HORVU

DE: CYS-RICH ANTIFUNGAL PROTEIN (GAMMA1-H), PLANT DEFENSIN

ID: PDEF_MAIZE
DE: GAMMA-ZEATHIONIN 1 (THG1) PLANT DEFENSIN.

ID: PDEF_MEDSA
DE: ANTIFUNGAL PROTEIN PRECURSOR (AFP) PLANT DEFENSIN.

ID: PDEF_NICAL
DE: FLOWER-SPECIFIC DEFENSIN PRECURSOR (NAD1).

ID: PDEF_NICPA
DE: GAMMA-THIONIN 1 PRECURSOR (THG-1 PLANT DEFENSIN.

ID: PDEF_NICTA
DE: CYS-RICH ANTIFUNGAL PROTEIN (FST), PLANT DEFENSIN

ID: PDEF_PETIN
DE: CYS-RICH ANTIFUNGAL PROTEIN (PPT), PLANT DEFENSIN

ID: PDEF_SOLTU
DE: CYS-RICH ANTIFUNGAL PROTEIN (P322), PLANT DEFENSIN

ID: PDEF_SOYBN
DE: PROTEINASE INHIBITOR P322). PLANT DEFENSIN

ID: PDEF_TRIAE
DE: CYS-RICH ANTIFUNGAL PROTEIN (GAMMA1-P), PLANT DEFENSIN

ID: PDEF_VIGUN
DE: CYS-RICH ANTIFUNGAL PROTEIN (PSAS10), PLANT DEFENSIN

ID: PDEF_WASJA
DE: GAMMA-THIONIN1 PRECURSOR.

ID: PEPA_RANCA
DE: PEPSINOGEN-A DERIVED PEPTIDE (BPAAP)

ID: PEPC_RANCA
DE: PEPSINOGEN-C DERIVED PEPTIDE (bPcAP)

ID: PERF_MOUSE
DE: PERFORIN 1 PRECURSOR (P1) (LYMPHOCYTE PORE FORMING PROTEIN).

ID: PF4PF_HUMAN
DE: PLATELET FACTOR 4 (PF-4) PEPTIDE FRAGMENT.

ID: PFPA_ENTHI
DE: AMOEBAPORE PORE-FORMING PEPTIDE ISOFORM A.

ID: PFPB_ENTHI
DE: AMOEBAPORE PORE-FORMING PEPTIDE ISOFORM B.

ID: PFPC_ENTHI
DE: AMOEBAPORE PORE-FORMING PEPTIDE ISOFORM C.

ID: PFPRC_PIG
DE: PROPHENINS PRECURSOR (PF-1),(CLONE C12),(PF-2),(CLONE C6),(CATHELICIDIN).

ID: PFP_ENTHI
DE: PORE-FORMING PEPTIDE PRECURSOR (CEH-APP).

ID: PF_PIG
DE: PROPHENIN (PF-1, -2),(CLONE C6 AND C12).

ID: PG1_PIG
DE: PROTEGRIN 1 (PG-1).

ID: PG2_PIG
DE: PROTEGRIN 2 (PG-2).

ID: PG3_PIG
DE: PROTEGRIN 3 (PG-3).

ID: PG4_PIG
DE: PROTEGRIN 4(PG-4).

ID: PG5_PIG
DE: PROTEGRIN 5 (PG-5).

ID: PGK_XENLA
DE: LEVITIDE PRECURSOR FRAGMENT (ANTIMICROBIAL PEPTIDE PGK).

ID: PGLA_XENLA
DE: ANTIMICROBIAL PEPTIDE PGLA.

ID: PGPRC_PIG
DE: PROTEGRINS PRECURSOR (PG-1 - PG-5)(CATHELICIDINS).

ID: PGQ_XENLA
DE: ANTIMICROBIAL PEPTIDE PGQ.

ID: PIP_RANPI
DE: PIPININ, BREVININ-1PA

ID: PIS1_MORSA
DE: PISCIDIN 1 / MORONECIDIN

ID: PIS3_MORSA
DE: PISCIDIN 3

ID: PLE01A_PLEAM

FIGURE 7 (cont.)

DE: PLEURONECTES AMERICANUS
PLEUROCIDIN-LIKE
PREPROPOLYPEPTIDE(PLE1A)

ID: PLE01_HIPPL
DE: PLEUROCIDIN-LIKE PEPTIDE
AP1.

ID: PLE01_PLEAM
DE: PLEURONECTES AMERICANUS
PLEUROCIDIN-LIKE
PREPROPOLYPEPTIDE(PLE1)

ID: PLE02_HIPPL
DE: PLEUROCIDIN-LIKE PEPTIDE
AP2.

ID: PLE02_PLEAM
DE: PLEURONECTES AMERICANUS
PLEUROCIDIN-LIKE
PREPROPOLYPEPTIDE(PLE2)

ID: PLE03_HIPPL
DE: PLEUROCIDIN-LIKE PEPTIDE
AP3.

ID: PLE03_PLEAM
DE: PLEURONECTES AMERICANUS
PLEUROCIDIN-LIKE
PREPROPOLYPEPTIDE(PLE3)

ID: PLE04_PLEAM
DE: PLEURONECTES AMERICANUS
PLEUROCIDIN-LIKE
PREPROPOLYPEPTIDE(PLE4)

ID: PLE_PLEAM
DE: PLEUROCIDIN

ID: PMAP23PRC_PIG
DE: PIG MYELOID
ANTIBACTERIAL PEPTIDE
PRECURSOR (PMAP-23, MP23)
(CATHELICIDIN).

ID: PMAP23_PIG
DE: PIG MYELOID
ANTIBACTERIAL PEPTIDE (PMAP-23).

ID: PMAP36PRC_PIG
DE: PIG MYELOID
ANTIBACTERIAL PEPTIDE
PRECURSOR (PMAP-36,
MP36)(CATHELICIDIN)

ID: PMAP36_PIG
DE: PIG MYELOID
ANTIBACTERIAL PEPTIDE (PMAP-36).

ID: PMAP37PRC_PIG
DE: PIG MYELOID
ANTIBACTERIAL PEPTIDE
PRECURSOR (PMAP-37, MP37)
(CATHELICIDIN)

ID: PMAP37_PIG
DE: PIG MYELOID
ANTIBACTERIAL PEPTIDE (PMAP-37).

ID: PN1_PENVA
DE: PENAEIDIN-1 (P1),
CRUSTACEAN DEFENCE PEPTIDE

ID: PN2_PENVA
DE: PENAEIDIN-2 PRECURSOR (P2),
CRUSTACEAN DEFENCE PEPTIDE

ID: PN3A_PENVA
DE: PENAEIDIN-3A PRECURSOR
(P3-A), CRUSTACEAN DEFENCE
PEPTIDE

ID: PN3B_PENVA
DE: PENAEIDIN-3B PRECURSOR
(P3-B), CRUSTACEAN DEFENCE
PEPTIDE

ID: PN3C_PENVA
DE: PENAEIDIN-3C PRECURSOR
(P3-C), CRUSTACEAN DEFENCE
PEPTIDE

ID: PNAMP_PHANI
DE: ANTIMICROBIAL PEPTIDE PN-
AMP (PN-AMP1/PN-AMP2), PLANT
DEFENCE PEPTIDE

ID: PP1_PHETS
DE: ANTIMICROBIAL-LIKE
PEPTIDE PP-1.

ID: PPM1_LIMPO
DE: POLYPHEMUSIN I;
CHELICERATE ANTIMICROBIAL
PEPTIDE

ID: PPM2_LIMPO
DE: POLYPHEMUSIN II;
CHELICERATE ANTIMICROBIAL
PEPTIDE

ID: PR39PRC_PIG
DE: ANTIBACTERIAL PEPTIDE PR-
39 PRECURSOR (CATHELICIDIN).

ID: PR39_PIG
DE: ANTIBACTERIAL PEPTIDE PR-
39.

ID: PSE1_PSEPA
DE: PSEUDIN-1

ID: PSE2_PSEPA
DE: PSEUDIN-2

ID: PSE3_PSEPA
DE: PSEUDIN-3

ID: PSE4_PSEPA
DE: PSEUDIN-4

ID: PSPB_HUMAN

DE: PULMONARY-SURFACTANT
PROTEIN).

ID: PTRP_PIG
DE: FROM CLONE C6/C12
(CATHELICIDIN).

ID: PUIA_WHEAT
DE: PUROINDOLINE-A
PRECURSOR; PLANT DEFENCE
PROTEIN

ID: PUIB_WHEAT
DE: PUROINDOLINE-B
PRECURSOR.

ID: PYLA_XENLA
DE: PYLA/PGLA PRECURSOR.

ID: PYRR_PYRAP
DE: PYRRHOCORICIN; INSECT
DEFENCE PEPTIDE

ID: RGSNA_RANRU
DE: RUGOSIN A.

ID: RGSNB_RANRU
DE: RUGOSIN B.

ID: RGSNC_RANRU
DE: RUGOSIN C.

ID: RHIC_ORYRH
DE: RHINOCEROSIN PRECURSOR;
INSECT DEFENCE PEPTIDE,
COLEOPTERICINE

ID: RK1_RABIT
DE: RABIT KIDNEY
CORTICOSTATI/DEFENSIN-LIKE
PEPTIDE RK-1

ID: RL37_MACMU
DE: RL-37.

ID: RLXN_RANCA
DE: RANALEXIN PRECURSOR.

ID: RNX1G_RANGR
DE: RANALEXIN-1G

ID: RT1GA_RANGR
DE: RANATUERIN-1GA

ID: RT1GB_RANGR
DE: RANATUERIN-1GB

ID: RT2B_RANBE
DE: RANATUERIN-2B.

ID: RT2GB_RANGR
DE: RANATUERIN-2GB

ID: RT2LA_RANLU
DE: RANATUERIN-2LA.

ID: RT2LB_RANLU
DE: RANATUERIN-2LB.

ID: RT2TRA_RANTA
DE: RANATUERIN-2TRA.

FIGURE 7 (cont.)

ID: RT4_RANCA
DE: RANATUERIN 4.

ID: SALC_ONCMY
DE: SALMOCIDIN (FRAGMENT).

ID: SAPBRK_SARPE
DE: SAPECIN B 7R-17K FRAGMENT;
INSECT DEFENCE PEPTIDE.

ID: SAPB_SARPE
DE: SAPECIN B, INSECT DEFENSIN.

ID: SAPC_SARPE
DE: SAPECIN C, INSECT DEFENSIN.

ID: SAPE_SARPE
DE: SAPECIN PRECURSOR, INSECT
DEFENSIN.

ID: SCAR_ORHYR
DE: SCARABAECIN. INSECT
DEFENCE PEPTIDE

ID: SCRP_PANIM
DE: SCORPINE PRECURSOR.

ID: SECP_APIME
DE: SECAPIN, INSECT VENOM
COMPONENT

ID: SHEP_CAPBU
DE: ANTIMICROBIAL PEPTIDE
SHEP-GRP. SHEPHERIN-1

ID: SILU_RHIPU
DE: SILLUCIN; FUNGUS
ANTIMICROBIAL PEPTIDE

ID: SLN_BOVIN
DE: SECRETOLYTIN;
SECRETOGRANIN
I(CHROMOGRANIN
B)ANTIBACTERIAL FRAGMENT

ID: SMAP29PRC_SHEEP
DE: SHEEP MYELOID
ANTIBACTERIAL PEPTIDE
PRECURSOR (SMAP-29,
MP29)(CATHELICIDIN) CATHELIN-
RELATED PEPTIDE SC5

ID: SMAP29_SHEEP
DE: SHEEP MYELOID
ANTIBACTERIAL PEPTIDE, SC5,
SMAP-29.

ID: SMAP34_SHEEP
DE: SHEEP MYELOID
ANTIMICROBIAL PEPTIDE
PRECURSOR.(MAP34)(CATHELICID
IN)

ID: SNA1_SOLTU
DE: SNAKIN-1 (FRAGMENT).
PLANT DEFENCE PEPTIDE

ID: SNA2_SOLTU
DE: SNAKIN2 PRECURSOR. STSN2.

ID: SPAMP1_PINSY
DE: ANTIMICROBIAL PEPTIDE
PRECURSORs (SP-AMP1 to SP-
AMP3); PLANT DEFENCE PEPTIDE;

ID: SPD1A_HYACE
DE: SPODPSIN 1A, INSECT
DEFENCE PEPTIDE

ID: SPD1B_HYACE
DE: SPODPSIN 1B, INSECT
DEFENCE PEPTIDE

ID: SPF1_BOVIN
DE: SEMINAL PLASMIN
FRAGMENT(SPF), (CALTRIN
FRAGMENT).

ID: SPF2_BOVIN
DE: SEMINAL PLASMIN
FRAGMENT 2(SPF). (CALTRIN
FRAGMENT).

ID: SPIG_PSEUS
DE: SPINGERIN/SPINIGERIN.

ID: SPYY_PHYBI
DE: SKIN POLYPEPTIDE YY
(NEUROPEPTIDE/PANCREATIC
POLYPEPTIDE YY ANALOGUE)

ID: SR1A_SARPE
DE: SARCOTOXIN IA PRECURSOR.

ID: SR1B_SARPE
DE: SARCOTOXIN IB PRECURSOR,
INSECT DEFENCE PEPTIDE

ID: SR1C_SARPE
DE: SARCOTOXIN IC, INSECT
DEFENCE PEPTIDE

ID: SR1D_SARPE
DE: SARCOTOXIN ID, INSECT
DEFENCE PEPTIDE

ID: SR21_SARPE
DE: SARCOTOXIN II-1 PRECURSOR,
INSECT DEFENCE PEPTIDE

ID: SR22_SARPE
DE: SARCOTOXIN II-2 PRECURSOR,
INSECT DEFENCE PEPTIDE

ID: SR23_SARPE
DE: SARCOTOXIN II-3 PRECURSOR,
INSECT DEFENCE PROTEIN

ID: SR2_SARPE
DE: SARCOTOXIN IIA PRECURSOR.
INSECT DEFENCE PEPTIDE

ID: STOX_STOMA
DE: STOMOXIN.

ID: STYA_STYCL

DE: STYELIN A (FRAGMENT),
TUNICATE DEFENCE PEPTIDE

ID: STYB_STYCL
DE: STYELIN B (FRAGMENT),
TUNICATE DEFENCE PEPTIDE

ID: STYC_STYCL
DE: STYELIN C; TUNICATE
DEFENCE PEPTIDE

ID: STYD_STYCL
DE: STYELIN D; TUNICATE
DEFENCE PEPTIDE

ID: TAC1_TACGI
DE: TACHYPLESIN I;
CHELICERATE DEFENCE PEPTIDE

ID: TAC1_TACTR
DE: TACHYPLESIN I PRECURSOR;
CHELICERATE ANTIMICROBIAL
PEPTIDE

ID: TAC2_TACTR
DE: TACHYPLESIN II PRECURSOR;
CHELICERATE DEFENCE PEPTIDE

ID: TAC3_TACGI
DE: TACHYPLESIN III;
CHELICERATE DEFENCE PEPTIDE

ID: TACA1_TACTR
DE: TACHYSTATIN A
(CHELICERATE ANTIMICROBIAL
PEPTIDE)

ID: TACB_TACTR
DE: TACHYSTATIN B
(CHELICERATE ANTIMICROBIAL
PEPTIDE)

ID: TACC_TACTR
DE: TACHYSTATIN C
(CHELICERATE ANTIMICROBIAL
PEPTIDE)

ID: TACN_TACTR
DE: TACHYCITIN; CHELICERATE
DEFENCE PEPTIDE

ID: TAP_BOVIN
DE: TRACHEAL ANTIMICROBIAL
PEPTIDE PRECURSOR (TAP),
BOVINE BETA-DEFENSIN.

ID: TCBI_TRILO
DE: TRICHOLONGIN BI AND BII.

ID: TDEF1A_MACMU
DE: THETA DEFENSIN-1, SUBUNIT
A PRECURSOR (RTD-1).

ID: TDEF1B_MACMU
DE: THETA DEFENSIN-1, SUBUNIT
B PRECURSOR (RTD-1).

ID: TDEF1_MACMU
DE: RHESUS THETA DEFENSIN 1;
RTD-1 CYCLIC DEFENSE PEPTIDE

FIGURE 7 (cont.)

ID: TEJA_RANJA
DE: TEMPORIN-1JA, FROG ANTIMICROBIAL PEPTIDE.

ID: TEN3_TENMO
DE: TENECIN 3 PRECURSOR. INSECT DEFENCE PEPTIDE

ID: TERN_PSEUS
DE: TERMICIN.

ID: THAN_PODMA
DE: THANATIN; INSECT DEFENCE PEPTIDE.

ID: THHR_HORVU
DE: ANTIFUNGAL PROTEIN R (FRAGMENT), PLANT DEFENCE PEPTIDE

ID: THHS_HORVU
DE: ANTIFUNGAL PROTEIN S (FRAGMENT), PLANT DEFENCE PEPTIDE

ID: TIN1_HOPTI
DE: TIGERININ-1.

ID: TIN2_HOPTI
DE: TIGERININ-2.

ID: TIN3_HOPTI
DE: TIGERININ-3.

ID: TIN4_HOPTI
DE: TIGERININ-4.

ID: TMP10B_RANOR
DE: BREVININ-20B.

ID: TMP10C_RANOR
DE: TEMPORIN-10C.

ID: TMP10D_RANOR
DE: TEMPORIN-10D.

ID: TMP1GA_RANGR
DE: TEMPORIN-1GA

ID: TMP1LA_RANLU
DE: TEMPORIN-1LA.

ID: TMP1LB_RANLU
DE: TEMPORIN-1LB.

ID: TMP1LC_RANLU
DE: TEMPORIN-1LC.

ID: TMP1_RATAG
DE: TEMPORIN

ID: TMPA_RANTE
DE: TEMPORIN A

ID: TMPB_RANTE
DE: TEMPORIN B

ID: TMPL_RANTE
DE: TEMPORIN L.

ID: TPM1_LYCES
DE: OSMOTIN-LIKE PROTEIN TPM-1 PRECURSOR (FRAGMENT), PLANT DEFENCE PEPTIDE

ID: TRFE_CHICK
DE: OVOTRANSFERRIN PRECURSOR (CONALBUMIN) (ALLERGEN GAL D 3) (GAL D III).

ID: UP21_UPEIN
DE: UPERIN 2.1.

ID: UP22_UPEIN
DE: UPERIN 2.2.

ID: UP23_UPEIN
DE: UPERIN 2.3.

ID: UP24_UPEIN
DE: UPERIN 2.4.

ID: UP25_UPEIN
DE: UPERIN 2.5.

ID: UP26_UPEMJ
DE: UPERIN 2.6.

ID: UP27_UPEMJ
DE: UPERIN 2.7.

ID: UP28_UPEMJ
DE: UPERIN 2.8.

ID: UP36_UPEMJ
DE: UPERIN 3.6.

ID: UP3_UPEIN
DE: UPERINS 3.1, 3.2 & 3.3

ID: UP3_UPEMJ
DE: UPERINS 3.4, 3.5. AND 3.7

ID: UP41_UPEIN
DE: UPERIN 4.1.

ID: UP6_UPEIN
DE: UPERIN 6.1. AND 6.2.

ID: UP71_LITEW
DE: UPERIN 7.1 [CONTAINS: UPERIN 7.1.1].

ID: VIC12_MACIN
DE: VICILIN PRECURSOR (MIAMP2), PLANT ANTIMICROBIAL PROTEIN

ID: VIC3_MACIN
DE: VICILIN PRECURSOR (MIAMP2) PLANT ANTIMICROBIAL PROTEIN

ID: VIP_PIG
DE: (VIP) (FRAGMENT).

ID: VIRE_HELVI
DE: VIRESCEIN.

ID: VSTN_BOVIN
DE: PANCREASTATIN; WE-14; CATESTATIN].

ID: XENO_XENLA
DE: XENOPSIN/XPF PRECURSOR. AMPHIBIAN DEFENCE PEPTIDE

ID: XT1_XENTR
DE: ANTIMICROBIAL PEPTIDE 1 (XT-1).

ID: XT2_XENTR
DE: ANTIMICROBIAL PEPTIDE 2 (XT-2).

ID: XT3_XENTR
DE: ANTIMICROBIAL PEPTIDE 3 (XT-3) (LEVITIDE-LIKE PEPTIDE).

ID: XT4_XENTR
DE: ANTIMICROBIAL PEPTIDE 4 (XT-4).

ID: XT5_XENTR
DE: ANTIMICROBIAL PEPTIDE 5 (XT-5) (PGLA-LIKE PEPTIDE).

ID: XT6_XENTR
DE: ANTIMICROBIAL PEPTIDE 6 (XT-6).

ID: XT7_XENTR
DE: ANTIMICROBIAL PEPTIDE 7 (XT-7).

ID: ZEAM_MAIZE
DE: ZEAMATIN PRECURSOR; PLANT DEFENCE PROTEIN

METHODS AND COMPOSITIONS FOR WOUND HEALING

This application claims the benefit of U.S. Prov. Appl. 61/024,725, filed Jan. 30, 2008, the entire contents of which are incorporated herein by reference.

FIELD OF THE INVENTION

The present invention relates to methods and compositions for the modulation of wound healing. In particular, the present invention relates to promoting and enhancing wound healing by changing the intrinsic chemical composition and/or physical features of the wound bed.

BACKGROUND OF THE INVENTION

The primary goal in the treatment of wounds is to achieve wound closure. Open cutaneous wounds represent one major category of wounds and include burn wounds, wounds resulting from chemical (especially alkali) burns, wounds from physical trauma, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis, v) epithelialization, and vi) wound contraction. Wound healing is impaired when these components, either individually or as a whole, do not function properly. Numerous factors can affect wound healing, including but not limited to malnutrition, systemic debility due to a variety of causes, wound infection, local lack of progenitor cells, local and/or systemic pharmacological agents (e.g., numerous chemotherapeutic agents, actinomycin and steroids), repeated local trauma, diabetes and other endocrine/metabolic diseases (e.g., Cushing's disease), and advanced age (Hunt and Goodson, 1988, Current Surgical Diagnosis & Treatment, Appleton & Lange, pp. 86-98). Additionally, wounds that are extensive in size, regardless of the initiating cause, present special challenges due to the large surface area that must be re-epithelialized to re-establish surface integrity.

Delayed wound healing causes substantial morbidity in subjects with diabetes. Diabetes mellitus is a chronic disorder of glucose metabolism and homeostasis that damages many organs. It is the eighth leading cause of death in the United States (Harris et al., 1987, Diabetes 36:523). In persons with diabetes, vascular disease, neuropathy, infections, and recurrent trauma predispose the extremities, especially the foot, to pathologic changes. These pathological changes can ultimately lead to chronic ulceration, which may necessitate amputation. Chronic wounds and wounds with pathological or dysregulated healing represent a major health burden and drain on health care resources. Chronic wounds have major impacts on the physical and mental health, productivity, morbidity, mortality and cost of care for affected individuals. The most common types of chronic wounds are caused by systemic diseases such as diabetes, vascular problems such as venous hypertension and by immobility-induced pressure sores; accounting for 70% of all chronic wounds. Statistics on the prevalence of chronic wounds varies, however studies report that 0.2% to 1% of the population suffer from venous ulcers, 0.5% from pressure ulcers, and 5% to 10% of people with diabetes experience neuropathic ulcers. The economic impact of chronic wounds for these conditions alone in the United States has been estimated to be well over $15 billion, annually. With the population growing older, cases of diabetes mellitus will increase as will the magnitude of the problem associated with chronic wounds in these patients.

Normal wound healing is an enormously complex process involving the coordinated interplay between fibroblasts, vascular cells, extracellular matrix and epithelial cells to result in a seamless progression through an inflammatory reaction, wound repair, contracture and coverage by an epithelial barrier. However, in many patients, due to either the local wound environment or systemic disease or other factors, the wound healing processes can become asynchronous (i.e., loss of connectivity with triggering mechanisms associated with prior cellular events) and are unable to progress to closure, resulting in a chronic ulcer.

Wounds that do not readily heal can cause the subject considerable physical, emotional, and social distress as well as great financial expense (Richey et al., 1989, Annals of Plastic Surgery 23:159). Indeed, wounds that fail to heal properly and become infected may require excision of the affected tissue. A number of treatment modalities have been developed as scientists' basic understanding of wounds and wound healing mechanisms has progressed.

The most commonly used conventional modality to assist in wound healing involves the use of wound dressings. In the 1960s, a major breakthrough in wound care occurred when it was discovered that wound healing with moist, occlusive dressings was, generally speaking, more effective than the use of dry, non-occlusive dressings (Winter, 1962, Nature 193:293). Today, numerous types of dressings are routinely used, including films (e.g., polyurethane films), hydrocolloids (hydrophilic colloidal particles bound to polyurethane foam), hydrogels (crosslinked polymers containing about at least 60% water), foams (hydrophilic or hydrophobic), calcium alginates (nonwoven composites of fibers from calcium alginate), and cellophane (cellulose with a plasticizer) (Kannon and Garrett, 1995, Dermatol. Surg. 21:583; Davies, 1983, Burns 10:94). Unfortunately, certain types of wounds (e.g., diabetic ulcers, pressure sores) and the wounds of certain subjects (e.g., recipients of exogenous corticosteroids) do not heal in a timely manner (or at all) with the use of such dressings.

Several pharmaceutical modalities have also been utilized in an attempt to improve wound healing. For example, some practitioners have utilized treatment regimens involving zinc sulfate. However, the efficacy of these regimens has been primarily attributed to their reversal of the effects of subnormal serum zinc levels (e.g., decreased host resistance and altered intracellular bactericidal activity) (Riley, 1981, Am. Fam. Physician 24:107). While other vitamin and mineral deficiencies have also been associated with decreased wound healing (e.g., deficiencies of vitamins A, C and D; and calcium, magnesium, copper, and iron), there is no strong evidence that increasing the serum levels of these substances above their normal levels actually enhances wound healing. Thus, except in very limited circumstances, the promotion of wound healing with these agents has met with little success.

Current clinical approaches used to promote healing in dysregulated wounds include protection of the wound bed from mechanical trauma (e.g. splinting, bandaging), meticulous control of surface microbial burden (antibiotics, antimicrobial peptides, bacteriophages, antiseptics and other antimicrobial compounds that broadly inhibit wound pathogens (e.g. silver sulfadiazine) combined with topical application of soluble cytoactive factors (e.g. growth factors exemplified by but not limited to epidermal growth factor-EGF, exogenous extracellular matrix constituents such as fibronectin), surgical excision of the wound margin or entire bed and surgical placement of tissue flaps and/or autografts, allografts and xenografts. All of these approaches fall short of promoting optimal healing conditions in many of the most challenging wounds. It is likely that a major contributing factor to the failure of these traditional approaches is the fact that they do not alter the intrinsic chemistry/structure of the wound bed itself that has been shown in many cases to contribute significantly to their persistence. Additionally, the historical use of a single factor or set of factors to treat all wounds often falls short due to the great heterogeneity found in wound beds themselves and the complex environment of the wound itself containing a community of signaling molecules that frequently modulate the activity of individual molecules.

The complex nature of pathologic wounds, and the lack of significant clinical progress based on current therapies, indicates the urgent need for new and unconventional approaches. What is needed is a safe, effective, and interactive means for enhancing the healing of chronic and severe wounds. The methods should be adaptable without regard to the type of wound, or the nature of the patient population, to which the subject belongs.

SUMMARY OF THE INVENTION

The present invention relates to methods and compositions for the modulation of wound healing. In particular, the present invention relates to promoting and enhancing wound healing by changing the intrinsic chemical composition and/or physical attributes of the wound bed. Accordingly, in some embodiments the present invention provides formulations that alter the physical attributes (compliance, topography, charge), as well as cross-linker covalent modification molecules to attach and deliver antimicrobial compounds as well as extracellular matrices and other scaffolds and cytoactive agents to a wound. In addition, the present invention provides methods and compositions utilizing oppositely charged polyelectrolytes to form a polyelectrolyte layer on a wound surface. The invention further relates to the incorporation of non-charged polymers into the wound bed via interactions such as but not limited to hydrogen bonding. The scope of the invention includes incorporation of nanoparticles and microparticles into the wound bed to engineer the physical characteristics and chemical composition of the wound bed. The invention further relates to incorporating wound active agents into a polyelectrolyte layer, nanoparticle or microparticle for delivery to a wound. In some embodiments, the present invention provides formulations that promote a favorable and stable pH, surface charge, surface energy, osmotic environment, surface functionalities that enhance galvano- and magneto-positive effects on wound healing, supply of nitric oxide, provide energy sources for cells and/or provide a balance of MMP/other peptidase/protease activity.

In one embodiment, the compositions and methods of the present invention provide approaches to promote healing in pathologic wounds by altering the surface chemistry and structure of the pathologic wound bed itself so as to ultimately enable differential modulation of key cellular elements customizable to the specific patient's health wound type and anatomic location in a subject.

In one embodiment, the present invention provides for the covalent immobilization of factors to the wound bed. In some embodiments, the present invention provides methods of treatment, comprising providing a subject having a wound, at least one covalent modification agent and at least one wound active agent, and contacting the wound with the at least one covalent modification agent and the at least one wound active agent under conditions such that the at least one wound active agent is covalently attached to the wound. In some embodiments, the subject is a human. In other embodiments, the subject is a non-human vertebrate. In some embodiments, the at least one covalent modification agent is a homobifunctional cross-linker. In other embodiments, the at least one covalent modification agent is a heterobifunctional cross-linker. For example, in some embodiments, the homobifunctional cross-linker is an N-hydroxysuccinimidyl ester (e.g., including, but not limited to, disuccinimidyl ester, dithiobis(succinimidylpropionate), 3,3'-dithiobis(sulfosuccinimidylpropionate), disuccinimidyl suberate, bis(sulfosuccinimidyl)suberate, disuccinimidyl tartarate, disulfosuccinimidyl tartarate, bis[2-(succinimidyloxycarbonyloxy)ethyl]sulfone, bis[2-(sulfosuccinimidooxycarbonyloxy)ethyl]sulfone, ethylene glycol-bis(succinimidylsuccinate), ethylene glycolbis (sulfosuccinimidylsuccinate), disuccinimidyl glutarate, and N,N'-disuccinimidylcarbonate). In some embodiments, the homobifunctional cross-linker is at a concentration between 1 nanomolar and 10 millimolar. In some preferred embodiments, the homobifunctional cross-linker is at a concentration between 10 micromolar and 1 millimolar. In other embodiments, the at least one covalent modification agent is a heterobifunctional cross-linker (e.g., including, but not limited to, N-succinimidyl 3-(2-pyridyldithio)propionate, succinimidyl 6-(3-[2-pyridyldithio]-propionamido)hexanoate, sulfosuccinimidyl 6-(3'-[2-pyridyldithio]-propionamido) hexanoate, succinimidyloxycarbonyl-α-methyl-α-(2-pyridyldithio)toluene, sulfosuccinimidyl-6-[α-methyl-α-(2-pyridyldithio)toluamido]hexanoate, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxy-sulfosuccinimide ester, N-succinimidyl(4-iodoacetyl)aminobenzoate, sulfosuccinimidyl(4-iodoacetyl)aminobenzoate, succinimidyl-4-(p-maleimidophenyl)butyrate, sulfosuccinimidyl-4-(p-maleimidophenyl)butyrate, N-(γ-maleimidobutyryloxy) succinimide ester, N-(γ-maleimidobutyryloxy) sulfosuccinimide ester, succinimidyl 6-((iodoacetyl)amino) hexanoate, succinimidyl 6-(6-(((4-iodoacetyl)amino) hexanoyl)amino)hexanoate, succinimidyl 4-(((iodoacetyl) amino)methyl)cyclohexane-1-carboxylate, succinimidyl 6-((((4-iodoacetyl)amino)methyl)cyclohexane-1-carbonyl) amino)-hexanoate, and p-nitrophenyl iodoacetate). In some embodiments, the heterobifunctional cross-linker is modified with functional groups, rendering it soluble in aqueous solvents for delivery as an aqueous solution. Furthermore, in some embodiments, the aqueous solution contains additives (e.g., including, but not limited to, surfactants and block copolymers). In other embodiments, a multiplicity of heterobifunctional cross-linkers can be attached to a molecule, polymer or particle to serve as the cross-linking agent. In other embodiments, the heterobifunctional cross-linker is dissolved in an organic solvent (e.g., including, but not limited to, dimethyl sulfoxide). In some embodiments, the at least one wound active agent includes, but is not limited to, trophic factors, extracellular matrices, enzymes, enzyme inhibitors, defensins, polypeptides, anti-infective agents, buffering agents, vitamins and minerals, analgesics, anticoagulants, coagulation factors, anti-inflammatory agents, vasoconstrictors, vasodilators, diuretics, and anti-cancer agents. In some embodiments, the at least one wound active agent contains one or more free —SH groups.

The present invention also provides a kit for treating a subject having a wound, comprising at least one covalent modification agent, at least one wound active agent, and instructions for using the kit to covalently link the at least one wound active agent to the wound. In some embodiments, the at least one covalent modification agent is a homobifunctional cross-linker. In some embodiments, the homobifunctional cross-linker is an N-hydroxysuccinimidyl ester (e.g., including, but not limited to, disuccinimidyl ester, dithiobis(succinimidylpropionate), 3,3'-dithiobis(sulfosuccinimidylpropionate), disuccinimidyl suberate, bis(sulfosuccinimidyl) suberate, disuccinimidyl tartarate, disulfosuccinimidyl tartarate, bis[2-(succinimidyloxycarbonyloxy)ethyl]sulfone, bis[2-(sulfosuccinimidooxycarbonyloxy)ethyl]sulfone, ethylene glycolbis(succinimidylsuccinate), ethylene glycolbis(sulfosuccinimidylsuccinate), disuccinimidyl glutarate, and N,N'-disuccinimidylcarbonate). In some embodiments, the at least one covalent modification agent is a heterobifunctional cross-linker (e.g., including, but not limited to, N-succinimidyl 3-(2-pyridyldithio)propionate, succinimidyl 6-(3-[2-pyridyldithio]-propionamido)hexanoate, sulfosuccinimidyl 6-(3'-[2-pyridyldithio]-propionamido)hexanoate, succinimidyloxycarbonyl-α-methyl-α-(2-pyridyldithio)toluene, sulfosuccinimidyl-6-[α-methyl-α-(2-pyridyldithio)toluamido]hexanoate, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxysulfosuccinimide ester, N-succinimidyl(4-iodoacetyl)aminobenzoate, sulfo-succinimidyl(4-iodoacetyl)aminobenzoate, succinimidyl-4-(p-maleimidophenyl)butyrate, sulfosuccinimidyl-4-(p-maleimidophenyl)butyrate, N-(γ-maleimidobutyryloxy) succinimide ester, N-(γ-maleimidobutyryloxy) sulfosuccinimide ester, succinimidyl 6-((iodoacetyl)amino) hexanoate, succinimidyl 6-(6-(((4-iodoacetyl)amino)hexanoyl)amino)hexanoate, succinimidyl 4-(((iodoacetyl) amino)methyl)cyclohexane-1-carboxylate, succinimidyl 6-((((4-iodoacetyl)amino)methyl)cyclohexane-1-carbonyl) amino)-hexanoate, and p-nitrophenyl iodoacetate). In some embodiments, the at least one wound active agent includes, but is not limited to, trophic factors, including polypeptide growth factors, neuropeptides, neurotrophins, extracellular matrices and their individual native constituents (exemplified by but not limited to laminin, fibronectin, vitronectin, collagens, also select amino acid sequences found in these proteins known to promote cell behaviors favorable to wound healing, e.g., integrin binding sequences exemplified by but not limited to RGD, EILDV, VCAM-1 and their recombined or synthetic analogs, enzymes, enzyme inhibitors, and polypeptides), antimicrobial peptides (exemplified by but not limited to defensins, magainins, cathelocidins, bactenicin) anti-infective agents including silver containing compounds, buffering agents, vitamins and minerals, compounds that promote generation/stabilization of nitric oxide, energy sources for cells, analgesics, anticoagulants, coagulation factors, anti-inflammatory agents, vasoconstrictors, vasodilators, diuretics, and anti-cancer agents. In other embodiments the kits include small interfering RNAs (siRNAs—also referred to as micro RNAs) that are capable of promoting cellular behaviors conducive to the wound healing process. In other embodiments, the kits include compounds that promote/stabilize a favorable pH, osmotic environment, surface energy, surface charge, surface functionalities that enhance galvano- and magneto-positive effects on wound healing, or balance of MMP/other peptidase/protease activity.

In some embodiments, the present invention provides a method of treatment, comprising providing a subject having a wound, at least one cationic polyelectrolyte, at least one anionic polyelectrolyte, at least one covalent modification agent, and at least one wound active agent, and contacting the wound with the at least one cationic and the at least one anionic polyelectrolytes, the at least one covalent modification agent, and the at least one wound active agent so that the at least one wound active agent is covalently linked to the wound by incorporation into a polyelectrolyte layer formed by the at least one cationic and the at least one anionic polyelectrolytes. In some preferred embodiments, the polyelectrolytes are sequentially and repeatedly layered on the wound, then the at least one covalent modification agent and the at least one wound active agent are added. In some embodiments, the at least one cationic polyelectrolyte (e.g., including, but not limited to, poly(L-lysine), poly(ethylene imine), and poly(allylamine hydrochloride and dendrimers and multi-armed polymers that present multiple amine groups) is the top layer of the polyelectrolyte layers. Furthermore, in some embodiments, the at least one cationic polyelectrolyte harbors a primary amine group which allows attachment of the at least one covalent modification agent to the at least one cationic polyelectrolyte. For example, in some preferred embodiments, the at least one cationic polyelectrolyte is polylysine and the at least one anionic polyelectrolyte is polyglutamic acid. In some embodiments, the at least one anionic polyelectrolyte (e.g., including, but not limited to, poly(L-glutamic acid), poly(sodium 4-styrenesulfonate), poly(acrylic acid), poly(maleic acid-co-propylene), hyaluronic acid, chondroitin, and poly(vinyl sulfate)) is the top layer of the polyelectrolyte layers. In a preferred embodiment, the at least one anionic polyelectrolyte is polyglutamic acid. In some embodiments, the at least one covalent modification agent is a heterobifunctional cross-linker (e.g., including, but not limited to, N-succinimidyl 3-(2-pyridyldithio)propionate, succinimidyl 6-(3-[2-pyridyldithio]-propionamido)hexanoate, sulfosuccinimidyl 6-(3'-[2-pyridyldithio]-propionamido)hexanoate, succinimidyloxycarbonyl-α-methyl-α-(2-pyridyldithio) toluene, sulfosuccinimidyl-6-[α-methyl-α-(2-pyridyldithio) toluamido]hexanoate, succinimidyl 4-(N-maleimidomethyl) cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxy-sulfosuccinimide ester, N-succinimidyl(4-iodoacetyl)aminobenzoate, sulfo-succinimidyl(4-iodoacetyl)aminobenzoate, succinimidyl-4-(p-maleimidophenyl)butyrate, sulfosuccinimidyl-4-(p-maleimidophenyl)butyrate, N-(γ-maleimidobutyryloxy) succinimide ester, N-(γ-maleimidobutyryloxy) sulfosuccinimide ester, succinimidyl 6-((iodoacetyl)amino) hexanoate, succinimidyl 6-(6-(((4-iodoacetyl)amino)hexanoyl)amino)hexanoate, succinimidyl 4-(((iodoacetyl) amino)methyl)cyclohexane-1-carboxylate, succinimidyl 6-((((4-iodoacetyl)amino)methyl)cyclohexane-1-carbonyl) amino)-hexanoate, and p-nitrophenyl iodoacetate). In some embodiments, the at least one covalent modification agent is a homobifunctional cross-linker. In some embodiments, the homobifunctional cross-linker is an N-hydroxysuccinimidyl ester (e.g., including, but not limited to, disuccinimidyl ester, dithiobis(succinimidylpropionate), 3,3'-dithiobis(sulfosuccinimidylpropionate), disuccinimidyl suberate, bis(sulfosuccinimidyl)suberate, disuccinimidyl tartarate, disulfosuccinimidyl tartarate, bis[2-(succinimidyloxycarbonyloxy)ethyl] sulfone, bis[2-(sulfosuccinimidooxycarbonyloxy)ethyl] sulfone, ethylene glycolbis(succinimidylsuccinate), ethylene glycolbis(sulfosuccinimidylsuccinate), disuccinimidyl glutarate, and N,N'-disuccinimidylcarbonate). In some embodiments, the at least one covalent modification agent can be at a concentration between 1 nanomolar and 10 millimolar. In some preferred embodiments, the at least one covalent modification agent is at a concentration between 10 micromolar to 1 millimolar. In some preferred embodiments, the at least one covalent modification agent is bis(sulfosuccinimidyl)suberate (for example, in aqueous solution at a concentration between 1 nM and 10 mM). In some embodiments, the at least one covalent modification agent comprises N-hydroxysuccinimidyl ester. In some preferred embodiments, the at least one wound active agent contains the peptide sequence gly-arg-gly-asp-ser-pro-lys.

In some embodiments, a first at least one anionic or cationic polyelectrolyte is contacted with the at least one covalent modification agent and the at least one wound active agent before contacting with the wound bed and oppositely charged at least one cationic or anionic polyelectrolyte. In some preferred embodiments, the first at least one anionic polyelectrolyte is polyglutamic acid, the at least one covalent modification agent is N-hydroxysuccinimidyl ester, and the at least one wound active agent contains a primary amine (e.g., including, but not limited to, the peptide sequence gly-arg-gly-asp-ser-pro-lys). In some preferred embodiments, the first at least one cationic polyelectrolyte is polylysine, the at least one covalent modification agent is N-succinimidyl 3-(2-pyridyldithio)propionate, and the at least one wound active agent contains the peptide sequence gly-arg-gly-asp-ser-pro-cys.

The present invention further provides kits for treating a subject having a wound, comprising at least one cationic polyelectrolyte, at least one anionic polyelectrolyte, at least one covalent modification agent, at least one wound active agent; and instructions for using the kit to covalently link the at least one wound active agent to the wound by incorporation into a polyelectrolyte layer that is formed by the at least one cationic and anionic polyelectrolytes. In some embodiments, the incorporation of the at least one wound active agent is achieved by sequential and repeated layering of the polyelectrolytes, followed by addition of the at least one covalent modification agent and the at least one wound active agent. In other embodiments, a first at least one anionic or cationic polyelectrolyte is contacted with the at least one covalent modification agent and the at least one wound active agent before contacting with the wound bed and oppositely charged at least one cationic or anionic polyelectrolyte. In some embodiments, the at least one cationic polyelectrolyte includes, but is not limited to, poly(L-lysine), poly(ethylene imine), and poly(allylamine hydrochloride). In some embodiments, the at least one anionic polyelectrolyte includes, but is not limited to, poly(L-glutamic acid), poly(sodium 4-styrenesulfonate), poly(acrylic acid), poly(maleic acid-co-propylene), and poly(vinyl sulfate). In some embodiments, the at least one covalent modification agent is a homobifunctional cross-linker. In some embodiments, the homobifunctional cross-linker is an N-hydroxysuccinimidyl ester (e.g., including, but not limited to, disuccinimidyl ester, dithiobis(succinimidylpropionate), 3,3'-dithiobis(sulfosuccinimidylpropionate), disuccinimidyl suberate, bis(sulfosuccinimidyl) suberate, disuccinimidyl tartarate, disulfosuccinimidyl tartarate, bis[2-(succinimidyloxycarbonyloxy)ethyl]sulfone, bis[2-(sulfosuccinimidooxycarbonyloxy)ethyl]sulfone, ethylene glycolbis(succinimidylsuccinate), ethylene glycolbis(sulfosuccinimidylsuccinate), disuccinimidyl glutarate, and N,N'-disuccinimidylcarbonate). In other embodiments, the at least one covalent modification agent is a heterobifunctional cross-linker (e.g., including, but not limited to, N-succinimidyl 3-(2-pyridyldithio)propionate, succinimidyl 6-(3-[2-pyridyldithio]-propionamido)hexanoate, sulfosuccinimidyl 6-(3'-[2-pyridyldithio]-propionamido)hexanoate, succinimidyloxycarbonyl-α-methyl-α-(2-pyridyldithio)toluene, sulfosuccinimidyl-6-[α-methyl-α-(2-pyridyldithio)toluamido] hexanoate, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxy-sulfosuccinimide ester, N-succinimidyl(4-iodoacetyl)aminobenzoate, sulfo-succinimidyl(4-iodoacetyl)aminobenzoate, succinimidyl-4-(p-maleimidophenyl)butyrate, sulfosuccinimidyl-4-(p-maleimidophenyl)butyrate, N-(γ-maleimidobutyryloxy)succinimide ester, N-(γ-maleimidobutyryloxy)sulfosuccinimide ester, succinimidyl 6-((iodoacetyl)amino)hexanoate, succinimidyl 6-(6-(((4-iodoacetyl)amino)hexanoyl)amino)hexanoate, succinimidyl 4-(((iodoacetyl)amino)methyl)cyclohexane-1-carboxylate, succinimidyl 6-((((4-iodoacetyl)amino)methyl)cyclohexane-1-carbonyl)amino)-hexanoate, and p-nitrophenyl iodoacetate). In some embodiments, the at least one wound active agent includes, but is not limited to, trophic factors, extracellular matrices, enzymes, enzyme inhibitors, defensins, polypeptides, anti-infective agents, buffering agents, vitamins and minerals, analgesics, anticoagulants, coagulation factors, anti-inflammatory agents, vasoconstrictors, vasodilators, diuretics, and anti-cancer agents.

The present invention also provides a method of treatment, comprising providing a subject having a wound, at least one cationic polyelectrolyte, at least one anionic polyelectrolyte, at least one DNA delivery agent, and at least one DNA species, and contacting the wound with the at least one cationic polyelectrolyte, the at least one anionic polyelectrolyte, the at least one DNA delivery agent, and the at least one DNA species under conditions such that the at least one DNA species is delivered to the wound. In some preferred embodiments, the at least one DNA species includes, but is not limited to, DNA encoding vascular endothelial growth factor and/or epidermal growth factor. In some preferred embodiments, the at least one cationic polyelectrolyte is polylysine.

The present invention further provides a kit for treating a subject having a wound, comprising: at least one cationic polyelectrolyte, at least one anionic polyelectrolyte, at least one DNA delivery agent, at least one DNA species, and instructions for using the kit to deliver the at least one DNA species to the wound using the at least one DNA delivery agent and a polyelectrolyte layer formed by the at least one cationic and anionic polyelectrolytes.

The present invention also provides a method of treatment, comprising providing a subject having a wound, a cationic and anionic polyelectrolyte mixture, a deprotection agent, at least one covalent modification agent, and at least one wound active agent; contacting the wound with the polyelectrolyte mixture to form a polyelectrolyte layer on the wound; applying the deprotection agent to the polyelectrolyte layer to form a deprotected polyelectrolyte layer; applying the at least one covalent modification agent to the deprotected polyelectrolyte layer to form a modified deprotected polyelectrolyte layer; and applying the at least one wound active agent to the modified deprotected polyelectrolyte layer under conditions such that the at least one wound active agent is covalently attached to the wound. In some preferred embodiments, the anionic and cationic polyelectrolyte mixture is made up of polylactic acid and poly(epsilon-CBZ-L-lysine), blended at an 80:20 ratio. In some embodiments, the deprotection occurs by acid hydrolysis. In some embodiments, the at least one covalent modification agent is SP3. The present invention also provides a composition comprising a deprotected polyelectrolyte, functionalized with at least one covalent modification agent containing an active group that is exposable to at least one wound active agent. In some preferred embodiments, the deprotected polyelectrolyte is comprised of polylactic acid and poly(epsilon-CBZ-L-lysine), blended at an 80:20 ratio. In a preferred embodiment, the at least one covalent modification agent is SP3.

The present invention also provides a method of treatment, comprising providing a subject having a wound, a cationic and anionic polyelectrolyte mixture, a deprotection agent, at least one covalent modification agent, a first polypeptide, and at least one wound active agent linked to a second polypeptide; contacting the wound with the polyelectrolyte mixture to form a polyelectrolyte layer on the wound; applying the deprotection agent to the polyelectrolyte layer to form a deprotected polyelectrolyte layer; applying the at least one covalent modification agent to the deprotected polyelectrolyte layer to form a modified deprotected polyelectrolyte layer; applying the first polypeptide to the modified deprotected polyelectrolyte layer to covalently link the first polypeptide to the modified deprotected polyelectrolyte layer; and applying the at least one wound active agent linked to the second polypeptide to the modified deprotected polyelectrolyte layer covalently linked to the first polypeptide, under conditions such that the at least one wound active agent is attached to the wound by specific protein binding between the first polypeptide and the second polypeptide. In some preferred embodiments, the specific protein binding occurs between biotin and a polypeptide (e.g., including, but not limited to, avidin, neutravidin, and streptavidin). In other preferred embodiments, the specific protein binding occurs between glutathione-S-transferase and glutathione. In yet other preferred embodiments, the specific protein binding occurs between nickel-nitrilotriacetic acid and polyhistidine. In some embodiments, the at least one covalent modification agent is SP3.

The present invention further provides a composition comprising a deprotected polyelectrolyte functionalized with at least one covalent modification agent linked to a first polypeptide that interacts by specific binding with a second polypeptide linked to at least one wound active agent. In some preferred embodiments, the specific binding occurs between biotin and a polypeptide (e.g., including, but not limited to, avidin, neutravidin, and streptavidin). In other preferred embodiments, the specific binding occurs between glutathione-S-transferase and glutathione. In still other preferred embodiments, the specific protein binding occurs between nickel-nitrilotriacetic acid and polyhistidine.

The present invention also provides a method of treatment, comprising providing a subject having a wound, a cationic and anionic polyelectrolyte mixture, a deprotection agent, at least one covalent modification agent, at least one molecule containing an azide group, and at least one wound active agent containing an alkyne group; contacting the wound with the polyelectrolyte mixture to form a polyelectrolyte layer on the wound; applying the deprotection agent to the polyelectrolyte layer to form a deprotected polyelectrolyte layer; applying the at least one covalent modification agent to the deprotected polyelectrolyte layer to form a modified deprotected polyelectrolyte layer; applying the at least one molecule containing an azide group to the modified deprotected polyelectrolyte layer to covalently link the at least one molecule containing an azide group to the modified deprotected polyelectrolyte layer; and applying the at least one wound active agent containing an alkyne group to the modified deprotected polyelectrolyte layer covalently linked to the at least one molecule containing an azide group, so that the at least one wound active agent is attached to the wound by click chemistry. In some preferred embodiments, the at least one molecule containing an azide group has the formula $H_2N$ $(CH_2CH_2O)_2N_3$. In some preferred embodiments, the at least one wound active agent is L-propargylglycine. In some preferred embodiments, the reaction is carried out in the presence of Cu(I).

The present invention further provides a composition comprising a deprotected polyelectrolyte functionalized with at least one covalent modification agent linked to at least one molecule containing an azide group that is attached by click chemistry to at least one wound active agent containing an alkyne group.

The present invention further provides a kit for treating a subject having a wound, comprising a cationic and anionic polyelectrolyte mixture, a deprotection agent, at least one covalent modification agent, at least one wound active agent, and instructions for using the kit to covalently link the at least one wound active agent to the wound by deprotection of the polyelectrolyte mixture contacted to the wound, followed by addition of the at least one covalent modification agent and the at least one wound active agent. In some preferred embodiments, the polyelectrolyte mixture comprises polylactic acid and poly(epsilon-CBZ-L-lysine). In some preferred embodiments, the deprotection agent causes deprotection by acid hydrolysis of the polyelectrolyte mixture. In some preferred embodiments, the at least one covalent modification agent is SP3. In some embodiments, the kit also contains a first and a second polypeptide that interact with each other by specific protein binding. In some preferred embodiments, the first polypeptide is linked to either the at least one covalent modification agent or the at least one wound active agent and the second polypeptide is linked to the other at least one covalent modification agent or the at least one wound active agent. In some preferred embodiments, the first polypeptide is biotin and the second polypeptide is avidin, neutravidin, or streptavidin. In some other preferred embodiments, the first polypeptide is glutathione-S-transferase and the second polypeptide is glutathione. In still other preferred embodiments, the first polypeptide is nickel-nitrilotriacetic acid and the second polypeptide is polyhistidine. In some embodiments, the kit contains at least one molecule containing an azide group that is attached to the polyelectrolyte mixture after deprotection so that at least one wound active agent containing an alkyne group can be attached to the wound by click chemistry.

The present invention further provides a method of treatment, comprising providing a subject having a wound, at least one cationic polyelectrolyte, at least one anionic polyelectrolyte, at least one modifying agent, and at least one wound active agent containing an amino terminal cysteine residue; and contacting the wound with the polyelectrolytes, the at least one modifying agent and the at least one wound active agent so that the at least one wound active agent is attached to the wound by native chemical ligation. In some preferred embodiments, the polyelectrolytes are sequentially and repeatedly layered on the wound. In some embodiments, the at least one anionic polyelectrolyte (e.g., including, but not limited to, polyglutamic acid) is the top layer of the polyelectrolyte layers. In some embodiments, the at least one modifying agents are ethylene dichloride and $HSCH_2Ph$.

The present invention also provides a composition comprising a polyelectrolyte layer that is functionalized with at least one modifying agent that is exposable to native chemical ligation with at least one wound active agent containing an amino terminal cysteine residue.

The present invention also provides a kit for treating a subject having a wound, comprising at least one cationic polyelectrolyte, at least one anionic polyelectrolyte, at least one modifying agent, at least one wound active agent containing an amino terminal cysteine residue, and instructions for using the kit to form a polyelectrolyte layer on the wound, followed by treatment with the at least one modifying agent and attachment of the at least one wound active agent by native chemical ligation. In some preferred embodiments, the at least one anionic polyelectrolyte is polyglutamic acid. In some preferred embodiments, the at least one modifying agents are ethylene dichloride and $HSCH_2Ph$.

In some embodiments, the present invention provides methods of treatment comprising: a) providing a subject having a wound, at least one wound modifying agent, and at least one wound active agent; b) contacting the wound with the at least one wound modification agent to provide a modified wound bed, and c) contacting the modified wound bed with the at least one wound active agent under conditions such that the at least one wound active agent is incorporated into the modified wound bed and healing of the wound is enhanced. In some embodiments, the modified wound bed is modified to present a functionalized surface reactive with the at least one wound active agent. In some embodiments, the wound active agent is applied to the modified wound bed to form a gradient. In some embodiments, the wound modifying agent alters a property of the wound bed selected from the group consisting of compliance, pH, alkalinity, and oxidative or reductive strength, net charge, hydrophilicity, osmotic strength, nanoscale or submicron topographic features, electroconductivity, MMP production, phagocytosis, and transglutaminase activity. In some embodiments, the wound modifying agent is applied to the wound bed by a method selected from the group consisting of stamping, spraying, pumping, painting, smearing and printing. In some embodiments, the at least one wound modification agent is at least one crosslinker. In some embodiments, the at least one crosslinker is selected from the group consisting of a homobifunctional crosslinker, a heterobifunctional cross linker, a hetero- and homo-multifunctional crosslinker, and a photoactivatable crosslinker and combinations thereof. In some embodiments, the heterobifunctional crosslinker comprises an alkyne group. In some embodiments, the wound modifying agent comprises at least one polymer. In some embodiments, the at least one polymer is applied to the wound bed to form a polymer multilayer. In some embodiments, the at least one polymer is selected from the group consisting of a cationic polymer, an anionic polymer, a nonionic polymer an amphoteric polymer and combinations thereof. In some embodiments, the methods further comprise contacting the polymer multilayer with a crosslinker to form a functionalized surface reactive with the at least one wound active agent. In some embodiments, the at least one polymer is a polyelectrolyte multilayer preformed on a support so that the polyelectrolyte multilayer can be transferred from the support to the wound bed to form a modified wound bed. In some embodiments, the support is an elastomeric support. In some embodiments, the polymer multilayer is from 1 nm to 250 nm thick. In some embodiments, the polymer multilayer has a compliance of from 3 to 500 kPa. In some embodiments, the wound modifying agent is selected from the group consisting of nanoparticles and microparticles. In some embodiments, the nano- and microparticles are functionalized. In some embodiments, the functionalized bead is a mesoscopic cross-linker. In some embodiments, the at least one wound active agent is selected from the group consisting of trophic factors, extracellular matrices, enzymes, enzyme inhibitors, defensins, polypeptides, anti-infective agents, buffering agents, vitamins and minerals, analgesics, anticoagulants, coagulation factors, anti-inflammatory agents, vasoconstrictors, vasodilators, diuretics, and anti-cancer agents.

In some embodiments, the present invention provides kits for treating a subject having a wound, comprising: a) at least one wound modification agent, b) at least one wound active agent; and c) instructions for using the kit to treat a wound bed with the at least one wound modification agent to provide a modified wound bed and for incorporating the wound active agent into the modified wound bed. In some embodiments, the at least one wound modification agent is selected from the group consisting of a covalent modifying agent, at least one polyelectrolyte, microparticle, nanoparticle, and combinations thereof.

In some embodiments, the present invention provides methods of treatment comprising: a) providing a subject having a wound, i) a cationic and anionic polyelectrolyte mixture, ii) a deprotection agent, iii) at least one covalent modification agent, iv) at least one molecule containing an azide group or alkyne group, and v) at least one wound active agent containing the other of an azide group or an alkyne group; b) contacting the wound with the polyelectrolyte mixture to form a polyelectrolyte layer on the wound; c) applying the deprotection agent to the polyelectrolyte layer to form a deprotected polyelectrolyte layer; d) applying the at least one covalent modification agent to the deprotected polyelectrolyte layer to form a modified deprotected polyelectrolyte layer; e) applying the at least one molecule containing an azide group or an alkyne group to the modified deprotected polyelectrolyte layer to covalently link the molecule containing an azide or an alkyne group to the modified deprotected polyelectrolyte layer; f) applying the at least one wound active agent containing the other of an azide group or an alkyne group to the modified deprotected polyelectrolyte layer covalently linked to the molecule containing an azide group, under conditions such that the at least one wound active agent is attached to the wound by click chemistry.

In some embodiments, the present invention provides a composition comprising a deprotected polyelectrolyte functionalized with at least one covalent modification agent linked to at least one molecule containing an azide group that is attached by click chemistry to at least one wound active agent containing an alkyne group.

In some embodiments, the present invention provides methods comprising a) providing a subject having a wound, a plurality of functionalized beads and at least one cytoactive factor, b) contacting the at least one cytoactive factor with the at least one functionalized biocompatible bead such that the at least one cytoactive factor is linked to the at least one functionalized biocompatible bead and c) applying the at least one functionalized biocompatible bead linked to the at least one cytoactive factor to a wound bed of the subject.

In some embodiments, the present invention provides methods of treatment comprising: a) providing a subject having a wound, at least one polymer, and at least one wound active agent b) applying the at least one polymer to the wound so that a polymer multilayer is formed on the wound; and c) incorporating the at least one wound active agent into the polymer multilayer during application of the at least one polymer, wherein the at least one wound active agent forms a gradient in the polymer multilayer.

In some embodiments, the present invention provides an article comprising a matrix formed from a biocompatible material, the matrix comprising at least one wound active agent, wherein the matrix is from 1 to 500 nm in thickness and has a compliance of from 3 to 500 kPa. In some embodiments, the matrix is functionalized. In some embodiments, the biocompatible material is selected from the group consisting of proteins and polymers. In some embodiments, the polymers are selected from the group consisting of polyanionic polymers, polycationic polymers, uncharged polymers, and amphoteric polymers and combinations thereof, and wherein the polymers from a multilayer. In some embodiments, the proteins are extracellular matrix proteins selected from the group consisting of laminin, vitronectin, fibronection, keratin, collagen, and combinations thereof. In some embodiments, the matrix is supported by a solid support selected from the group consisting of silicone, siloxane elastomers, latex, nylon, nylon mesh, biological tissue, silk, polyurethane, Teflon, polyvinyl alcohol membranes, and polyethylene oxide membranes. In some embodiments, the at least one wound active agent is distributed on the matrix so that a gradient is formed. In some embodiments, the matrix is at least partially PEGylated. In some embodiments, the present invention provides methods comprising, applying the articles described above to a wound on a subject, wherein the article enhances healing of the wound. In some embodiments, the present invention provides kits comprising the articles described above in a sterile package.

In some embodiments of the present invention, the compositions and methods described above enhance wound healing. The present invention contemplates that wound healing may be enhanced in a variety of ways. In some embodiments, the compositions and methods minimize contracture of the wound as to best favor function and cosmesis. In some embodiments, compositions and methods promote wound contracture to best favor function and cosmesis. In some embodiments, the compositions and methods promote vascularization. In some embodiments, the compositions and methods inhibit vascularization. In some embodiments, the compositions and methods promote fibrosis. In some embodiments, the compositions and methods inhibit fibrosis. In some embodiments, the compositions and methods promote epithelial coverage. In some embodiments, the compositions and methods inhibit epithelial coverage. In some embodiments, the compositions and methods of the present invention modulates one or properties of cells in the wound environment or in the immediate vicinity of the wound. The properties that are modulated, e.g., are increased or decreased, include, but are not limited to adhesion, migration, proliferation, differentiation, extracellular matrix secretion, phagocytosis, MMP activity, contraction, and combinations thereof.

In some embodiments, the present invention provides for the use of any of the compositions described above or elsewhere herein to enhance healing of a wound or modulate one or more properties of cells in the wound environment or in the immediate vicinity of the wound. In some embodiments, the present invention provides for the use of a combination of a wound modifying agent and wound active agent to enhance healing of a wound to enhance healing of a wound or modulate one or more properties of cells in the wound environment or in the immediate vicinity of the wound. In some embodiments, the present invention provides for the use of the articles described above to enhance healing of a wound or modulate one or more properties of cells in the wound environment or in the immediate vicinity of the wound.

DESCRIPTION OF THE FIGURES

FIG. 7 provides a list of antimicrobial polypeptides, identified by name and AMSDb database ID number.

DEFINITIONS

Figure 1:
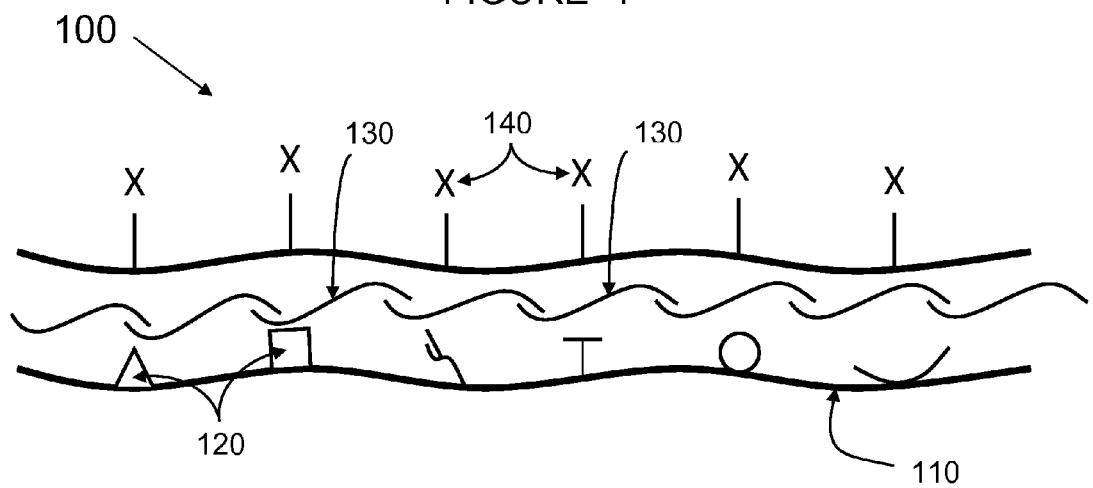
FIG. 1 provides a schematic of a wound bed modified with a polyelectrolyte multilayer.

To facilitate an understanding of the invention set forth in the disclosure that follows, a number of terms are defined below.

The term "wound" refers broadly to injuries to the skin and subcutaneous tissue initiated in different ways (e.g., pressure sores from extended bed rest and wounds induced by trauma) and with varying characteristics. The methods and compositions described herein are useful for treatment of all types of wounds, including wounds to internal and external tissues. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum).

The term "partial thickness wound" refers to wounds that encompass Grades I-III; examples of partial thickness wounds include burn wounds, pressure sores, venous stasis ulcers, and diabetic ulcers. The term "deep wound" is meant to include both Grade III and Grade IV wounds. The present invention contemplates treating all wound types, including deep wounds and chronic wounds.

The term "chronic wound" refers to a wound that has not healed within 30 days.

The phrases "promote wound healing," "enhance wound healing," and the like refer to either the induction of the formation of granulation tissue of wound contraction and/or the induction of epithelialization (i.e., the generation of new cells in the epithelium). Wound healing is conveniently measured by decreasing wound area.

The term "wound active agent" refers to compounds that induce a desired pharmacological, physiological effect useful in the treatment and healing of a wound, wherein the effect may be prophylactic or therapeutic. The terms also encompass pharmaceutically acceptable, pharmacologically active derivatives of those active agents specifically mentioned herein, including, but not limited to, trophic factors, extracellular matrices, enzymes, enzyme inhibitors, defensins, polypeptides, anti-infective agents, buffering agents, vitamins and minerals, analgesics, anticoagulants, coagulation factors, anti-inflammatory agents, vasoconstrictors, vasodilators, diuretics, and anti-cancer agents.

The term "polyelectrolyte multilayer" refers to the composition formed by sequential and repeated application of anionic and cationic polyelectrolytes to form a multilayered structure. For examples, these layers are formed by the alternating addition of anionic and cationic polyelectrolytes to a wound or to a solid support. The term "polyelectrolyte layer" also refers to the composition formed by sequential and repeated application of anionic and cationic polyelectrolytes to a wound or support. In addition, the term "polyelectrolyte layer" can refer to a single layer composed of anionic or cationic polyelectrolyte molecules, existing either as one layer within multiple layers, or as a single layer of only one type of polyelectrolyte molecules on a wound or support. While the delivery of the polyelectrolytes to the wound bed is sequential in preferred embodiments, the use of the term "polyelectrolyte multilayer" is not limiting in terms of the resulting structure of the coating. It is well understood by those skilled in the art that inter-diffusion of polyelectrolytes can take place leading to structures that may be well-mixed in terms of the distribution of anionic and cationic polyelectrolytes. It is also understood that the term polyelectrolyte includes polymer species as well as nanoparticulate species, and that it is not limiting in scope other than to indicate that the species possesses multiple charged or partially charged groups. It is also well understood by those skilled in the art that multilayer structures can be formed through a variety of interactions, including electrostatic interactions and others such as hydrogen bonding. Thus, the use of the term "polyelectrolyte" is not limiting in terms of the interactions leading to the formation of the wound bed constructs.

The term "crosslinked" herein refers to a composition containing intermolecular crosslinks and optionally intramolecular crosslinks as well, arising from the formation of covalent bonds. Covalent bonding between two crosslinkable components may be direct, in which case an atom in one component is directly bound to an atom in the other component, or it may be indirect, through a linking group. A crosslinked structure may, in addition to covalent bonds, also include intermolecular and/or intramolecular noncovalent bonds such as hydrogen bonds and electrostatic (ionic) bonds.

The term "covalent modification agent" refers to any molecule that covalently links molecules to each other. Covalent modification agents include homobifunctional and heterobifunctional cross-linkers as well as photoactivatable cross linkers.

The term "homobifunctional cross-linker" refers to a molecule used to covalently link identical or similar molecules to each other. Homobifunctional cross-linkers have two identical reactive groups; thus, a homobifunctional cross-linker can only link molecules of the same type to each other. Conversely, a "heterobifunctional cross-linker" refers to a molecule used to covalently link dissimilar molecules to each other, because it has two or more different reactive groups that can interact with various molecules of different types. Hetero- and homo-multifunctional crosslinkers refers to multivalent crosslinkers with both hetero- and homo-crosslinking functionalities. Activated dendrimers are an example of multifunctional crosslinkers.

The term "subject" refers to any animal (e.g., a mammal), including, but not limited to, humans, non-human primates, rodents, dogs, cats, and the like, which is to be the recipient of a particular treatment. Typically, the terms "subject" and "patient" are used interchangeably herein.

The term "surfactant" refers to an amphiphilic material that modifies the surface and interface properties of liquids or solids. Surfactants can reduce the surface tension between two liquids. Detergents, wetting agents, emulsifying agents, dispersion agents, and foam inhibitors are all surfactants.

The term "block copolymer" refers to a polymer consisting of at least two monomers. In a block copolymer, adjacent blocks are constitutionally different, i.e. adjacent blocks comprise constitutional units derived from different species of monomer or from the same species of monomer but with a different composition or sequence distribution of constitutional units. A block copolymer can be thought of as two homopolymers joined together at the ends.

The term "solvent" refers to a liquid that can dissolve a substance. The term "organic solvent" refers to a solvent derived from a petroleum-based product.

The term "polyelectrolyte" refers to a water-soluble macromolecular polymer substance containing many repeating ionic constituent units, including cations and anions.

The term "primary amine" refers to a derivative of ammonia in which a hydrogen has been replaced by a hydrocarbon unit. Primary amines have the general formula $RNH_2$ and examples include, but are not limited to, aniline, methylamine, and 1-propylamine.

The term "DNA delivery agent" refers to any molecule that can bring DNA into contact with an identified target. In some instances, a DNA delivery agent causes uptake of DNA into a cell or cells, in vitro or in vivo. DNA delivery agents can be viruses including, but not limited to, adenoviruses and retroviruses. DNA delivery agents can also be non-viral agents including, but not limited to, plasmids, lipids, liposomes, polymers and peptides.

The term "exposable" refers to anything that is capable of being exposed. An exposable surface or molecule is one that is made available to interaction with other surfaces or molecules. For example, in the context of the present invention, a covalent modification agent is exposable to a wound active agent; thus, the two agents can interact with each other and form covalent bonds.

The term "functionalized" refers to a modification of an existing molecular segment to generate or introduce a new reactive functional group (e.g., a maleimido or succinimidyl group) that is capable of undergoing reaction with another functional group (e.g., a sulfhydryl group) to form a covalent bond. For example, a component containing carboxylic acid (—COOH) groups can be functionalized by reaction with N-hydroxy-succinimide or N-hydroxysulfosuccinimide using known procedures, to form a new reactive functional group in the form of an activated carboxylate (which is a reactive electrophilic group), i.e., an N-hydroxysuccinimide ester or an N-hydroxysulfosuccinimide ester, respectively. In another example, carboxylic acid groups can be functionalized by reaction with an acyl halide, e.g., an acyl chloride, again using known procedures, to provide a new reactive functional group in the form of an anhydride.

As used herein, the term "aqueous solution" includes solutions, suspensions, dispersions, colloids, and the like containing water.

As used herein, the term "click chemistry" refers to the use of chemical building blocks with built-in high-energy content to drive a spontaneous and irreversible linkage reaction with appropriate complementary sites in other blocks. These chemical reactions (e.g., including, but not limited to, those between azide and acetylene groups that combine readily with each other) are specific and result in covalent linkage between the two molecules.

The term "native chemical ligation" refers to a chemoselective reaction of two unprotected peptide segments. The reaction results in an initial thioester-linked species, then spontaneous rearrangement of this transient intermediate occurs, yielding a full-length product with a native peptide bond at the ligation site.

The term "specific protein binding" refers to an interaction between two or more proteins that have high affinity and specificity for each other. Proteins must bind to specific other proteins in vivo in order to function. The proteins are required to bind to only one or a few other proteins of the few thousand proteins typically present in vivo; these interactions are employed in vitro in the present invention to attach wound active agents to the wound. In the context of the present invention, specific protein binding interactions include, but are not limited to, those between biotin and avidin, neutravidin, or streptavidin; glutathione-S-transferase and glutathione; and nickel-nitrilotriacetic acid and polyhistidine.

DETAILED DESCRIPTION OF THE INVENTION

The complex nature of wounds, and the lack of significant clinical progress based on current therapies, indicates the urgent need for new and unconventional approaches. The microenvironment of the pathologic/chronic wound bed is dysregulated with alterations in extracellular matrix constituents, degradative enzymes, growth factor and other cytoactive factor activity. The present invention provides compositions and methods for engineering of the wound bed itself by, for example, altering the surface chemistry/structure of the wound bed to promote favorable cell behaviors that accelerate wound healing. In some embodiments, the wound bed is first treated with a priming agent (i.e., primer) that provides a uniform, reactive bed on the wound surface. The primed wound bed is then treated with a desired agent, such a wound active agent.

In normal wound healing, the coordinated interplay between fibroblasts, vascular cells, extracellular matrix components and epithelial cells results in a seamless progression through an inflammatory reaction, wound repair, contracture and coverage by an epithelial barrier. However, in many subjects with dysregulated wound microenvironment, systemic disease or other confounding circumstances, the wound healing processes become asynchronous resulting in an indolent ulcer (Pierce, 2001, Am. J. Pathol. 159:399). In other subjects, a loss or lack of regulatory responses to appropriately modulate cellular behaviors during healing causes an exuberant proliferative response that in itself is a problem for the subject. This is particularly true for patients prone to keloid formation or in burn patients where excessive fibroblastic proliferation and collagen production result in disfiguring and disabling scar formation.

It is clear that across the spectrum of non-healing wounds that there are a variety of inciting mechanisms and wound microenvironments. These wounds exhibit pathology at many junctures in the progression to closure. Deficits in angiogenesis, fibroblastic responses and re-epithelialization all play a role in chronic wounds. Thus, a single factor treatment approach to chronic wounds is not likely to be fruitful across the disparate array of wounds presented in the clinical milieu. In such a heterogeneous environment, a more promising strategy involves the identification of compounds that are able to modulate specific aspects of the cellular response and behavior in the wound environment, providing the potential for custom crafting of a healing response tailored to the individual wound and patient.

Due to the heterogeneous spectrum of wound environments, it is contemplated that stimulating a "desirable" healing response is best achieved by a differential modulation of the cellular responses within the wound. The present invention provides for the selection of a subset of cytoactive compounds from a list of candidates for immobilization into the wound bed so as to differentially modulate the endothelial, fibroblastic and epithelial components within the healing response. As such, the present invention provides the potential to achieve high quality healing responses in a variety of clinical conditions, thereby providing a strategy for engineering the wound bed for personalized therapeutics for each unique wound healing challenge encountered by a clinician. Specific examples where differential modulation of the cellular responses within the wound would yield substantial benefit include chronic wounds in diabetics or venous stasis ulcers, where pancellular promotion of healing responses is desired but in particular a vibrant angiogenic response is needed to support all of the other aspects of wound healing. In other wounds, where the strength of the healed wound is a key concern, modulation to promote a fibroblastic response with a normal angiogenic and epithelial component is desirable.

In contrast, in some burns, such as deep second degree burns where dermal and hair shaft epithelial elements persist to replace lost tissues, a rich angiogenic and epithelial response is needed, but it is desirable to mitigate the fibroblastic reaction to reduce scar hypertrophy, contracture and disfigurement. A similar mitigation is desirable in healing subjects prone to keloid formation where the proliferative fibroblastic response in these wounds must be suppressed. It is also advantageous in wounds near joints or orifices to be able to promote rapid healing and coverage with epithelium but modulate the fibroblastic response so that improved suppleness of the tissue is retained. Modulation of the fibroblastic response in this way has the potential to provide superior clinical outcomes and reduce the need for subsequent reconstructive procedures targeted at recovery of limb or other critical bodily functions. The feasibility of such an approach has been demonstrated previously, such as in the report by Muehlberger and colleagues on the effects tretinoin on incisional wounds (Muehlberger et al., 2005, J. Am. Acad. Derm. 52:583). In that study, application of tretinoin resulted in an increased fibroblastic proliferation but the production of collagen was diminished.

The modification of surfaces has become an important challenge in the last decade for applications in implant materials, prostheses, and artificial organs, allowing broad medical applications for implant and tissue engineering (Langer and Vacanti, 1993, Science 260:920); Peppas and Langer, 1994, Science 263:1715; Angelova and Hunkeler, 1999, Trends Biotechnol. 17:409). For the improved integration efficiency of implants, several approaches, involving the alteration of physicochemical, morphological, and biochemical properties of device surfaces, have been investigated in an effort to obtain a suitable bone-implant interface. Self-assembled monolayers (SAMs) or Langmuir-Blodgett techniques have been commonly employed to produce new interfaces (Mrksich, 1997, Curr. Opin. Colloid Interface Sci. 2:83; Lösche, 1997, Curr. Opin. Solid State Mater. Sci. 2:546).

More recently, a new versatile method of self assembled architectures based on the alternate deposition of polyanions and polycations has been developed for the buildup of multilayered polyelectrolyte films (Decher, 1997, Science 277:1232). Besides varying film thickness, roughness, and porosity, it is also possible to incorporate in the film architecture functionalized macromolecules (Caruso et al., 1997, Langmuir 13:3427; Cassier et al., 1998, Supramol. Sci. 5:309). It has also been demonstrated that the layer-by-layer deposition process is not limited in applicability to polyelectrolytes, but can be applied to viruses, nanoparticles, non-ionic polymers, proteins and other forms of microscopic and nanoscopic matter. A recent review provides information on a wide range of species and interfacial structures that can be formed by the layer-by-layer deposition procedure. The scope of the invention described herein is not limited to polyelectrolytes but applies to all species that have been demonstrated to be incorporated into interfacial structures by the layer-by-layer deposition process.

The present invention provides a variety of embodiments for altering the composition of the wound bed. In some embodiments, a wound modifying agent is applied to prime the wound bed. As described in detail below, wound modifying agents are agents that applied to a wound bed and either covalently or noncovalently modify the wound bed. Examples of wound modifying agents include homobifunctional and heterobifunctional linkers, polyelectrolytes, nonionic polymers, combinations of polyelectrolytes and nonionic polymers, and nano- and micro-particles including beads and needles. In some embodiments, the wound modifying agent alters a property of the wound bed selected from the group consisting of compliance, pH, alkalinity, and oxidative or reductive strength, net charge, hydrophilicity, osmotic strength, nanoscale or submicron topographic features, electroconductivity, MMP production, phagocyticis, and transglutaminase activity. In preferred embodiments, the wound modifying agents are used to incorporate wound active agents so that the wound active agents are localized to the wound bed. The wound active agents can be covalently or noncovalently attached to the wound modifying agent. Furthermore, the wound active agents may form a gradient via the wound modifying agent. In further embodiments, the wound modifying agents alter the compliance of the wound bed. In these embodiments, the polymers or nano- or microparticles have a predetermined hardness. In further embodiments, the compliance gradients with varying levels of hardness may be formed by the polymers, nano- or microparticles.

Figure 2:
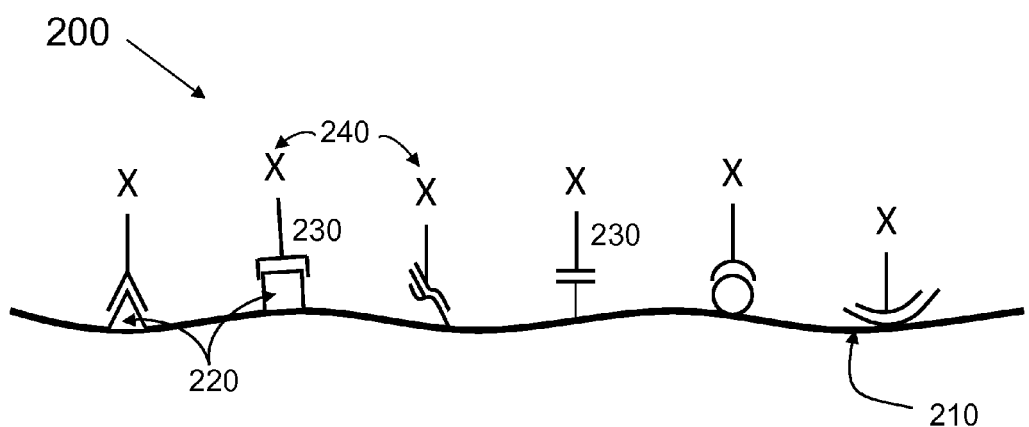
FIG. 2 provides a schematic of a wound bed modified with covalent modifying agents.

In one embodiment, the present invention provides for the deposition and immobilization of cytoactive factors and extracellular matrices (ECMs) on the wound bed by using, for example, polyelectrolyte multilayers or beads. FIG. 1 provides a schematic diagram 100 of a wound bed 110 on which a polyelectrolyte multilayer 130 has been deposited. The diagram 100 depicts that the wound bed 110 comprises a heterogeneous surface depicted by shapes 120 which represent different chemical moieties. The polyelectrolyte multilayer 130 provides a homogenous surface onto which functional groups can 140 can be attached to form a homogenous functionalized surface 150. In the embodiment depicted, the functional groups are uniform, however, in some preferred embodiments, different functional groups are utilized. A wide variety of active agents can then be attached to the surface via the functional groups 140. In other embodiments, the wound bed is covalently modified with covalent modification agents. The covalent modification agents include, but are not limited to, homobifunctional and heterobifunctional cross-linkers as well as photoactivatable cross linkers. FIG. 2 provides a schematic diagram 200 of a wound bed 210 comprising a heterogeneous surface depicted by shapes 220 which represent different chemical moieties. The wound bed is covalently modified by reacting covalent modification agents 230 with the different chemical moieties to provide a relatively homogenous functionalized surface 250. In preferred embodiments, covalent modification agents 230 present functional groups 240. In the embodiment depicted, the functional groups are uniform, however, in some preferred embodiments, different functional groups are utilized. A wide variety of active agents can then be attached to the surface via the functional groups 240. These embodiments are discussed in more detail below.

It is contemplated that the wound bed is an extremely heterogeneous environment. The compositions and methods of the present invention are designed to modify the wound bed to provide a homogenous environment that provides for uniform and predictable delivery or uniform incorporation of active agents into the wound bed. Surprisingly, it has been found that modification of wound beds in this manner greatly reduces the amount of active agent which is needed; i.e., the effective amount of active agent needed is reduced. Surface functionalization allows for precise control of the amount of active agent used or delivered and further allows for the formation of gradients of active agents on the wound bed. In some preferred embodiments, the priming agent is optimized to react with the wound bed. In some embodiments, the priming agent provides an optimized surface for enhanced or optimized delivery of an active agent. In some embodiments, a chemical parameter of the wound bed is changed. For example, the wound bed may be modified to be more or less acidic, basic, alkaline, reducing, or oxidizing or have a higher or lower ionic strength.

There is a wide array of candidate molecules for improving healing chronic wounds. For example, basement membrane constituents and growth factors promote wound healing. In some embodiments, the extracellular matrices deposited and immobilized are constituents of native basement membrane. Native ECMs comprise a mixture of glycoproteins, proteoglycans and hyaluronic acid. These glycoproteins and proteoglycans include, but are not limited to, fibrin, elastin, fibronectin, laminins, nidogens and collagens. Cytoactive factors such as growth factors are also part of ECMs. In some embodiments, extracellular matrix components, such as collagen, laminin, or hyaluronic acid are deposited and immobilized on a wound bed. In some embodiments, a synthetic matrix such as MATRIGEL™ is deposited on a wound bed. MATRIGEL™ is a commercially available basement membrane like complex that retains many characteristics of a native basement membrane, including a three-dimensional nanoscale topographic surface. The present invention is not limited to a particular mechanism. Indeed, an understanding of the mechanism is not necessary to practice the present invention. Nonetheless, it is contemplated that the nanoscale topographic features of a basement membrane modulate fundamental cell behaviors including migration, adhesion, proliferation and differentiation (Abrams et al., 2002, Biomimetic Materials and Design: Interactive Biointerfacial, Tissue Engineering, and Drug Delivery, Eds. Dillow and Lowman; Diehl et al., 2005, J. Biomed. Mater. Res. A 75:603; Foley et al., 2005, Biomaterials 26:3639; Karuri et al., 2004, J. Cell Sci. 117:3153; Liliensiek et al., 2006, J. Biomed. Mater. Res. A 79:185). In some embodiments, the present invention further provides methods, formulations, compositions and kits for altering the compliance of the wound surface. In some embodiments, the local compliance (the compliance that cells see) is altered by immobilizing a thin layer of extracellular matrix constituents such as MATRIGEL™ or an appropriate hydrogel or other synthetic matrix or by enzymatic treatment of the wound bed. In other embodiments, compliance is altered by the addition of cross-linking agents to the wound bed to cross-link components already presenting the wound bed, or components deliberately introduced into the wound bed. It has also been demonstrated by Picart and coworkers that it is possible to control the compliance of multilayer structures formed from polyelectrolytes by the addition of cross-linking agents.

In some embodiments, the cytoactive factors that are deposited and immobilized on a wound bed include, but are not limited to, those factors that are mitogenic for epithelial cells and vascular endothelial cells and other factors that are elements in wound closure. For example, in some embodiments, growth factors such as platelet derived growth factor (PDGF), and/or epidermal growth factor (EGF), known to be mitogenic for epithelial cells are deposited in a wound bed. In other embodiments, vascular endothelial growth factor (VEGF), known to be mitogenic for vascular endothelial cells, comprise the cytoactive factors immobilized on the wound bed. It is contemplated that the present invention is not limited by the ECM components or cytoactive factors immobilized on the wound bed, indeed any extracellular matrix components and/or cytoactive factor that improves wound healing is equally applicable. Additional cytoactive and wound active agents that can be incorporated are provided below.

I. Priming the Wound Bed

In some embodiments, the present invention provides compositions and methods for priming the wound bed to provide uniform reactive surface for later modification. Suitable compositions for priming a wound bed include, but are not limited to, polyelectrolytes and chemical crosslinking agents that react covalently with functional groups found in wound beds such as carboxy, thiol, amide and sugar groups.

A. Multilayer Deposition on Wound Bed

In some embodiments, the present invention provides compositions, formulations, methods and kits for depositing a multilayer structure on a wound bed. In some embodiments, the multilayer structures comprise layers of polymers that form polyelectrolytes, while in other embodiments, the multilayers comprise polymers that do not have a charge (i.e., non-ionic polymers) or a combination of charged and uncharged polymer layers. In some embodiments, it is contemplated that polyelectrolyte films built-up by the alternated adsorption of cationic and anionic polyelectrolyte layers constitute a novel and promising technique to modify wound surfaces in a controlled way [(Decher et al., 1992, Thin Solid Films 210/211:831; Decher, 1997, Science 277:1232). One of the most important properties of such multilayers is that they exhibit an excess of alternatively positive and negative charges (Caruso et al., 1999, J Am Chem Soc 121:6039; Ladam et al., 2000, Langmuir 16:1249). Not only can this constitute the motor of their buildup (Joanny, 1999, Eur. Phys. J. Biol. 9:117), but it allows, by simple contact, to adsorb a great variety of compounds such as dyes, particles (Cassagneau et al., 1998, J. Am. Chem. Soc. 120:7848; Caruso et al., 1999, Langmuir 15:8276; Lvov et al., 1997, Langmuir 13:6195), clay microplates (Ariga et al., 1999, Appl. Clay Sci. 15:137) and proteins (Keller et al., 1994, J. Am. Chem. Soc. 116:8817; Lvov et al., 1995, J. Am. Chem. Soc. 117:6117; Caruso et al., 1997, Langmuir 13:3427).

In some embodiments, the polymer multilayers, such as polyelectrolyte multilayers, are nanoscale in dimension. Accordingly, in some embodiments, the polymer multilayers are from about 1 nm to 1000 nm thick, from about 1 nm to 500 nm thick, from about 1 nm to 100 nm thick, from about 1 nm to about 25 nm thick, from about 1 nm to about 10 nm thick, or less than about 500 nm, 100 nm, 25 nm or 10 nm thick. It is contemplated that the nanoscale dimension of the polymer multilayers (i.e., the nanoscale thickness) allows for the loading of a lower total amount of an active agent while still allowing delivery of an effective amount (i.e., an amount of active agent that accelerates wound healing as compared to controls) of the active agent as compared to matrix structures with greater thickness. It is contemplated that the lower total loading levels result in reduced toxicity in the wound environment, especially when antimicrobial compounds are incorporated into the polymer multilayer.

In some embodiments, the compliance of the polymer multilayers is adjusted to facilitate cell migration in the wound. In some embodiments, the polymer multilayers exhibit a compliance, measured in kilopascals (kPa) of from about 3 to about 500 kPa, about 7 to about 250 kPa, about 10 to about 250 kPA or from about 10 to about 200 kPa.

1. Formation of Polyelectrolyte Layers

The cationic polyelectrolyte poly(L-lysine) (PLL) interacts with anionic sites on cell surfaces and in the extracellular matrix (Elbert and Hubbell, 1998, J. Biomed. Mater. Res. 42:55). In some embodiments, the present invention provides a method of treating a wound with the sequential application of a cationic polyelectrolyte, an anionic polyelectrolyte, and a wound active agent to the wound. In other embodiments, the treatment includes the sequential and repeated application of a cationic polyelectrolyte, an anionic polyelectrolyte, and a wound active agent to the wound.

Polyelectrolyte layers are formed by alternating applications of anionic polyelectrolytes and cationic polyelectrolytes to surfaces to form a polyelectrolyte layer. The layers can be used to deliver a wound active agent to a wound. Preferably, at least four layers, and, more preferably, at least six layers are used to form the polyelectrolyte multilayer.

The method of treatment of the present invention is not limited to use on a wound surface. The formation of a polyelectrolyte layer that includes a wound active agent may be formed on any surface to which delivery of a wound active agent is desirable.

In some embodiments, the cationic polyelectrolyte used is PLL and the anionic polyelectrolyte used is poly(L-glutamic acid) (PGA). Indeed, the use of a variety of polyelectrolytes is contemplated, including, but not limited to, poly(ethylene imine) (PEI), poly(allylamine hydrochloride) (PAH), poly(sodium 4-styrenesulfonate) (PSS), poly(acrylic acid) (PAC), poly(maleic acid-co-propylene) (PMA-P), and poly(vinyl sulfate) (PVS). It is also possible to use naturally occurring polyelectrolytes, including hyaluronic acid and chondroitin sulfate.

In still further embodiments, the polymer is a dendrimer, grafted polymer, or star architecture polymer. In other embodiments, the multilayer responds to or is organized in the presence of an electric field, for example an electric field formed by placing electrodes on either side of a wound.

Referring to FIG. 1, in some embodiments, the polymer multilayer 130 can be comprised of polystyrene sulfonate, an amphiphilic polyelectrolyte with an affinity for hydrophobic regions of the wound bed, and an amphoteric polymer. The polymer multilayer is preferably functionalized with one or more crosslinking agents presenting an alkyne so that a uniform surface is presented (e.g., 140 in FIG. 1 where x represents an alkyne group). From this point, widely available click chemistries can be used to add desired wound active agents to the modified surface of the wound. In some embodiments, the wound modifying agent is an azide conjugate or otherwise comprises an azide group and is reacted with the alkyne groups displayed on the wound bed in a Huisgen Cycloaddition.

2. Cationic Polymers

Cationic polymers useful in the present invention can be any biocompatible water-soluble polycationic polymer, for example, any polymer having protonated heterocycles attached as pendant groups. As used herein, "water soluble" means that the entire polymer must be soluble in aqueous solutions, such as buffered saline or buffered saline with small amounts of added organic solvents as co-solvents, at a temperature between 20 and 37° Centigrade. In some embodiments, the material will not be sufficiently soluble (defined herein as soluble to the extent of at least one gram per liter) in aqueous solutions per se but can be brought into solution by grafting the polycationic polymer with water-soluble polynonionic materials such as polyethylene glycol.

Representative cationic polymers include natural and unnatural polyamino acids having net positive charge at neutral pH, positively charged polysaccharides, and positively charged synthetic polymers. Examples of suitable polycationic materials include polyamines having amine groups on either the polymer backbone or the polymer side chains, such as poly-L-lysine (PLL) and other positively charged polyamino acids of natural or synthetic amino acids or mixtures of amino acids, including, but not limited to, poly(D-lysine), poly(ornithine), poly(arginine), and poly(histidine), and nonpeptide polyamines such as poly(aminostyrene), poly (aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyl-trimethyl ammonium chloride), and natural or synthetic polysaccharides such as chitosan. In some embodiments, PLL is a preferred material.

In general, the polymers must include at least five charges, and the molecular weight of the polycationic material must be sufficient to yield the desired degree of binding to a tissue or other surface, having a molecular weight of at least 1000 g/mole.

3. Anionic Polymers

Polyanionic materials useful in the present invention can be any biocompatible water-soluble polyanionic polymer, for example, any polymer having carboxylic acid groups attached as pendant groups. Suitable materials include alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose and crosmarmelose, synthetic polymers and copolymers containing pendant carboxyl groups, such as those containing maleic acid or fumaric acid in the backbone. Polyaminoacids of predominantly negative charge are also suitable. Examples of these materials include polyaspartic acid, polyglutamic acid, and copolymers thereof with other natural and unnatural amino acids. Polyphenolic materials such as tannins and lignins can be used if they are sufficiently biocompatible. Preferred materials include alginate, pectin, carboxymethyl cellulose, heparin and hyaluronic acid.

4. Nonionic Polymers

In some embodiments, the multilayer structures are formed from uncharged polymers or from a combination of charged and uncharged polymers. Examples of uncharged polymers include, but are not limited to, dextran, dextran sulfate, diethylaminoethyl (DEAE)-dextran, hydroxyethyl cellulose, ethyl(hydroxyethyl) cellulose, acrylamide, polyethylene oxide, polypropylene oxide, polyethylene oxide-polypropylene oxide copolymers, $PAAN_a$, Ficoll, polyvinylpyrrolidine, and polyacrylic acid.

5. Amphoteric Polymers

In some embodiments, the multilayer structures are formed from one or more amphoteric polymers, alone in combination with the other polymers described herein. In some embodiments, the amphoteric polymers comprise one or more of acrylic acid (AA), DMAEMA (dimethylaminoethyl methacrylate), APA (2-aminopropyl acrylate), MorphEMA (morpholinoethyl methacrylate), DEAEMA (diethylaminoethyl methacrylate), t-ButylAEMA (t-butylaminoethyl methacrylate), PipEMA (piperidinoethyl methacrylate), AEMA (aminoethyl methacrylate), HEMA (2-hydroxyethyl methacrylate), MA (methyl acrylate), MAA (methacrylic acid) APMA (2-aminopropyl methacrylate), AEA (aminoethyl acrylate). In some embodiments, the amphoteric polymer comprises (a) carboxylic acid, (b) primary amine, and (c) secondary and/or tertiary amine. The amphoteric polymers have an isoelectric point of 4 to 8, preferably 5 to 7 and have a number average molecular weight in the range of 10,000 to 150,000.

6. Application of Multilayers

The wound modifying agent, such as a polymer multilayer, can be applied to the wound by a variety of methods. In some embodiments, it is contemplated that the polymer or polymer multilayers is applied, preferably sequentially, to the wound using either a pump (including syringes, ink jet printers, and electrojets) or aerosol spray. In other embodiments, particle bombardment is utilized. In other embodiments, the use of a brush including an air brush is contemplated. In other embodiments, a sponge is utilized. In other embodiments a solid support or stamp such as an elastomeric material, for example, PDMS (polydimethylsiloxane), silicone, hydrogel or latex, is used to support the wound modifying agents and mechanically transfer the agent into the wound bed. In these embodiments, the polymer multilayers are pre-formed on the stamp. In further embodiments, nano- or micro-particles are arranged on the stamp for delivery to the wound. In other approaches, electric fields or magnetic fields are used to facilitate transfer of the wound modifying agents into the wound bed.

In some embodiments, the polymers are applied to a wound by a spray, such as via a pump or aerosol device. In some embodiments, the polymer layers are applied sequentially. In one embodiment, a solution, dispersion, or suspension of the wound modifying agent and wound active agent is sprayed onto the wound to form the polyelectrolyte layer. In embodiments where the wound modifying agent and wound active agent are supplied as aerosols, a propellant is used to provide the force for expulsion from the container. In some embodiments, the wound modifying agent or the wound active agent and the propellant form a single liquid phase so that the composition is delivered consistently.

In general, for aerosol delivery, the ingredients of the composition are mixed to form a substantially homogenous solution, slurry, dispersion, or the like. For two-part systems, each part is mixed. The compositions are placed in an appropriate container and the propellant is added using conventional techniques, such as cold filling or pressure filling techniques. The composition can be delivered using a commercially available aerosol sprayer such as, for example, the Preval™ aerosol spray unit available from Precision Valve Corporation, NY, USA, which has a modular power unit and refillable container jar. The propellant is a mixture of propane, isobutane, and dimethyl ether.

The composition can also be delivered using a syringe outfitted with a spray head, or a dual spray device outfitted with a spray head and, optionally, a mixing chamber. The device may include a meter so that the quantity of applied composition can be controlled.

Any of a number of propellants known to those skilled in the art can be used, provided that it is chemically inert to the other ingredients of the composition. Suitable propellants include vinyl chloride and mixtures of vinyl chloride and dichlorodifluoromethane, other fluorochlorohydrocarbons known as the Freons and the Genetrons, and blends of fluorochlorohydrocarbons, chlorinated hydrocarbons, and hydrocarbons. Examples of fluorochlorohydrocarbons include trichloromonofluoromethane, dichlorodifluoromethane, dichloromonofluoromethane, 2-tetrafluoroethane, 1,1-dichloro-1,2,2-tetrafluoroethane, 1-chloro-1,1-difluoroethane, 1,1-difluoroethane, and octofluorocyclobutane, and mixtures thereof. Examples of hydrocarbons include liquefied petroleum gases like propane, isobutane, and N-butane and mixtures thereof. Dimethyl ether is another propellant. Compressed gas propellants that are preferably non-toxic, non-flammable, and inert can be used. Examples include carbon dioxide, nitrous oxide and $N_2$ and the like. Mixtures of the above are often used.

The quantity of propellant used is critical only in that if an insufficient amount is used, the driving force to expel the entire composition from the container will be lacking. Generally, the composition will comprise from 75% to 95% by weight propellant.

In some embodiments, the invention contemplates a kit comprising a container with a cationic polyelectrolyte, a second container containing an anionic polyelectrolyte, and a third container containing at least one wound active agent. In still other embodiments, in addition to a container with a cationic polyelectrolyte, a second container containing an anionic polyelectrolyte, and a third container containing at least one wound active agent, the kit provides an application device for administering the polyelectrolytes and at least one wound active agent to the wound. In some preferred embodiments, the containers comprise a propellant. In other embodiments, the containers comprise a pump.

In some embodiments, contacting comprises delivery of the polymer and the at least one wound active agent to the wound using a reaction chamber dressing (RCD). In some embodiments, it is contemplated that the RCD will comprise a solid barrier adhered to an area completely surrounding the wound. Within the solid barrier reside inflow and outflow orifices to which tubes from solution reservoirs can be connected. The use of a variety of solid barriers is contemplated, including, but not limited to, Gortex, latex, Teflon, PVDF, plastic and rubber.

In some embodiments, the wound modification agents are applied to the wound by microfluidics printing, microstamping (U.S. Pat. Nos. 5,512,131 and 5,731,152, both of which are incorporated by reference herein in their entirety), or microcontact printing (PCT Publication WO 96/29629, incorporated by reference herein in its entirety). In other embodiments, the wound modifying agents are applied to the wound via a pulse het such as an inkjet printer. Examples of suitable inkjet printers for application of biological fluids include those described in U.S. Pat. No. 7,128,398, WO 95/25116 and WO 98/41531, each of which is incorporated by reference in its entirety. In other embodiments, the wound modifying agents are applied by a drop dispensers such as the tip of a pin or in an open capillary and, touch the pin or capillary to the surface of the substrate. Such a procedure is described in U.S. Pat. No. 5,807,522. When the fluid touches the surface, some of the fluid is transferred. In other embodiments, the wound modifying agents are applied be pipetting, micro-pipetting or positive displacement pumps such as the Biodot equipment (available from Bio-Dot Inc., Irvine Calif., USA).

One or more wound active agents are preferably applied to the wound along with the wound modification agent. In some embodiments, the wound active agent is covalently attached to the wound modification agent. In other embodiments, the wound active agent is incorporated into the wound modifying agent, for example, by application during sequential application of polymer layers in a polymer multilayer. In other embodiments, the wound active agents are delivered by a microarrayer, pipette, positive displacement pump, inkjet printer, microneedle array, elastomeric stamp, gene gun, electrojet, or air brush as described above in relation to the wound modifying agents.

B. Modification of Wound Beds with Biocompatible Particles

In some embodiments, the wound modifying agent is a nano- or micro-particle. In some embodiments, nanometer to submicrometer sized biocompatible particles, such as spherical (e.g., beads) and/or non-spherical (e.g., oblongs, needles, cubes, tetrahedral, mushroom-like structures, haybale-like structures) particles or electrospun polymers, are applied (e.g., either directly or indirectly) to the wound bed, thereby creating a three-dimensional topographic wound bed. For example, application of biocompatible particles to a wound bed results in the creation of knobs, ridges, spikes, undulations, and the like in the wound bed. Microbeads have a size generally ranging from about 1 to about 500 micrometers, while nanobeads have a size generally ranging from about 1 to about 1000 nanometers. Microbeads may further comprise micro- (i.e., from 1 to 100 micrometers) or nano-scale (0.1 to 1000 nanometer) features on the surface of the bead. Nanobeads may further comprise nanoscale features (i.e., 0.1 to 500 nanometer features) on the surface of the bead.

In some embodiments, the biocompatible particles are biodegradable. In some embodiments, the biocompatible particles are not biodegradable. The biocompatible particles, for example, are modified with surface chemistry cross-linkers that allow attachment and immobilization of wound active agents, extracellular matrix compounds, polyelectrolytes, etc. as described further herein. It is contemplated that the incorporation of modified biocompatible particles, for example, facilitates the presentation of ECM constituents that support epithelial coverage of the wound, provides cytoactive factors for wound healing, and introduces topographic features that support cellular behaviors for promoting wound healing. In some embodiments, the biocompatible particles are functionalized with mesoscopic cross-linkers to, for example, broadly enable covalent chemistry in the wound bed. In some embodiments, cross-linkers are attached to negatively charged biocompatible particles. In some embodiments, the biocompatible particles comprise layers of multiple different constituents for wound healing, or a single constituent for wound healing. For example, spherical particles such as beads placed in a wound bed comprise, or upon which are layered, one or more intermixed species of polyelectrolytes, ECM agents, proteins with hydrolysable bonds, proteins with enzymatically cleavable bonds, and the like for wound healing as previously described. In some embodiments, antimicrobials, either alone or in combination with other wound healing compositions, are also applied to the biocompatible particles. Antimicrobials include, but are not limited to, antibiotics, metal based antimicrobial compositions comprising silver, copper, selenium, triclosan-based antimicrobials, thiabendazole-based antimicrobials, isothiazolinone-based antimicrobials, zinc-pyrithione-based antimicrobials, and/or 10'-oxybisphenoxarsine-based antimicrobials (OBPA). The present invention is not limited by the type of antimicrobial used.

In some embodiments, the size of the biocompatible particles, such as beads, are at least 1 nm, at least 5 nm, at least 10 nm, at least 20 nm, at least 50 nm, at least 100 nm, at least 200 nm, at least 300 nm, at least 500 nm, or at least 800 nm in diameter. In some embodiments, beads and other spherical and non-spherical particles contain their own surface topography. For example, the bead surface may comprise undulations, indentations, tunnels, holes, knobs, ridges, etc. Spherical particles, such as beads, may or may not be inert and may, for example, be magnetic. Magnetic beads comprise, for example, a magnetic core or magnetic particles. Examples of different bead compositions are found at, for example, U.S. Pat. Nos. 5,268,178, 6,458,858, 6,869,858, and 5,834,121, each of which is incorporated herein by reference in its entirety.

In some embodiments, biocompatible particles of the present invention used for wound healing are coated with layers of polyelectrolytes, ECM components, antimicrobials, proteins with hydrolysable bonds, proteins with enzymatically cleavable bonds, etc. and other wound healing compositions wherein the surface compliance of the beads is maintained for optimal wound healing. For example, the compliance of the layers for wound healing as deposited on the biocompatible particles are contemplated to be of optimal stiffness (e.g., not too soft, not too hard) such that cells within the wound bed are capable of optimal anchorage and spreading. Engler et al. (2004, Biophys. J. 86:617-628) discusses substrate compliance for cell anchorage and spreading. In some embodiments, the biocompatible particles are layered with polyelectrolytes, ECM components, antimicrobials, etc. wherein substrate stiffness of at least 1 kPa, at least 5 kPa, at least 8 kPa, at least 10 kPa, at least 20 kPa, at least 40 kPa, at least 60 kPa, at least 80 kPa is realized as measured using the methods of Engler et al. (2004). In preferred embodiments, substrate compliance of the wound healing compositions as applied to biocompatible particles is at least 8 kPa to about 80 kPa or 100 kPa. It will be recognized that hardness within these limit are contemplated without specifically listing all such hardnesses, for example, 10, 20, 30, 40, 50, 60, or 70 kPa limits as upper or lower ranges are all contemplated by the present invention. In some embodiments, the ECM composition preferentially used in conjunction with polyelectrolytes, antimicrobials, and other wound healing compositions is collagen.

In some embodiments, the layers as applied to a wound bed or to a biocompatible particle comprise gradients of wound healing compositions, for example, wound active agents. For example, the concentrations of the compositions are layered in a wound bed or on a biocompatible particle in a gradient such that higher concentrations of a particular composition is greater proximal to the wound bed than distal to the wound bed in a vertical fashion. The converse, where concentrations of compositions is greater distal to the wound bed than proximal, is also contemplated. Concentration of compositions in a wound bed or on a biocompatible particle wherein a horizontal gradient is deposited is also contemplated. Topographical gradients are also contemplated, wherein compositions are deposited such that the concentrations of compositions in a wound bed or on a biocompatible particle follow the topography of the substrate, for example, a higher concentration of compositions is deposited in the valleys of undulations of an exemplary substrate compared to the peaks of the undulations. Likewise, the present invention contemplates that compliance gradients can be formed in the wound bed by controlled application of micro- or nano-beads of varying hardness. For example, beads having one, two, three, four or more different hardnesses are applied to form a vertical gradient (i.e., a depth gradient) on the wound or a horizontal gradient (i.e., a gradient along the length or width of the wound), or a combination of vertical and horizontal gradients. Horizontal and vertical gradients can also be formed with beads functionalized with 1, 2, 3, 4 or more different wound active agents. See Ichinose et al., Biomaterials. Volume 27, Issue 18, June 2006, Pages 3343-3350; Stefonek et al., Immobilized gradients of epidermal growth factor promote accelerated and directed keratinocyte migration. Wound Repair and Regeneration (OnlineEarly Articles). doi:10.1111/j.1524-475X.2007.00288.x; Kapur et al., Immobilized concentration gradients of nerve growth factor guide neurite outgrowth. Journal of Biomedical Materials Research Part A. Volume 68A, Issue 2, Pages 235-243; DeLong et al., Covalently immobilized gradients of bFGF on hydrogel scaffolds for directed cell migration. Biomaterials 26 (2005) 3227-3234; Liu, et al., 2007 Sep. 25; 17892312 Endothelial Cell Migration on Surface-Density Gradients of Fibronectin, VEGF, or Both Proteins.

In some embodiments, wound healing compositions applied to the wound bed or biocompatible particles (e.g., beads, needles, etc.) are time released, such that wound healing compositions that are applied to the wound bed or biocompatible particles are released over a period of time, for example 3 hours, 5 hours, 10 hours, 1 day, several days, one week, several weeks, etc. thereby providing short and/or long term treatment for the wound bed.

In some embodiments, biocompatible particles used in wound bed healing applications of the present invention are not, for example, spherical as previously described, but take on shapes such as oblongs, needles, mushroom-like structures, haybale-like structures, etc. In some embodiments, the biocompatible particle shape is preferably needles. The manufacture of needles useful in embodiments of the present invention can be accomplished through microfabrication techniques, such as those found in, for example, McAllister et al., 2003, Proc. Natl. Acad. Sci. 100:13755-13760. In some embodiments, biocompatible particles are coated and/or layered with wound healing compositions, anti-microbials, proteins that are hydrolyzably cleavable, proteins that are enzymatically cleavable, antimicrobials, etc. as described herein. In some embodiments, the coated and/or layered biocompatible particles are applied to a wound bed by stamping, spraying, or other methods as described herein.

In some embodiments, the layers of wound healing compositions as described herein are deposited on a wound bed or on biocompatible particles by electrostatic bonding. In other compositions, non-electrostatic interactions are utilized, such as van der Waals interactions, metal ion-ligand coordination or hydrogen bonding. In some embodiments, the layers of wound healing compositions as described herein are deposited by piezoelectric application, using methods and systems as described in, for example, U.S. Pat. No. 6,368,079 and Sumerel et al., 2006, Biotechnol. J. 1:976-987. In other embodiments, the wound healing compositions are directly or indirectly deposited into the wound bed by using electrojetting technologies, including electroextrusion, and electrospraying and electrospinning. In some embodiments, the layers deposited comprise one or more wound healing compositions. In some embodiments, the layers are biocompatible particles (e.g. spherical beads, needles, and the like) intermixed with wound healing compositions. In other embodiments, layered deposition is sequential. For example, sequential deposition of wound healing compositions alone, or sequential deposition of wound healing compositions followed by biocompatible particles, followed by wound healing compositions, etc. The present invention is not limited by the constituents that make up a layer of deposition on a biocompatible particle, and many permutations of wound healing compositions and biocompatible particle layering would be apparent to a skilled artisan.

In some embodiments, the deposition of layers in the wound bed or on a biocompatible particle or other substrate to be added to a wound bed is accomplished by "stamping", also referred to as "contact printing". A stamp substrate is any substrate that can be used to transfer one or more than one entity or composition (e.g., polyelectrolytes, ECM components, proteins with hydrolysable or enzymatically cleavable bonds, etc.) that is (are) covalently or non-covalently bound to the surface of the stamp substrate to another surface. Examples of suitable stamp substrates include, but are not limited to, polydimethylsiloxane (PDMS) and other elastomeric (e.g. pliable) materials. In some embodiments, different concentrations of the same wound healing composition are arrayed in different areas of the stamp substrate. In other embodiments, a variety of different compositions are arrayed on the stamp substrate surface. In some embodiments, multiple wound healing compositions in multiple concentrations are arrayed on the stamp substrate surface. The wound healing compositions are then introduced to the stamp substrate surface, which are in turn stamped into the wound bed or onto another substrate for introduction into the wound bed (e.g., biocompatible particles).

In other embodiments, the biocompatible particles, for example needles, are coated and/or layered with wound healing compositions, antimicrobials, proteins that are hydrolyzably cleavable, proteins that are enzymatically cleavable, etc., and applied to a pad which is subsequently applied to a wound. Pads include, but are not limited to, band-aids, gauze, surgical packings, and the like. In some embodiments, the pad is impregnated with wound healing compositions, anti-microbials, proteins that are hydrolyzably cleavable, proteins that are enzymatically cleavable, etc. In some embodiments, the biocompatible particles (e.g., covered and/or layered with wound healing compositions, anti-microbials, proteins that are hydrolyzably cleavable, proteins that are enzymatically cleavable, etc.) are affixed in a detachable or non-detachable manner to the pad prior to applying the pad to a wound. In some embodiments, when the pad is removed from the wound the biocompatible particles are retained (e.g., not detached) on the pad, whereas in other embodiments when the pad is removed from the wound the nanostructures are retained (e.g., detached) in the wound bed. For example, a pad is impregnated with compositions as described and further affixed with biocompatible particles that are themselves coated and/or layered with compositions as described for wound healing. The pad with biocompatible particles is applied to the wound and while the pad is superficial to the wound bed, the biocompatible particles thereon reach down in proximity with the wound bed as compared to the location of the pad. The pad releases (e.g., either over a short period of time or in a time-release manner) the impregnated wound healing compositions on or near the surface of the wound whereas the affixed biocompatible particles release the coated and/or layered wound healing compositions (e.g., either over a short period of time or in a time-release manner) more proximal to the wound bed. Alternatively, a pad with affixed biocompatible particles (both pad and nanostructures comprising wound healing compositions as previously described) is first applied to a wound bed. The pad is subsequently removed; however the detachable biocompatible particles remain in the wound bed. The pad serves not only to deliver wound healing compositions to a wound bed, but further serves a purpose of delivering biocompatible particles, such as needles, into a wound bed. The biocompatible particles left in the wound bed, for example, continue releasing wound healing compositions to the wound bed for further healing. In some embodiments, a new (e.g., second, third, fourth, etc.) pad comprising impregnated wound healing compositions as previously described is re-applied to the wound wherein resides the biocompatible particles retained by the original application of the first pad/nanostructure. The application of the new pad, for example, serves not only to impart fresh wound healing compositions to a wound but also serves to recoat the biocompatible particles with fresh would healing compositions that are released (e.g., either over a short period of time or in a time-release manner) proximal to the wound bed.

Figure 6:
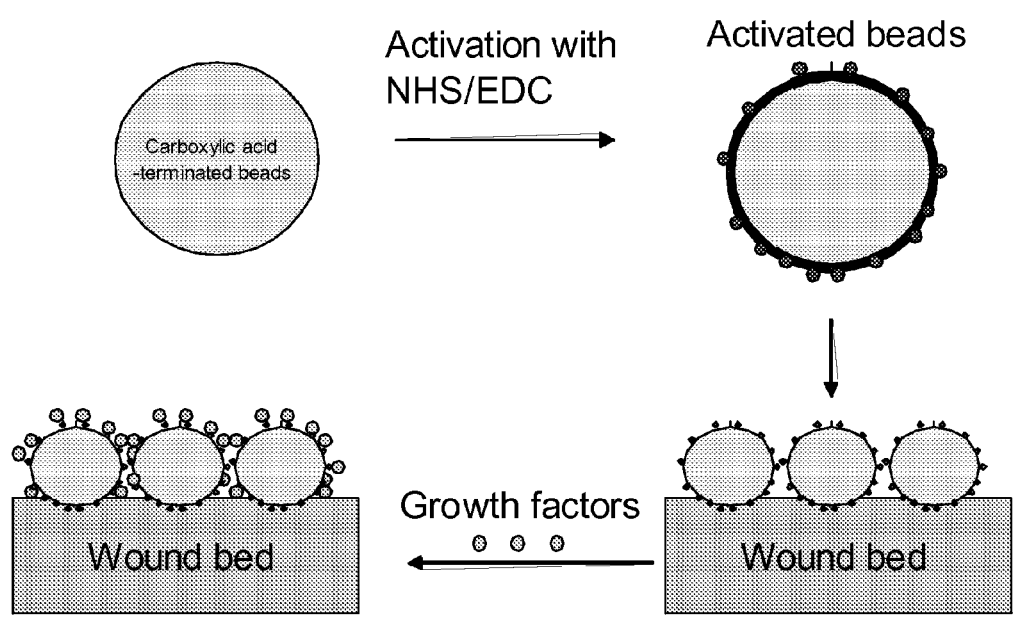
FIG. 6 is exemplary of the use of beads for healing a wound bed. In this example, carboxylic acid-terminated beads are activated outside the wound bed by using NHS and EDC. The activated beads are introduced into the wound bed and are immobilized in the wound bed via reaction of the activated surfaces of the beads with amine groups present in the wound bed. Growth factors are introduced into the wound bed and immobilized via reaction with the exposed surfaces of the activated beads.

The present invention is not limited to a particular mechanism. Indeed, an understanding of the mechanism is not necessary to practice the present invention. Nonetheless, it is contemplated that the negatively charged macromolecular species and beads do not readily pass across cell membranes, and therefore serve as a non-toxic means of wound bed healing. As well, the size of the beads used determines the nanostructure of the wound bed, thereby allowing for personalized wound bed healing therapies. FIG. 6 provides an exemplary embodiment of the use of beads for wound bed healing. However, the present invention is not limited by the size of bead, the reactive groups found on the beads (e.g., carboxylic acid groups, thiol groups, amine groups, etc.), the cross-linkers used, or the cytoactive factors and other wound healing compositions that are associated with the beads. Indeed, a myriad of combinations of compounds (e.g., small molecule, peptides, proteins, drugs, etc) for wound healing is contemplated for use with beads applied to a wound bed.

In some embodiments, the particles modulate a wound response following an application of an electric or magnetic field to the wound bed. Accordingly, in some embodiments, the particles are charged or magnetized so that the particles migrate or reorganize in an electric or magnetic field. In other embodiments, the beads are dielectric so that the beads experience dielectrophoresis in an AC electrical field. In other embodiments, the beads are magnetic and migrate and/or transmit mechanical forces when exposed to a magnetic field. In other embodiments, the beads are charged so that mechanical forces are applied to the wound bed when an electric field is applied, for example, by placing electrodes on either side of a wound.

In some embodiments, the nano- or micro-beads are applied to the wound by microfluidics printing, microstamping (U.S. Pat. Nos. 5,512,131 and 5,731,152, both of which are incorporated by reference herein in their entirety), or microcontact printing (PCT Publication WO 96/29629, incorporated by reference herein in its entirety). In other embodiments, the nano- or micro-beads are applied to the wound via a pulse jet such as an inkjet printer. Examples of suitable inkjet printers for application of biological fluids include those described in U.S. Pat. No. 7,128,398, WO 95/25116 and WO 98/41531, each of which is incorporated by reference in its entirety. In other embodiments, the nano- or micro-beads are applied by drop dispensers such as the tip of a pin or in an open capillary tube and, touch the pin or capillary tube to the surface of the substrate. Such a procedure is described in U.S. Pat. No. 5,807,522. When the fluid touches the surface, some of the fluid is transferred. In other embodiments, the wound modifying agents are applied be pipetting, micro-pipetting or positive displacement pumps such as the Biodot equipment (available from Bio-Dot Inc., Irvine Calif., USA). In still other embodiments, the nano- or micro-beads are applied to the wound via a microneedle array.

C. Modification with Covalent Modifiers

In some embodiments, the present invention provides for the covalent immobilization of factors to the wound bed. In some preferred embodiments, the covalent modification occurs via homobifunctional or heterobifunctional linkers. In some embodiments, the covalent modifiers are used to directly modify the wound bed by covalently attaching the wound bed. In some embodiments, the covalent modifiers are used to covalently 1, 2, 3, 4 or more different wound active agents to the wound bed. In some embodiments, the covalent modifiers are used to establish gradients of the 1, 2, 3, 4 or more different wound active agents in a vertical or horizontal plane with respect to the wound. In some embodiments, the covalent modifiers are used in conjunction with the polymer layers or beads describes above. In some embodiments, the covalent modifies are used to attach wound active agents to the polymer layers or beads, while in other embodiments, the covalent modifies are used to cross link the polymers or beads.

In some embodiments, the present invention provides methods of treatment, comprising providing a subject having a wound, at least one covalent modification agent and at least one wound active agent, and contacting the wound with the at least one covalent modification agent and the at least one wound active agent under conditions such that the at least one wound active agent is covalently attached to the wound. In some embodiments, the subject is a human. In other embodiments, the subject is a non-human vertebrate.

In some embodiments, the at least one covalent modification agent is a homobifunctional cross-linker. In other embodiments, the at least one covalent modification agent is a heterobifunctional cross-linker. For example, in some embodiments, the homobifunctional cross-linker is an N-hydroxysuccinimidyl ester (e.g., including, but not limited to, disuccinimidyl ester, dithiobis(succinimidylpropionate), 3,3'-dithiobis(sulfosuccinimidylpropionate), disuccinimidyl suberate, bis(sulfosuccinimidyl)suberate, disuccinimidyl tartarate, disulfosuccinimidyl tartarate, bis[2-(succinimidyloxycarbonyloxy)ethyl]sulfone, bis[2-(sulfosuccinimidooxycarbonyloxy)ethyl]sulfone, ethylene glycolbis (succinimidylsuccinate), ethylene glycolbis (sulfosuccinimidylsuccinate), disuccinimidyl glutarate, and N,N'-disuccinimidylcarbonate). In some embodiments, the homobifunctional cross-linker is at a concentration between 1 nanomolar and 10 millimolar. In some preferred embodiments, the homobifunctional cross-linker is at a concentration between 10 micromolar and 1 millimolar. In other embodiments, the at least one covalent modification agent is a heterobifunctional cross-linker (e.g., including, but not limited to, N-succinimidyl 3-(2-pyridyldithio)propionate, succinimidyl 6-(3-[2-pyridyldithio]-propionamido)hexanoate, sulfosuccinimidyl 6-(3'-[2-pyridyldithio]-propionamido) hexanoate, succinimidyloxycarbonyl-α-methyl-α-(2-pyridyldithio)toluene, sulfosuccinimidyl-6-[α-methyl-α-(2-pyridyldithio)toluamido]hexanoate, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxy-sulfosuccinimide ester, N-succinimidyl(4-iodoacetyl)aminobenzoate, sulfosuccinimidyl(4-iodoacetyl)aminobenzoate, succinimidyl-4-(p-maleimidophenyl)butyrate, sulfosuccinimidyl-4-(p-maleimidophenyl)butyrate, N-(γ-maleimidobutyryloxy) succinimide ester, N-(γ-maleimidobutyryloxy) sulfosuccinimide ester, succinimidyl 6-((iodoacetyl)amino) hexanoate, succinimidyl 6-(6-(((4-iodoacetyl)amino) hexanoyl)amino)hexanoate, succinimidyl 4-(((iodoacetyl) amino)methyl)cyclohexane-1-carboxylate, succinimidyl 6-((((4-iodoacetyl)amino)methyl)cyclohexane-1-carbonyl) amino)-hexanoate, and p-nitrophenyl iodoacetate). In some embodiments, the heterobifunctional cross-linker is modified with functional groups, rendering it soluble in aqueous solvents for delivery as an aqueous solution. Furthermore, in some embodiments, the aqueous solution contains additives (e.g., including, but not limited to, surfactants and block copolymers). In other embodiments, a multiplicity of heterobifunctional cross-linkers can be attached to a molecule, polymer or particle to serve as the cross-linking agent. In other embodiments, the heterobifunctional cross-linker is dissolved in an organic solvent (e.g., including, but not limited to, dimethyl sulfoxide).

In some embodiments, the covalent modifier is a photoactivatable crosslinker. Suitable photoactivatable crosslinkers include, but are not limited to, aryl azide N-((2-pyridyldithio) ethyl)-4-azidosalicylamide, 4-azido-2,3,5,6-tetrafluorobenzoic acid, succinimidyl ester, 4-azido-2,3,5,6-tetrafluorobenzoic acid, STP ester, benzophenone maleimide, succinimidyl ester of 4-benzoylbenzoic acid, N-5-Azido-2-Nitrobenzoyloxysuccinimide, N-Hydroxysulfosuccinimidyl-4-azidobenzoate, N-Hydroxysuccinimidyl-4-azidosalicylic acid, and (4-[p-Azidosalicylamido]butylamine).

Referring again to FIG. 2, spatial heterogeneity is depicted in a wound by shapes 720 which depict different chemical moieties found in a wound beds such as amine groups and sulfhydryl groups. Typical areas in a wound will be amine and or sulfhydryl-rich. In some embodiments, a crosslinker (e.g., 230 in FIG. 2) comprising an activated acid is used to react with amine groups, for example nHS (n-hydroxysuccimydal) and a second crosslinker (e.g., 235 in FIG. 2) comprising a malemide is used to react with sulfhydryl groups. In some embodiments, the malimide and activated acid are conjugated to an alkyne so that a uniform surface is presented (e.g., 240 in FIG. 2 where x represents an alkyne group). From this point, widely available click chemistries can be used to add desired wound active agents to the modified surface of the wound. In some embodiments, the wound modifying agent is an azide conjugate or otherwise comprises an azide group and is reacted with the alkyne groups displayed on the wound bed in a Huisgen Cycloaddition.

The present invention also provides kits for treating a subject having a wound, comprising at least one covalent modification agent, at least one wound active agent, and instructions for using the kit to covalently link the at least one wound active agent to the wound. In some embodiments, the at least one covalent modification agent is a homobifunctional cross-linker, heterobifunctional crosslinker, or photoactivatable crosslinker as described above. In some embodiments, the at least one wound active agent includes, but is not limited to, wound active agents described in detail below.

II. Wound Active Agents

In some embodiments, wound active agents are delivered to a wound bed or incorporated into a wound bed using the systems described above. In some embodiments, the wound active agent is bound covalently or non-covalently with the polyelectrolyte layer, bead, non-covalent modifier, etc. The present invention is not limited to a particular mechanism by which the wound active agent binds to the polyelectrolyte layer, bead, non-covalent modifier, etc.

In some embodiments, the polyelectrolyte layer, beads, or non-covalent modifier may function as a drug delivery scaffold to deliver one or more wound active agents to the wound. Wound active agents that may be desirable to deliver include, but are not limited to, trophic factors, extracellular matrices (ECMs), ECM fragments or synthetic constructs, enzymes, enzyme inhibitors, defensins, polypeptides, anti-infective agents (including antimicrobials, antivirals and antifungals), buffering agents, vitamins and minerals, analgesics, anticoagulants, coagulation factors, anti-inflammatory agents, vasoconstrictors, vasodilators, diuretics, and anti-cancer agents. In addition, would active agents include iodine based antimicrobials such as PVP-iodine; selenium based antimicrobials such as 7-azabenzisoselenazol-3(2H)-ones, selenium disulfide, and selenides; and silver based antimicrobials such as silver sulfadiazine. With respect to selenides, with the use of standard and variations of typical protein and carbohydrate attachment chemistries, carboxyl and amino containing selenides may be routinely attached to many polymers, peptides, antibodies, steroids and drugs. Polymers and other molecules with attached selenides generate superoxide in a dose dependent manner in biological solutions, in cells or attached to insoluble matrixes such as silicones.

A wide variety of wound active agents can be incorporated into the polyelectrolyte layer beads, or covalent or non-covalent modifier. The present invention is not limited to a particular mechanism by which one or more wound active agents are released from the polyelectrolyte layer, beads, or covalent or non-covalent modifier into the wound. Indeed, an understanding of the mechanism is not necessary to practice the present invention. Nonetheless, in some embodiments, the present invention contemplates release of the one or more incorporated agents from the polyelectrolyte layer, beads, or non-covalent modifier to the wound by diffusion from the polyelectrolyte layer. In other embodiments, the one or more wound active agents may be released from the polyelectrolyte layer, beads, or non-covalent modifier over time or in response to an environmental condition. The one or more wound active agents may be attached by a degradable linkage, such as a linkage susceptible to degradation via hydrolysis or enzymatic degradation. The linkage may be one that is susceptible to degradation at a certain pH, for example.

In some embodiments, the one or more wound active agents are applied to form a gradient with respect to the wound modifying agent. In general, the gradients present a higher contraction of wound active agent at one or more first desired locations in the wound following application of the wound modifying agent to the wound and a lower concentration of wound active agent at one or second location in the wound following application of the wound modifying agent to the wound. For example, the concentrations of the wound active agents are layered in a wound bed in a gradient such that higher concentrations of a particular composition is greater proximal to the wound bed than distal to the wound bed in a vertical fashion. The converse, where concentrations of compositions is greater distal to the wound bed than proximal, is also contemplated. Concentration of compositions in a wound bed wherein a horizontal gradient is deposited is also contemplated. Topographical gradients are also contemplated, wherein compositions are deposited such that the concentrations of compositions in a wound bed or on a biocompatible particle follow the topography of the substrate, for example, a higher concentration of compositions is deposited in the valleys of undulations of an exemplary substrate compared to the peaks of the undulations.

In some embodiments, the gradient comprises a higher concentration of the wound active agent in the center of the wound modifying agent which transitions to a lower concentration of the wound active agent away from the center of the wound modifying agent. Accordingly, when the wound modifying agent is applied to a wound, the gradient results in a higher concentration of wound active agent in the center of the wound and a lower concentration of wound active agent as one moves to the periphery of the wound. In some embodiments, the gradient comprises a lower concentration of the wound active agent in the center of the wound modifying agent which transitions to a higher concentration of the wound active agent away from the center of the wound modifying agent. Accordingly, the gradient results in a lower concentration of wound active agent in the center of the wound and a higher concentration of wound active agent as one moves to the periphery of the wound. If two or more wound active agents are utilized, they can be presented as similar gradients or the gradients can be varied so that the concentrations of the two or more wound active agents vary across the wound. The gradients of high or low concentration can be any shape, such as circular, square, rectangular, oval, oblong, etc. so that the matrix and gradient can conform to a variety of wound shapes. For example, for long, incision type wound, the gradient may be centered on a longitudinal axis that extends along the length of the wound and can be centered on the wound. As another example, the gradient can be circular or oval-shaped for application to open type wounds, burns, sores and ulcers that are roughly circular or oval. In other embodiments, the gradients comprise a series of features arranged in a pattern. For example, the gradients can form a series of stripes or high and low concentrations of one or more wound active agents along a longitudinal axis of the matrix. Alternatively, the gradients can form a checkerboard pattern, array, concentric circles, overlapping circles or oval, etc.

The present invention contemplates delivery of a wide variety of wound active agents to the wound. In some embodiments, the present invention provides the delivery of trophic factors, including, but not limited to, agrin, amphiregulin, artemin, cardiotrophin-1, epidermal growth factors including EGF; fibroblast growth factors (e.g., FGF-1, FGF-2, FGF-3, FGF-4, FGF-5, FGF-6, and FGF-7); LIF, CSF-1, CSF-2, CSF-3, erythropoietin, endothelial cell growth factors including ECGF; FGF- and ECGF-related growth factors (e.g., endothelial cell stimulating angiogenesis factor, tumor angiogenesis factor, retina-derived growth factor (RDGF), vascular endothelium growth factor (VEGF), brain-derived growth factors (BDGF-A and B), astroglial growth factors (AGF 1 and 2), omentum-derived growth factor, fibroblast-stimulating factor (FSF), and embryonal carcinoma-derived growth factor (ECDGF)); neurotrophic growth factors (e.g., nerve growth factors (NGFs), neurturin, brain-derived neurotrophic factor (BDNF), neurotrophin-3, neurotrophin-4, and ciliary neurotrophic factor (CNTF)); glial growth factors (e.g., GGF-I, GGF-II, GGF-III, glia maturation factor (GMF), and glial-derived neurotrophic factor (GDNF)); liver growth factors (e.g., hepatopoietin A, hepatopoietin B, and hepatocyte growth factors including HGF); prostate growth factors including prostate-derived growth factors (PGFs); mammary growth factors including mammary-derived growth factor 1 (MDGF-1) and mammary tumor-derived factor (MTGF); heart growth factors including nonmyocyte-derived growth factor (NMDGF); melanocyte growth factors including melanocyte-stimulating hormone (MSH) and melanoma growth-stimulating activity (MGSA); angiogenic factors (e.g., angiogenin, angiotropin, platelet-derived ECGF, VEGF, and pleiotrophin); transforming growth factors including TGF-α and TGF-β; TGF-like growth factors (e.g., TGF-beta$_1$, TGF-beta$_2$, TGF-beta$_3$, GDF-1, CDGF, tumor-derived TGF-like factors, ND-TGF, and human epithelial transforming factor); regulatory peptides with growth factor-like properties (e.g., bombesin and bombesin-like peptides ranatensin and litorin, angiotensin, endothelin, atrial natriuretic factor, vasoactive intestinal peptide, and bradykinin); platelet-derived growth factors including PDGF-A, PDGF-B, and PDGF-AB; neuropeptides (e.g., substance P, calcitonin gene-regulated peptide (CGRP), and neuropeptide Y); neurotransmitters and their analogs including norepinephrine, acetylcholine and carbachol; hedgehog, heregulin/neuregulin, IL-1, osteoclast-activating factor (OAF), lymphocyte-activating factor (LAF), hepatocyte-stimulating factor (HSF), B-cell-activating factor (BAF), tumor inhibitory factor 2 (TIF-2), keratinocyte-derived T-cell growth factor (KD-TCGF), IL-2, IL-3, IL-4, IL-5, IL-6, IL-7, IL-8, IL-9, IL-10, IL-11, stromal cell-derived cytokine (SCDC), IL-12, IL-13, IL-14, IL-15, insulin, insulin-like growth factors including IGF-1, IGF-2, and IGF-BP; interferons including INF-alpha, INF-beta, and INF-gamma; leptin, midkine, tumor necrosis factors (TNF-alpha and beta), netrins, saposins, semaphorins, somatrem, somatropin, stem cell factor, VVGF, bone morphogenetic proteins (BMPs), adhesion molecules, other cytokines, heparin-binding growth factors, and tyrosine kinase receptor ligands. In some embodiments, the wound active agent is a peptide such as AcEEED, which is the N terminal peptide for alpha smooth muscle actin and has been shown to inhibit contractile properties of myofibroblasts.

In some embodiments, the present invention provides the delivery of ECMs, including, but not limited to native constructs, fragments of native constructs and synthetic analogs of: extracellular matrix proteins, reconstituted basement membrane-like complexes derived from eukaryotic cell lines, collagens, fibronectin, laminin, VCAM-1, vitronectin and gelatin, a bacterial extracellular matrix, a gel matrix, and polymeric matrices. In some embodiments, the wound active agents are integrin binding sequences exemplified by, but not limited to RGD, EILDV, VCAM-1 and their recombined or synthetic analogs, enzymes, enzyme inhibitors, and polypeptides.

In some embodiments, the present invention provides the delivery of enzymes, including, but not limited to, exopeptidases and endopeptidases (also known as proteases and proteinases), including but not limited to the serine proteinases chymotrypsin, trypsin, elastase, and kallikrein, bacterial enzymes, the cysteine proteases papain, actinin, bromelain, cathepsins, cytosolic calpains, parasitic proteases, aspartic proteinases, the pepsin family of proteases pepsin and chymosin, lysosomal cathepsins D, renin, fungal proteases, the viral proteases, AIDS virus retropepsin, and the metalloproteinases (MMPs), collagenases, MMP1, MMP2, MMP8, MMP13, gelatinases, MMP2, MMP9, MMP3, MMP7, MMP10, MMP11, and MMP12.

In some embodiments, the present invention provides the delivery of enzyme inhibitors, including, but not limited to captopril, thiorphan, phosphoramidon, teprotide, protease and proteinase inhibitors, metalloproteinase inhibitors and exopeptidase inhibitors.

In some embodiments, the present invention provides the delivery of defensins, including, but not limited to, alpha-defensins HNP 1, 2, 3 and 4, and beta-defensins HBD-1 and HBD-2.

In some embodiments, the present invention provides the delivery of polypeptides, including, but not limited to, fibronectin, serotonin, PAF, PDEGF, TNFa, IL1, IL6, IGF, IGF-1, IGF-2, IL-1, PDGF, FGF, KGF, VEGF, bradykinin, prothymosin-alpha, and thymosin-alpha1.

In some embodiments, the present invention provides the delivery of antimicrobials, including, but not limited to, magainin (e.g., magainin I, magainin II, xenopsin, xenopsin precursor fragment, caerulein precursor fragment), magainin I and II analogs (e.g., PGLa, magainin A, magainin G, pexiganin, Z-12, pexigainin acetate, D35, MSI-78A, MG0 (K10E, K11E, F12W-magainin 2), MG2+ (K10E, F12W-magainin-2), MG4+ (F12W-magainin 2), MG6+ (f12W, E19Q-magainin 2 amide), MSI-238, reversed magainin II analogs (e.g., 53D, 87-ISM, and A87-ISM), Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME(1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 ((+/−) 1-(4-aminobutyl)-6-benzylindane), PM2c ((+/−)-6-benzyl-1-(3-carboxypropyl)indane), PM3 ((+/−)1-benzyl-6-(4-aminobutyl)indane), tachyplesin, buforin I or II, misgurin, melittin, PR-39, PR-26, 9-phenylnonylamine, (KLAKKLA)n, (KLAKLAK)n, where n=1, 2, or 3, (KALKALK)3, KLGKKLG)n, and KAAKKAA)n, wherein N=1, 2, or 3, paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysin, thionin, hevein and knottin-like peptides, MPG1, 1bAMP, snakin, lipid transfer proteins, and plant defensins. Exemplary sequences for the above compounds are provided in Table 1. In some embodiments, the antimicrobial peptides are synthesized from L-amino acids, while in other embodiments, the peptides are synthesized from, or comprise, D-amino acids. Additional antimicrobial polypeptides of use in the present invention are listed in FIG. 7.

TABLE 1

Antimicrobial Peptides

| SEQ ID NO: | Name | Organism | Sequence |
|---|---|---|---|
| 1 | lingual antimicrobial peptide precursor (Magainin) | Bos taurus | mrlhhlllallflvlsagsgftqgvrnsqscrrnkgicvp ircpgsmrqigtclgaqvkccrrk |
| 2 | antimicrobial peptide PGQ | Xenopus laevis | gvlsnvigylkklgtgalnavlkq |
| 3 | Xenopsin | Xenopus laevis | mykgiflcvllavicanslatpssdadedndeveryvrgw askigqtlgkiakvglkeliqpkreamlrsaeaqgkrpwil |
| 4 | magainin precursor | Xenopus laevis | mfkglficsliavicanalpqpeasadedmderevrgigk flhsagkfgkafvgeimkskrdaeavgpeafadedldere vrgigkflhsakkfgkafvgeimnskrdaeavgpeafade dlderevrgigkflhsakkfgkafvgeimnskrdaeavgp eafadedlderevrgigkflhsakkfgkafvgeimnskrd aeavgpeafadedfderevrgigkflhsakkfgkafvgei mnskrdaeavgpeafadedlderevrgigkflhsakkfgk afvgeimnskrdaeavddrrwve |

TABLE 1-continued

Antimicrobial Peptides

| SEQ ID NO: | Name | Organism | Sequence |
|---|---|---|---|
| 5 | tachyplesin I | Tachypleus gigas | kwcfrvcyrgicyrrcr |
| 6 | tachyplesin II | Tachypleus gigas | rwcfrvcyrgicyrkcr |
| 7 | buforin I | Bufo bufo gagarizans | msgrgkqggkvrakaktrssraglqfpvgrvbrllrkgny aqrvgagapvylaavleyltaeilelagnaardnkktrii prhlqlavrndeelnkllggvtiaqggvlpniqavllpkt esskpaksk |
| 8 | buforin II | Bufo bufo gagarizans | trssraglqfpvgrvhrllrk |
| 9 | cecropin A | Bombyx mori | mnfvrilsfvfalvlalgavsaapeprwklfkkiekvgrn vrdglikagpaiavigqakslgk |
| 10 | cecropin B | Bombyx mori | mnfakilsfvfalvlalsmtsaapeprwkifkkiekmgrn irdgivkagpaievlgsakaigk |
| 11 | cecropin C | Drosophila melanogaster | mnfykifvfvalilaisigqseagwlkklgkrierigqht rdatiqglgiaqqaanvaatarg |
| 12 | cecropin P1 | Sus scrofa | swlsktakklensakkrisegiaiaiqggpr |
| 13 | indolicidin | Bos taurus | ilpwkwpwwpwrr |
| 14 | nisin | Lactococcus lactis | itsislctpgcktgalmgcnmktatchcsihvsk |
| 15 | ranalexin | Rana catesbeiana | flgglikivpamicavtkkc |
| 16 | lactoferricin B | Bos taurus | fkcrrwqwrmkklgapsitcvrraf |
| 17 | protegrin-1 | Sus scrofa | rggrlcycrrrfcvcvgrx |
| 18 | protegrin-2 | Sus scrofa | ggrlcycrrrfcicvg |
| 19 | histatin precursor | Homo sapiens | mkffvfalilalmlsmtgadshakrhhgykrkfhekhhsh rgyrsnylydn |
| 20 | histatin 1 | Macaca fascicularis | dsheerhhgrhghhkygrkfhekhhshrgyrsnylydn |
| 21 | dermaseptin | Phyllomedusa sauvagei | alwktmlkklgtmalhagkaalgaaadtisqtq |
| 22 | dermaseptin 2 | Phyllomedusa sauvagei | alwftmlkklgtmalhagkaalgaaantisqgtq |
| 23 | dermaseptin 3 | Phyllomedusa sauvagei | alwknmlkgigklagkaalgavkklvgaes |
| 24 | misgurin | Misgurnus anguillicaudatus | rqrveelskfskkgaaarrrk |
| 25 | melittin | Apis mellifera | gigavlkvlttglpaliswisrkkrqq |
| 26 | pardaxin-1 | Pardachirus pavoninus | gffalipkiissplfktllsavgsalsssgeqe |
| 27 | pardaxin-2 | Pardachirus pavoninus | gffalipkiisspifktllsavgsalsssggqe |
| 28 | bactenecin 5 precursor | Bos taurus | metqraslslgrcslwllllglvlpsasaqalsyreavlr avdqfnersseanlyrlleldptpnddldpgtrkpvsfrv ketdcprtsqqpleqcdfkenglvkqcvgtvtldpsndqf dincnelqsvrfrppirrppirppfyppfrppirppifpp irppfrpplgpfpgrr |
| 29 | bactenecin precursor | Bos taurus | metpraslslgrwslwllllglalpsasaqalsyreavlr avdqlneqssepniyrlleldqppqddedpdspkrvsfrv |

TABLE 1-continued

Antimicrobial Peptides

| SEQ ID NO: | Name | Organism | Sequence |
|---|---|---|---|
| | | | ketvcsrttqqppeqcdfkengllkrcegtvtldqvrgnf ditcnnhqsiritkqpwappqaarlcrivvirvcr |
| 30 | ceratotoxin A | Ceratitis capitata | sigsalkkalpvakkigkialpiakaalp |
| 31 | ceratotoxin B | Ceratitis capitata | sigsafkkalpvakkigkaalpiakaalp |
| 32 | cathelicidin antimicrobial peptide | Homo sapiens | mktqrnghslgrwslvlllllglvmplaiiaqvlsykeavl raidginqrssdanlyrlldldprptmdgdpdtpkpvsft vketvcprttqqspedcdfkkdglvkrcmgtvtlnqargs fdiscdkdnkrfallgdffrkskekigkefkrivqrikdf lrnlvprtes |
| 33 | myeloid cathelicidin 3 | Equus caballus | metqrntrclgrwsplllllglvippattqalsykeavlr avdglnqrssdenlyrlleldplpkgdkdsdtpkpvsfmv ketvcprimkqtpeqcdfkenglvkqcvgtvildpvkdyf dascdepqrvknfhsvgsliqrhqqmirdkseatrhgiri itrpklllas |
| 34 | myeloid antimicrobial peptide BMAP-28 | Bos taurus | metqraslslgrwslwllllglalpsasaqalsyreavlr avdqlnekssseanlyrlleldpppkeddenpnipkpvsfr vketvcprtsqqspeqcdfkengllkecvgtvtldqvgsn fditcavpqsvgglrslgrkilrawkkygpiivpiirig |
| 35 | myeloid cathelicidin 1 | Equus caballus | metqrntrclgrwsplllllglvippattqalsykeavlr avdglnqrssdenlyrlleldplpkgdkdsdtpkpvsfmv ketvcprimkqtpeqcdfkenglvkqcvgtvilgpvkdhf dvscgepqrvkrfgrlaksflrmrillprrkillas |
| 36 | SMAP 29 | Ovis aries | metqraslslgrcslwllllglalpsasaqvlsyreavlr aadqlnekssseanlyrlleldpppkqddensnipkpvsfr vketvcprtsqqpaeqcdfkengllkecvgtvtldqvrnn fditcaepqsvrglrrlgrkiahgvkkygptvlriiriag |
| 37 | BNP-1 | Bos taurus | rlcrivvirvcr |
| 38 | HNP-1 | Homo sapiens | acycripaciagerrygtciyqgrlwafcc |
| 39 | HNP-2 | Homo sapiens | cycripaciagerrygtciyqgrlwafcc |
| 40 | HNP-3 | Homo sapiens | dcycripaciagerrygtciyqgrlwafcc |
| 41 | HNP-4 | Homo sapiens | vcscrlvfcrrtelrvgncliggvsftycctrv |
| 42 | NP-1 | Oryctolagus cuniculus | vvcacrralclprerragfcrirgrihplccrr |
| 43 | NP-2 | Oryctolagus cuniculus | vvcacrralclplerragfcrirgrihplccrr |
| 44 | NP-3A | Oryctolagus cuniculus | gicacrrrfcpnserfsgycrvngaryvrccsrr |
| 45 | NP-3B | Oryctolagus cuniculus | grcvcrkqllcsyrerrigdckirgvrfpfccpr |
| 46 | NP-4 | Oryctolagus cuniculus | vsctcrrfscgfgerasgsctvnggvrhtlccrr |
| 47 | NP-5 | Oryctolagus cuniculus | vfctcrgflcgsgerasgsctingvrhtlccrr |
| 48 | RatNP-1 | Rattus norvegicus | vtcycrrtrcgfrerlsgacgyrgriyrlccr |
| 49 | Rat-NP-3 | Rattus norvegicus | cscrysscrfgerlllsgacrlngriyrlcc |
| 50 | Rat-NP-4 | Rattus norvegicus | actcrigacvsgerltgacglngriyrlccr |

TABLE 1-continued

Antimicrobial Peptides

| SEQ ID NO: | Name | Organism | Sequence |
|---|---|---|---|
| 51 | GPNP | Guinea pig | rrcicttrtcrfpyrrlgtcifqnrvytfcc |
| 52 | beta defensin-3 | Homo sapiens | mrihyllfallflflvpvpghggiintlqkyycrvrggrc avlsclpkeeqigkcstrgrkccrrkk |
| 53 | theta defensin-1 | Macaca mulatta | rcictrgfcrclcrrgvc |
| 54 | defensin CUA1 | Helianthus annuus | mkssmkmfaalllvvmcllanemggplvveartcesqshk fkgtclsdtncanvchserfsggkcrgfrrrcfctthc |
| 55 | defensin SD2 | Helianthus annuus | mkssmkmfaalllvvmcllanemggplvveartcesqshk fkgtclsdtncanvchserfsggkcrgfrrrcfctthc |
| 56 | neutrophil defensin 2 | Macaca mulatta | acycripaclagerrygtcfymgrvwafcc |
| 57 | 4 KDA defensin | Androctonus australis hector | gfgcpfnqgacbrhcrsirrrggycaglfkqtctcyr |
| 58 | defensin | Mytilus galloprovincialis | gfgcpnnyqcbrhcksipgrcggycggxhrlrctcyrc |
| 59 | defensin AMP1 | Heuchera sanguinea | dgvklcdvpsgtwsghcgssskcsqqckdrehfayggach yqfpsvkcfckrqc |
| 60 | defensin AMP1 | Clitoria ternatea | nlcerasltwtgncgntghcdtqcrnwesakhgachkrgn wkcfcyfnc |
| 61 | cysteine-rich cryptdin-1 homolog | Mus musculus | mkklvllfalvllafqvqadsiqntdeetkteeqpgekdq avsvsfgdpqgsalqdaalgwgrrcpqcprcpscpscprc prcprckcnpk |
| 62 | beta-defensin-9 | Bos taurus | qgvrnfvtcrinrgfcvpircpgbrrqigtclgpqikccr |
| 63 | beta-defensin-7 | Bos taurus | qgvrnfvtcrinrgfcvpircpgbrrqigtclgprikccr |
| 64 | beta-defensin-6 | Bos taurus | qgvrnhvtcriyggfcvpircpgrtrqigtcfgrpvkccrrw |
| 65 | beta-defensin-5 | Bos taurus | qvvrnpqscrwnmgvcipiscpgnmrqigtcfgprvpccr |
| 66 | beta-defensin-4 | Bos taurus | qrvrnpqscrwnmgvcipflcrvgmrqigtcfgprvpccrr |
| 67 | beta-defensin-3 | Bos taurus | qgvrnhvtcrinrgfcvpircpgrtrqigtcfgprikccrsw |
| 68 | beta-defensin-10 | Bos taurus | qgvrsylscwgnrgiclnrcpgrmrqigtclaprvkccr |
| 69 | beta-defensin-13 | Bos taurus | sgisgplscgrnggvcipircpvpmrqigtcfgrpvkccrsw |
| 70 | beta-defensin-1 | Bos taurus | dfaschtnggiclpnrcpghmiqigicfrprvkccrsw |
| 71 | coleoptericin | Zophobas atratus | slqggapnfpqpsqqnggwqvspdlgrddkgntrgqieiq nkgkdhdfnagwgkvirgpnkakptwhvggtyrr |
| 72 | beta defensin-3 | Homo sapiens | mrihyllfallflflvpvpghggiintlqkyycrvrggrc avlsclpkeeqigkcstrgrkccrrkk |
| 73 | defensin C | Aedes aegypti | atcdllsgfgvgdsacaahciargnrggycnskkvcvcrn |
| 74 | defensin B | Mytilus edulis | gfgcpndypchrhcksipgryggycggxhrlrctc |
| 75 | sapecin C | Sarcophaga peregrina | atcdllsgigvqhsacalhcvfrgnrggyctgkgicvcrn |
| 76 | macrophage antibiotic peptide MCP-1 | Oryctolagus cuniculus | mrtlallaaillvalqaqaehvsvsidevvdqqppqaedq dvaiyvkehessalealgvkagvvcacrralclprerrag fcrirgrihplccrr |
| 77 | cryptdin-2 | Mus musculus | mkplvllsalvllsfqvqadpiqntdeetkteeqsgeedq avsvsfgdregaslqeeslrdlvcycrtrgckrrermngt crkghlmytlcc |
| 78 | cryptdin-5 | Mus musculus | mktfvllsalvllafqvqadpibktdeetnteeqpgeedq avsisfggqegsalheelskklicycrirgckrrervfgt crnlfltfvfccs |

TABLE 1-continued

Antimicrobial Peptides

| SEQ ID NO: | Name | Organism | Sequence |
|---|---|---|---|
| 79 | cryptdin 12 | Mus musculus | lrdlvcycrargckgrermngtcrkghllymlccr |
| 80 | defensin | Pyrrhocoris apterus | atcdilsfqsqwvtpnhagcalhcvikgykggqckitvchcrr |
| 81 | defensin R-5 | Rattus norvegicus | vtcycrstrcgfrerlsgacgyrgriyrlccr |
| 82 | defensin R-2 | Rattus norvegicus | vtcscrtsscrfgerlsgacrlngriyrlcc |
| 83 | defensin NP-6 | Oryctolagus cuniculus | gicacrrrfclnfeqfsgycrvngaryvrccsrr |
| 84 | beta-defensin-2 | Pan troglodytes | mrvlyllfsflfiflmplpgvfggisdpvtclksgaichp vfcprrykqigtcglpgtkcckkp |
| 85 | beta-defensin-2 | Homo sapiens | mrvlyllfsflfiflmplpgvfggigdpvtclksgaichp vfcprrykqigtcglpgtkcckkp |
| 86 | beta-defensin-1 | Homo sapiens | mrtsylllftlclllsemasggnfltglghrsdhyncvss ggqclysacpiftkiqgtcyrgkakcck |
| 87 | beta-defensin-1 | Capra hircus | mrlhhlllvlfflvlsagsgftqgirsrrschrnkgvcal trcpmmrqigtcfgppvkccrkk |
| 88 | beta defensin-2 | Capra hircus | mrlhhlllalfflvlsagsgftqgiinhrscyrnkgvcap arcprnmrqigtchgppvkccrkk |
| 89 | defensin-3 | Macaca mulatta | mrtlvilaaillvalqaqaeplqartdeataaqeqiptdn pevvvslawdeslapkdsvpglrknmacycripaclager rygtcfyrrrvwafcc |
| 90 | defensin-1 | Macaca mulatta | mrtlvilaaillvalqaqaeplqartdeataaqeqiptdn pevvvslawdeslapkdsvpglrknmacycripaclager rygtcfylgrvwafcc |
| 91 | neutrophil defensin 1 | Mesocricetus auratus | vtcfcrrrgcasrerhigycrfgntiyrlccrr |
| 92 | neutrophil defensin 1 | Mesocricetus auratus | cfckrpvcdsgetqigycrlgntfyrlccrq |
| 93 | Gallinacin 1-alpha | Gallus gallus | grksdcfrkngfcaflkcpyltlisgkcsrfhlcckriw |
| 94 | defensin | Allomyrina dichotoma | vtcdllsfeakgfaanhslcaahclaigrrggscergvcicrr |
| 95 | neutrophil cationic peptide 1 | Cavia porcellus | rrcicttrtcrfpyrrlgtcifqnrvytfcc |

In some embodiments, the present invention provides the delivery of antimicrobials, including, but not limited to, loracarbef, cephalexin, cefadroxil, cefixime, ceftibuten, cefprozil, cefpodoxime, cephradine, cefuroxime, cefaclor, neomycin/polymyxin/bacitracin, dicloxacillin, nitrofurantoin, nitrofurantoin macrocrystal, nitrofurantoin/nitrofuran mac, dirithromycin, gemifloxacin, ampicillin, gatifloxacin, penicillin V potassium, ciprofloxacin, enoxacin, amoxicillin, amoxicillin/clavulanate potassium, clarithromycin, levofloxacin, moxifloxacin, azithromycin, sparfloxacin, cefdinir, ofloxacin, trovafloxacin, lomefloxacin, methenamine, erythromycin, norfloxacin, clindamycin/benzoyl peroxide, quinupristin/dalfopristin, doxycycline, amikacin sulfate, vancomycin, kanamycin, netilmicin, streptomycin, tobramycin sulfate, gentamicin sulfate, tetracyclines, framycetin, minocycline, nalidixic acid, demeclocycline, trimethoprim, miconazole, colistimethate, piperacillin sodium/tazobactam sodium, paromomycin, colistin/neomycin/hydrocortisone, amebicides, sulfisoxazole, pentamidine, sulfadiazine, clindamycin phosphate, metronidazole, oxacillin sodium, nafcillin sodium, vancomycin hydrochloride, clindamycin, cefotaxime sodium, co-trimoxazole, ticarcillin disodium, piperacillin sodium, ticarcillin disodium/clavulanate potassium, neomycin, daptomycin, cefazolin sodium, cefoxitin sodium, ceftizoxime sodium, penicillin G potassium and sodium, ceftriaxone sodium, ceftazidime, imipenem/cilastatin sodium, aztreonam, cinoxacin, erythromycin/sulfisoxazole, cefotetan disodium, ampicillin sodium/sulbactam sodium, cefoperazone sodium, cefamandole nafate, gentamicin, sulfisoxazole/phenazopyridine, tobramycin, lincomycin, neomycin/polymyxin B/gramicidin, clindamycin hydrochloride, lansoprazole/clarithromycin/amoxicillin, alatrofloxacin, linezolid, bismuth subsalicylate/metronidazole/tetracycline, erythromycin/benzoyl peroxide, mupirocin, fosfomycin, pentamidine isethionate, imipenem/cilastatin, troleandomycin, gatifloxacin, chloramphenicol, cycloserine, neomycin/polymyxin B/hydrocortisone, ertapenem, meropenem, cephalosporins, fluconazole, cefepime, sulfamethoxazole, sulfamethoxazole/trimethoprim, neomycin/polymyxin B, penicillins, rifampin/isoniazid, erythromycin estolate, erythromycin ethylsuccinate, erythromycin stearate, ampicillin trihydrate, ampicillin/probenecid, sulfasalazine, sulfanilamide, sodium sulfacetamide, dapsone, doxycycline hyclate, trimenthoprim/sulfa, methenamine mandelate, plasmodicides, pyrimethamine, hydroxychloroquine, chloroquine phosphate, trichomonocides, anthelmintics, atovaquone, bacitracin, bacitracin/polymyxin b, gentamycin, neomycin/polymyxin/dexameth, neomycin sulf/dexameth, sulfacetamide/prednisolone, sulfacetamide/phenylephrine, tobramycin sulfate/dexameth, silver ion compounds, and silver containing compounds such as silver sulfadiazine and related compounds In some embodiments, the present invention provides the delivery of antivirals, including, but not limited to, amantadine, acyclovir, foscarnet, indinavir, ribavirin, enfuvirtide, emtricitabine, lamivudine, abacavir sulfate, fomivirsen, valacyclovir, tenofovir, cidofovir, atazanavir, amprenavir, delavirdine mesylate, famciclovir, adefovir, didanosine, efavirenz, trifluridine, inidinavir, lamivudine, vidarabine, lopinavir/ritonavir, ganciclovir, zanamivir, abacavir/lamivudine/zidovudine, lamivudine/zidovudine, nelfinavir, nelfinavir mesylate, nevirapine, ritonavir, saquinavir, saquinavir mesylate, rimantadine, stavudine, docosanol, zalcitabine, idoxuridine, zidovudine, zidovudine/didanosine, valganciclovir, penciclovir, lamivudine, and oseltamivir.

In some embodiments, the present invention provides the delivery of antifungals, including, but not limited to, amphotericin B, nystatin, nystatin/triamcinolone, itraconazole, ketoconazole, miconazole, sulconazole, clotrimazole, clotrimazole/betamethasone, enilconazole, econazole, oxiconazole, tioconazole, terconazole, butoconazole, thiabendazole, flucytosine, butenafine, ciclopirox, haloprogin, naftifine, tolnaftate, natamycin, undecylenic acid, mafenide, dapsone, clioquinol, clioquinol/hydrocortisone, potassium iodide, silver sulfadiazine, gentian violet, carbol-fuchsin, cilofungin, sertaconazole, voriconazole, fluconazole, terbinafine, caspofungin, other topical azole drugs, and griseofulvin.

In some embodiments, the present invention provides the use and delivery of buffering agents, including, but not limited to, Maleic acid, Phosphoric acid, Glycine, Chloroacetic acid, Formic acid, Benzoic acid, Acetic acid, Pyridine, piperazine, MES, Bis-tris, Carbonate, ACES, ADA MOPSO, PIPES, Phosphoric acid, BES, MOPS, TES, HEPES, DIPSO, TAPSO, Triethanolamine, HEPSO, Tris, Tricine, Bicine, TAPS, Borate, Ammonia, CHES, Ethanolamine, CAPSO, Glycine, Carbonate, CAPS, Methylamine, Piperidine, and Phosphoric acid.

In some embodiments, the present invention provides the delivery of vitamins and minerals, including, but not limited to, Vitamin A, Carotenoids, Vitamin D, Vitamin E, Vitamin K, Vitamin C/ascorbic acid, B1/thiamin, B2/riboflavin, B3/niacin, B5/pantothenic acid, B6/pyridoxine, B12/cobalamin, Biotin, Calcium, Magnesium, Phosphorus, Sodium, Chloride, Potassium, Boron, Chromium, Copper, Iodine, Iron, Manganese, Selenium, and Zinc.

In some embodiments, the present invention provides the delivery of analgesics, including, but not limited to, acetaminophen, anileridine, acetylsalicylic acid, buprenorphine, butorphanol, fentanyl, fentanyl citrate, codeine, rofecoxib, hydrocodone, hydromorphone, hydromorphone hydrochloride, levorphanol, alfentanil hydrochloride, meperidine, meperidine hydrochloride, methadone, morphine, nalbuphine, opium, levomethadyl, hyaluronate sodium, sufentanil citrate, capsaicin, tramadol, leflunomide, oxycodone, oxymorphone, celecoxib, pentazocine, propoxyphene, benzocaine, lidocaine, dezocine, clonidine, butalbital, phenobarbital, tetracaine, phenazopyridine, sulfamethoxazole/phenazopyridine, and sulfisoxazole/phenazopyridine.

In some embodiments, the present invention provides the delivery of anticoagulants, including, but not limited to, coumarins, 1,3-indandione, anisindione, fondaparinux, heparin, lepirudin, antithrombin, warfarin, enoxaparin, dipyridamole, dalteparin, ardeparin, nadroparin, and tinzaparin.

In some embodiments, the present invention provides the delivery of coagulation factors, including, but not limited to, Factor I (fibrinogen), Factor II (prothrombin), Factor III (thromboplastin, tissue factor), Factor IV (calcium), Factor V (labile factor), Factor VII (stable factor), Factor VIII (antihemophilic globulin, antihemophilic globulin, antihemophilic factor A), Factor IX (plasma thromboplastin component, Christmas factor, antihemophilic factor B), Factor X (Stuart factor, Prower factor, Stuart-Prower factor), Factor XI (plasma thromboplastin antecedent, antihemophilic factor C), Factor XII (Hageman factor, surface factor, contact factor), and Factor XIII (fibrin stabilizing factor, fibrin stabilizing enzyme, fibri-nase).

In some embodiments, the present invention provides the delivery of anti-inflammatory agents, including, but not limited to, non steroidal anti-inflammatory drugs (NSAIDs) including diclofenac (also known as Voltaren, Abitren, Allvoran, Almiral, Alonpin, Anfenax, Artrites, Betaren, Blesin, Bolabomin, Cataflam, Clofec, Clofen, Cordralan, Curinflam, Diclomax, Diclosian, Dicsnal, Difenac, Ecofenac, Hizemin, Inflamac, Inflanac, Klotaren, Lidonin, Monoflam, Naboal, Oritaren, Remethan, Savismin, Silino, Staren, Tsudohmin, Voltarol, Voren, Voveran, and Vurdon), diflunisal (also known as Dolobid, Adomal, Diflonid, Diflunil, Dolisal, Dolobis, Dolocid, Donobid, Dopanone, Dorbid, Dugodol, Flovacil, Fluniget, Fluodonil, Flustar, Ilacen, Noaldol, Reuflos, and Unisal), etodolac (also known as Lodine), fenoprofen (also known as Nalfon, Fenoprex, Fenopron, Fepron, Nalgesic, and Progesic), flurbiprofen (also known as Ansaid and Ocuflur), ibuprofen (also known as Rufen, Motrin, Aches-N-Pain, Advil, Nuprin, Dolgesic, Genpril, Haltran, Ibifon, Ibren, Ibumed, Ibuprin, Ibupro-600, Ibuprohm, Ibu-Tab, Ibutex, Ifen, Medipren, Midol 200, Motrin-IB, Cramp End, Profen, Ro-Profen, Trendar, Alaxan, Brofen, Alfam, Brufen, Algofen, Brufort, Amersol, Bruzon, Andran, Buburone, Anflagen, Butacortelone, Apsifen, Deflem, Artofen, Dolgit, Artril, Dolocyl, Bloom, Donjust, Bluton, Easifon, Ebufac, Emflam, Emodin, Fenbid, Fenspan, Focus, Ibosure, Ibufen, Ibufug, Ibugen, Ibumetin, Ibupirac, Imbun, Inabrin, Inflam, Irfen, Librofen, Limidon, Lopane, Mynosedin, Napacetin, Nobafon, Nobgen, Novogent, Novoprofen, Nurofen, Optifen, Paduden, Paxofen, Perofen, Proartinal, Prontalgin, Q-Profen, Relcofen, Remofen, Roidenin, Seclodin, Tarein, and Zofen), indomethacin (also known as Indameth, Indocin, Amuno, Antalgin, Areumatin, Argilex, Artherexin, Arthrexin, Artrinovo, Bavilon, Bonidon, Boutycin, Chrono-Indocid, Cidalgon, Confortid, Confortind, Domecid, Durametacin, Elemetacin, Idicin, Imbrilon, Inacid, Indacin, Indecin, Indocap, Indocen, Indocid, Indoflex, Indolag, Indolar, Indomed, Indomee, Indometacinum, Indometicina, Indometin, Indovis, Indox, Indozu, Indrenin, Indylon, Inflazon, Inpan, Lauzit, Liometace, Metacen, Metindon, Metocid, Mezolin, Mobilan, Novomethacin, Peralgon, Reflox, Rheumacid, Rheumacin, Salinac, Servindomet, Toshisan, and Vonum), ketoprofen (also known as Orudis, Alrheumat, Alrheumun, Alrhumat, Aneol, Arcental, Dexal, Epatec, Fastum, Keduril, Kefenid, Keprofen, Ketofen, Ketonal, Ketosolan, Kevadon, Mero, Naxal, Oruvail, Profenid, Salient, Tofen, and Treosin), ketorolac (also known as Toradol), meclofenamate (also known as Meclofen, Meclomen, and Movens), mefenamic acid (also known as Ponstel, Alpain, Aprostal, Benostan, Bonabol, Coslan, Dysman, Dyspen, Ecopan, Lysalgo, Manic, Mefac, Mefic, Mefix, Parkemed, Pondex, Ponsfen, Ponstan, Ponstyl, Pontal, Ralgec, and Youfenam), nabumetone (also known as Relafen), naproxen (also known as Naprosyn, Anaprox, Aleve, Apranax, Apronax, Arthrisil, Artrixen, Artroxen, Bonyl, Congex, Danaprox, Diocodal, Dysmenalgit, Femex, Flanax, Flexipen, Floginax, Gibixen, Headlon, Laraflex, Laser, Leniartil, Nafasol, Naixan, Nalyxan, Napoton, Napren, Naprelan, Naprium, Naprius, Naprontag, Naprux, Napxen, Narma, Naxen, Naxid, Novonaprox, Nycopren, Patxen, Prexan, Prodexin, Rahsen, Roxen, Saritilron, Sinartrin, Sinton, Sutony, Synflex, Tohexen, Veradol, Vinsen, and Xenar), oxaprozin (also known as Daypro), piroxicam (also known as Feldene, Algidol, Antiflog, Arpyrox, Atidem, Bestocam, Butacinon, Desinflam, Dixonal, Doblexan, Dolonex, Feline, Felrox, Fuldin, Indene, Infeld, Inflamene, Lampoflex, Larapam, Medoptil, Novopirocam, Osteral, Pilox, Piraldene, Piram, Pirax, Piricam, Pirocam, Pirocaps, Piroxan, Piroxedol, Piroxim, Piton, Posidene, Pyroxy, Reucam, Rexicam, Riacen, Rosic, Sinalgico, Sotilen, Stopen, and Zunden), sulindac (also known as Clinoril, Aflodac, Algocetil, Antribid, Arthridex, Arthrocine, Biflace, Citireuma, Clisundac, Imbaral, Lindak, Lyndak, Mobilin, Reumofil, Sudac, Sulene, Sulic, Sulindal, Suloril, and Sulreuma), tolmetin (also known as Tolectin, Donison, Midocil, Reutol, and Safitex), celecoxib (also known as Celebrex), meloxicam (also known as Mobic), rofecoxib (also known as Vioxx), valdecoxib (also known as Bextra), aspirin (also known as Anacin, Ascriptin, Bayer, Bufferin, Ecotrin, and Excedrin) and steroidal anti-inflammatory drugs including cortisone, prednisone and dexamethasone.

In some embodiments, the present invention provides the delivery of vasoconstrictors, including, but not limited to, epinephrine (adrenaline, Susphrine), phenylephrine hydrochloride (Neo-Synephrine), oxymetazoline hydrochloride (Afrin), norepinephrine (Levophed), and caffeine.

In some embodiments, the present invention provides the delivery of vasodilators, including, but not limited to, bosentan (Tracleer), epoprostenol (Flolan), treprostinil (Remodulin), sitaxsentan, nifedipine (Adalat, Procardia), nicardipine (Cardene), verapamil (Calan, Covera-HS, Isoptin, Verelan), diltiazem (Dilacor XR, Diltia XT, Tiamate, Tiazac, Cardizem), isradipine (DynaCirc), nimodipine (Nimotop), amlodipine (Norvasc), felodipine (Plendil), nisoldipine (Sular), bepridil (Vascor), hydralazine (Apresoline), minoxidil (Loniten), isosorbide dinitrate (Dilatrate-SR, Iso-Bid, Isonate, Isorbid, Isordil, Isotrate, Sorbitrate), isorbide mononitrate (IMDUR), prazosin (Minipress), cilostazol (Pletal), treprostinil (Remodulin), cyclandelate, isoxsuprine (Vasodilan), nylidrin (Arlidin), nitrates (Deponit, Minitran, Nitro-Bid, Nitrodisc, Nitro-Dur, Nitrol, Transderm-Nitro), benazepril (Lotensin), benazepril and hydrochlorothiazide (Lotensin HCT), captopril (Capoten), captopril and hydrochlorothiazide (Capozide), enalapril (Vasotec), enalapril and hydrochlorothiazide (Vaseretic), fosinopril (Monopril), lisinopril (Prinivil, Zestril), lisinopril and hydrochlorothiazide (Prinzide, Zestoretic), moexipril (Univasc), moexipril and hydrochlorothiazide (Uniretic), perindopril (Aceon), quinapril (Accupril), quinapril and hydrochlorothiazide (Accuretic), ramipril (Altace), trandolapril (Mavik), papaverine (Cerespan, Genabid, Pavabid, Pavabid HP, Pavacels, Pavacot, Pavagen, Pavarine, Pavased, Pavatine, Pavatym, Paverolan).

In some embodiments, the present invention provides the delivery of diuretics, including, but not limited to, acetazolamide (Diamox), dichlorphenamide (Daranide), methazolamide (Neptazane), bendroflumethiazide (Naturetin), benzthiazide (Exna), chlorothiazide (Diuril), chlorthalidone (Hygroton), hydrochlorothiazide (Esidrix, HydroDiuril, Microzide), hydroflumethiazide (Diucardin), indapamide (Lozol), methyclothiazide (Enduron), metolazone (Zaroxolyn, Mykrox), polythiazide (Renese), quinethazone (Hydromox), trichlormethiazide (Naqua), bumetanide (Bumex), ethacrynic acid (Edecrin), furosemide (Lasix), torsemide (Demadex), amiloride (Midamor), amiloride and hydrochlorothiazide (Moduretic), spironolactone (Aldactone), spironolactone and hydrochlorothiazide (Aldactazide), triamterene (Dyrenium), triamterene and hydrochlorothiazide (Dyazide, Maxzide).

In some embodiments, the present invention provides the delivery of anti-cancer agents, including, but not limited to, aldesleukin, alemtuzumab, alitretinoin, allopurinol, altretamine, amifostine, anagrelide, anastrozole, arsenic trioxide, asparaginase, bexarotene, bicalutamide, bleomycin, busulfan, calusterone, capecitabine, carboplatin, carmustine, celecoxib, chlorambucil, cisplatin, cladribine, cyclophosphamide, cytarabine, dacarbazine, dactinomycin, darbepoetin alpha, daunorubicin, daunomycin, dexrazoxane, docetaxel, doxorubicin, epoetin alpha, estramustine, etoposide, etoposide phosphate, exemestane, filgrastim, floxuridine, fludarabine, flutamide, fulvestrant, gemcitabine, gemtuzumab ozogamicin, goserelin acetate, hydroxyurea, ibritumomab tiuxetan, idarubicin, ifosfamide, imatinib mesylate, interferon alpha-2a, interferon alpha-2b, irinotecan, leflunomide, letrozole, leucovorin, levamisole, lomustine, meclorethamine (nitrogen mustard), megestrol acetate, melphalan, mercaptopurine, mesna, methotrexate, methoxsalen, mitomycin C, mitotane, mitoxantrone, mycophenolate mofetil, nandrolone phenpropionate, nilutamide, nofetumomab, oprelvekin, oxaliplatin, paclitaxel, pamidronate, pegademase, pegaspargase, pegfilgrastim, pentostatin, pipobroman, plicamycin, porfimer sodium, procarbazine, quinacrine, rasburicase rituximab, sargramostim, streptozocin, tacrolimus, tamoxifen, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In other embodiments, the wound active agent is an siRNA. The RNAi constructs of the present invention are gene(s) that express RNAs that base pair to form a dsRNA RNA region. The RNAs may be a part of the same molecule or different molecules. In preferred embodiments, the RNAi construct comprises a promoter operably linked to a nucleic acid sequence encoding two complementary sequences separated by a loop sequence. The complementary regions correspond to a target RNA sequence separated by a loop sequence. When the RNAi construct is expressed, the complementary regions of the resulting RNA molecule pair with one another to form a double stranded RNA region. The present invention is not limited to loop sequences of any particular length. In some preferred embodiments, the loop sequences range from about 4 to about 20 nucleotides in length. In more preferred embodiments, the loop sequences are from about 6 to about 12 nucleotides in length. In other preferred embodiments, the dsRNA regions are from about 19 to about 23 in length.

In other embodiments, the dsRNA is formed from RNA transcribed from a vector as two separate stands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. In some embodiments, a DNA duplex provided at each end with a promoter sequence can directly generate RNAs of defined length, and which can join in pairs to form a dsRNA. See, e.g., U.S. Pat. No. 5,795,715, incorporated herein by reference. RNA duplex formation may be initiated either inside or outside the cell.

It will be recognized that after processing the resulting siRNA can comprise two blunt ends, one blunt end and one end with an overhang, or two ends with overhangs. In some embodiments, the end or ends with overhangs comprise an overhang of either one or two nucleotides. As a none limiting example, a siRNA of 23 nucleotides in length comprises two 19 mers with a two nucleotide overhang at each end. As another non-limiting example, a siRNA of 21 nucleotides in length comprises two 19 mers with a single nucleotide overhang at each end. As still another non-limiting example, a siRNA of 22 nucleotides in length comprises two 22 mers with no overhangs at either end.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

There is no upper limit on the length of the dsRNA that can be used. For example, the dsRNA can range from about 21 base pairs (bp) of the gene to the full length of the gene or more. In one embodiment, the dsRNA used in the methods of the present invention is about 1000 bp in length. In another embodiment, the dsRNA is about 500 bp in length. In yet another embodiment, the dsRNA is about 22 bp in length.

In some preferred embodiments, the sequences that mediate RNAi are from about 21 to about 23 nucleotides. The isolated iRNAs of the present invention mediate degradation of the target RNA.

The double stranded RNA of the present invention need only be sufficiently similar to natural RNA that it has the ability to mediate RNAi for the target RNA. In one embodiment, the present invention relates to RNA molecules of varying lengths that direct cleavage of specific mRNA to which their sequence corresponds. It is not necessary that there be perfect correspondence of the sequences, but the correspondence must be sufficient to enable the RNA to direct RNAi cleavage of the target mRNA. In a particular embodiment, the RNA molecules of the present invention comprise a 3' hydroxyl group.

III. Matrix Compositions

In some embodiments, the present invention provides compositions comprising a matrix that can be applied to a wound. In some embodiments, the matrix is functionalized. In some embodiments, the matrix comprises one or more polymers, preferably biocompatible, or is formed from one more proteins, or is a combination of polymers and proteins. The matrix is preferably functionalized to allow for covalent interaction and/or binding to the wound bed, or to allow application of wound active agents to the matrix. In some embodiments, a wound active agent, for example an antimicrobial agent such as a solver compound, is incorporated into the matrix. In some embodiments, the matrix is formed or provided on a solid support. The solid support can form an outer permeable, semi-permeable, or impermeable barrier after application of the matrix to a wound or can serve as a removed support for transfer and application of the matrix to the wound followed by removal of the support. In some embodiments, the matrix is a commercially available matrix such as Biobrane™.

In some embodiments, the matrices, such as polymer multilayers, are nanoscale in dimension. Accordingly, in some embodiments, the matrices are from about 1 nm to 1000 nm thick, from about 1 nm to 500 nm thick, from about 1 nm to 100 nm thick, from about 1 nm to about 25 nm thick, from about 1 nm to about 10 nm thick, or less than about 500 nm, 100 nm, 25 nm or 10 nm thick. It is contemplated that the nanoscale dimension of the matrices (i.e., the nanoscale thickness) allows for the loading of a lower total amount of an active agent while still allowing delivery of an effective amount (i.e., an amount of active agent that accelerates wound healing as compared to controls) of the active agent as compared to matrix structures with greater thickness. It is contemplated that the lower total loading levels result in reduced toxicity in the wound environment, especially when antimicrobial compounds are incorporated into the polymer multilayer.

In some embodiments, the compliance of the matrices, such as polymer multilayers, is adjusted to facilitate cell migration in the wound. In some embodiments, the matrices have a compliance, measured in kilopascals (kPa) of from about 3 to about 500 kPa, about 7 to about 250 kPa, about 10 to about 250 kPA or from about 10 to about 200 kPa.

A. Polymer Matrix Materials

In some embodiments, the matrix is a polymer multilayer. In some embodiments, the multilayer structures comprise layers of polyelectrolytes (i.e., forming a polyelectrolyte multilayer), while in other embodiments, the multilayers comprise polymers that do not have a charge (i.e., non-ionic polymers) or a combination of charged and uncharged polymer layers. In some embodiments, it is contemplated that polyelectrolyte films built-up by the alternated adsorption of cationic and anionic polyelectrolyte layers constitute a novel and promising technique to modify wound surfaces in a controlled way [(Decher et al., 1992, Thin Solid Films 210/211: 831; Decher, 1997, Science 277:1232). One of the most important properties of such multilayers is that they exhibit an excess of alternatively positive and negative charges (Caruso et al., 1999, J Am Chem Soc 121:6039; Ladam et al., 2000, Langmuir 16:1249). Not only can this constitute the motor of their buildup (Joanny, 1999, Eur. Phys. J. Biol. 9:117), but it allows, by simple contact, to adsorb a great variety of compounds such as dyes, particles (Cassagneau et al., 1998, J. Am. Chem. Soc. 120:7848; Caruso et al., 1999, Langmuir 15:8276; Lvov et al., 1997, Langmuir 13:6195), clay microplates (Ariga et al., 1999, Appl. Clay Sci. 15:137) and proteins (Keller et al., 1994, J. Am. Chem. Soc. 116:8817; Lvov et al., 1995, J. Am. Chem. Soc. 117:6117; Caruso et al., 1997, Langmuir 13:3427).

Polyelectrolyte layers are formed by alternating applications of anionic polyelectrolytes and cationic polyelectrolytes to surfaces to form a polyelectrolyte multilayer. In some embodiments, one or more wound active agents, such as those described above, are incorporated into the multilayer. Preferably, at least four layers, and, more preferably, at least six layers are used to form the polyelectrolyte multilayer.

Cationic polyelectrolytes useful in the present invention can be any biocompatible water-soluble polycationic polymer, for example, any polymer having protonated heterocycles attached as pendant groups. As used herein, "water soluble" means that the entire polymer must be soluble in aqueous solutions, such as buffered saline or buffered saline with small amounts of added organic solvents as co-solvents, at a temperature between 20 and 37° Centigrade. In some embodiments, the material will not be sufficiently soluble (defined herein as soluble to the extent of at least one gram per liter) in aqueous solutions per se but can be brought into solution by grafting the polycationic polymer with water-soluble polynonionic materials such as polyethylene glycol.

Representative cationic polyelectrolytes include natural and unnatural polyamino acids having net positive charge at neutral pH, positively charged polysaccharides, and positively charged synthetic polymers. Examples of suitable polycationic materials include polyamines having amine groups on either the polymer backbone or the polymer side chains, such as poly-L-lysine (PLL) and other positively charged polyamino acids of natural or synthetic amino acids or mixtures of amino acids, including, but not limited to, poly(D-lysine), poly(ornithine), poly(arginine), and poly(histidine), and nonpeptide polyamines such as poly(aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan.

In general, the polymers must include at least five charges, and the molecular weight of the polycationic material must be sufficient to yield the desired degree of binding to a tissue or other surface, having a molecular weight of at least 1000 g/mole.

Polyanionic materials useful in the present invention can be any biocompatible water-soluble polyanionic polymer, for example, any polymer having carboxylic acid groups attached as pendant groups. Suitable materials include alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose and crosmarmelose, synthetic polymers and copolymers containing pendant carboxyl groups, such as those containing maleic acid or fumaric acid in the backbone. Polyaminoacids of predominantly negative charge are also suitable. Examples of these materials include polyaspartic acid, polyglutamic acid, and copolymers thereof with other natural and unnatural amino acids. Polyphenolic materials such as tannins and lignins can be used if they are sufficiently biocompatible. Preferred materials include alginate, pectin, carboxymethyl cellulose, heparin and hyaluronic acid.

In some embodiments, the cationic polyelectrolyte used is PLL and the anionic polyelectrolyte used is poly(L-glutamic acid) (PGA). Indeed, the use of a variety of polyelectrolytes is contemplated, including, but not limited to, poly(ethylene imine) (PEI), poly(allylamine hydrochloride) (PAH), poly(sodium 4-styrenesulfonate) (PSS), poly(acrylic acid) (PAC), poly(maleic acid-co-propylene) (PMA-P), and poly(vinyl sulfate) (PVS). It is also possible to use naturally occurring polyelectrolytes, including hyaluronic acid and chondroitin sulfate. In still further embodiments, the polymer is a dendrimer, grafted polymer, or star architecture polymer.

In some embodiments, the multilayer structures are formed from uncharged polymers or from a combination of charged and uncharged polymers. Examples of uncharged polymers include, but are not limited to, dextran, dextran sulfate, diethylaminoethyl (DEAE)-dextran, hydroxyethyl cellulose, ethyl(hydroxyethyl) cellulose, acrylamide, polyethylene oxide, polypropylene oxide, polyethylene oxide-polypropylene oxide copolymers, PAAN$_a$, Ficoll, polyvinylpyrrolidine, and polyacrylic acid.

In some embodiments, the multilayer structures are formed from one or more amphoteric polymers, alone in combination with the other polymers described herein. In some embodiments, the amphoteric polymers comprise one or more of acrylic acid (AA), DMAEMA (dimethylaminoethyl methacrylate), APA (2-aminopropyl acrylate), MorphEMA (morpholinoethyl methacrylate), DEAEMA (diethylaminoethyl methacrylate), t-ButylAEMA (t-butylaminoethyl methacrylate), PipEMA (piperidinoethyl methacrylate), AEMA (aminoethyl methacrylate), HEMA (2-hydroxyethyl methacrylate), MA (methyl acrylate), MAA (methacrylic acid) APMA (2-aminopropyl methacrylate), AEA (aminoethyl acrylate). In some embodiments, the amphoteric polymer comprises (a) carboxylic acid, (b) primary amine, and (c) secondary and/or tertiary amine. The amphoteric polymers have an isoelectric point of 4 to 8, preferably 5 to 7 and have a number average molecular weight in the range of 10,000 to 150,000.

Polymer layers may be formed by a variety of methods. In some embodiments, the polymer layers are formed on solid supports as described in detail below. In some embodiments, it is contemplated that the polymer or polymer multilayers is formed by sequential application of polymers using either a pump (including syringes, ink jet printers, and electrojets) or spray, such as an aerosol spray. In other embodiments, particle bombardment is utilized. In other embodiments, the use of a brush including an air brush is contemplated. In other embodiments, a sponge is utilized. In other embodiments a solid support or stamp such as an elastomeric material, for example, PDMS (polydimethylsiloxane), silicone, hydrogel or latex, is used to support the polymer layer and mechanically transfer the polymer layer into or onto the wound bed.

In some embodiments, the matrix comprises one or more proteins. In preferred embodiments, the proteins form a hydrogel. In some preferred embodiments, the matrix comprises one or more extracellular matrix proteins. In some embodiments, the matrix comprises at least one of collagen, laminin, vitronectin, fibronectin, keratin, and combination thereof. As described above, the protein matrix may preferably be formed by a variety of methods. In some embodiments, the protein matrix is formed on solid supports as described in detail below. In some embodiments, it is contemplated that the protein matrix is formed by application of proteins or solutions or gels of proteins using either a pump (including syringes, ink jet printers, and electrojets) or spray, such as an aerosol spray. In other embodiments, the use of a brush including an air brush is contemplated. In other embodiments, a sponge is utilized. In other embodiments a solid support or stamp such as an elastomeric material, for example, PDMS (polydimethylsiloxane), silicone, hydrogel or latex, is used to support the protein matrix and mechanically transfer the protein matrix into or onto the wound bed.

In some embodiments, the matrix is further modified to include cells, including, but not limited to, stem cells, keratinocytes, 3-D skin constructs, corneal epithelial cells, conjunctival cells, corneal limbal stem cell, human embryonic stem cells, pluripotential stem cells, adult induced stem cells, hematopoietic stem cells, hepatocytes, pancreatic cells and the like. In some embodiments, the compositions and methods described herein are used to functionalize harvested and processed (frozen, freeze dried, fixed and stored dry or wet, fresh tissue for direct transplant) animal and human tissue (pig/human aortic valve, harvested human amniotic membrane, human cadaver skin, harvested sclera and cornea, harvested cadaver bone, harvested blood vessels and the like. In some embodiments, the compositions and methods described herein are used to functionalize skin constructs, including, but not limited to, autograft skin (i.e., skin is harvested from a patient, functionalized as described herein, and returned to the patient), organotypically cultured human skin equivalents, and other keratinocyte products such as Dermagraft™.

B. Functionalization Agents

In some embodiments, the matrices described above are functionalized. In preferred embodiments, the matrices are functionalized with one or more covalent modification agents. In some preferred embodiments, the crosslinkers comprise either an azide group or an alkyne group so that suitable click chemistries can be utilized. In some embodiments, the at least one covalent modification agent is a homobifunctional cross-linker. In other embodiments, the at least one covalent modification agent is a heterobifunctional cross-linker. For example, in some embodiments, the homobifunctional cross-linker is an N-hydroxysuccinimidyl ester (e.g., including, but not limited to, disuccinimidyl ester, dithiobis (succinimidylpropionate), 3,3'-dithiobis(sulfosuccinimidyl-propionate), disuccinimidyl suberate, bis(sulfosuccinimidyl) suberate, disuccinimidyl tartarate, disulfosuccinimidyl tartarate, bis[2-(succinimidyloxycarbonyloxy)ethyl]sulfone, bis[2-(sulfosuccinimidooxycarbonyloxy)ethyl]sulfone, ethylene glycolbis(succinimidylsuccinate), ethylene glycolbis (sulfosuccinimidylsuccinate), disuccinimidyl glutarate, and N,N'-disuccinimidylcarbonate). In some embodiments, the homobifunctional cross-linker is at a concentration between 1 nanomolar and 10 millimolar. In some preferred embodiments, the homobifunctional cross-linker is at a concentration between 10 micromolar and 1 millimolar. In other embodiments, the at least one covalent modification agent is a heterobifunctional cross-linker (e.g., including, but not limited to, N-succinimidyl 3-(2-pyridyldithio)propionate, succinimidyl 6-(3-[2-pyridyldithio]-propionamido)hexanoate, sulfosuccinimidyl 6-(3'-[2-pyridyldithio]-propionamido) hexanoate, succinimidyloxycarbonyl-α-methyl-α-(2-pyridyldithio)toluene, sulfosuccinimidyl-6-[α-methyl-α-(2-pyridyldithio)toluamido]hexanoate, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxy-sulfosuccinimide ester, N-succinimidyl(4-iodoacetyl)aminobenzoate, sulfo-succinimidyl(4-iodoacetyl)aminobenzoate, succinimidyl-4-(p-maleimidophenyl)butyrate, sulfosuccinimidyl-4-(p-maleimidophenyl)butyrate, N-(γ-maleimidobutyryloxy) succinimide ester, N-(γ-maleimidobutyryloxy) sulfosuccinimide ester, succinimidyl 6-((iodoacetyl)amino) hexanoate, succinimidyl 6-(6-(((4-iodoacetyl)amino) hexanoyl)amino)hexanoate, succinimidyl 4-(((iodoacetyl) amino)methyl)cyclohexane-1-carboxylate, succinimidyl 6-((((4-iodoacetyl)amino)methyl)cyclohexane-1-carbonyl) amino)-hexanoate, and p-nitrophenyl iodoacetate). In some embodiments, the heterobifunctional cross-linker is modified with functional groups, rendering it soluble in aqueous solvents for delivery as an aqueous solution. Furthermore, in some embodiments, the aqueous solution contains additives (e.g., including, but not limited to, surfactants and block copolymers). In other embodiments, a multiplicity of heterobifunctional cross-linkers can be attached to a molecule, polymer or particle to serve as the cross-linking agent. In other embodiments, the heterobifunctional cross-linker is dissolved in an organic solvent (e.g., including, but not limited to, dimethyl sulfoxide).

In some embodiments, the covalent modifier is a photoactivatable crosslinker. Suitable photoactivatable crosslinkers include, but are not limited to, aryl azide N-((2-pyridyldithio) ethyl)-4-azidosalicylamide, 4-azido-2,3,5,6-tetrafluorobenzoic acid, succinimidyl ester, 4-azido-2,3,5,6-tetrafluorobenzoic acid, STP ester, benzophenone maleimide, succinimidyl ester of 4-benzoylbenzoic acid, N-5-Azido-2-Nitrobenzoyloxysuccinimide, N-Hydroxysulfosuccinimidyl-4-azidobenzoate, N-Hydroxysuccinimidyl-4-azidosalicylic acid, and (4-[p-Azidosalicylamido]butylamine).

The covalent modification agent may be applied to the matrix by any suitable method. In some embodiments, it is contemplated that the covalent modification agent is applied using either a pump (including syringes, ink jet printers, and electrojets) or spray, such as an aerosol spray. In other embodiments, the use of a brush including an air brush is contemplated. In other embodiments, a sponge is utilized.

Following application of the covalent modification agent to the matrix, a functionalized matrix is formed. In some embodiments, the functionalized matrix displays one or more reactive moieties, for example, azide moieties, succinimidyl moieties, alkyne moieties or any of the other reactive groups of the compounds described above.

In some embodiments, the matrix is modified by PEGylation with polyethylene glycol. It is contemplated that PEGylation can be used to control interaction of the matrix with the wound bed and to prevent nonspecific adsorption as desired. PEGylation can also be used to control delivery of the wound active agent from the matrix.

C. Wound Active Agents

In some embodiments, the matrices comprise one or more wound active agents as described in detail above. In some embodiments, the wound active agent or agents are noncovalently incorporated into the matrix. In some preferred embodiments, silver containing antimicrobials are incorporated into the functionalized matrix, for example, a polyelectrolyte multilayer as described above. In some embodiments, the wound active agent or agents are covalently immobilized on the matrix, for example, via a covalent modification agent.

In some embodiments, the one or more wound active agents are applied to form a gradient with respect to the wound modifying agent. In general, the gradients present a higher contraction of wound active agent at one or more first desired locations in the wound following application of the wound modifying agent to the wound and a lower concentration of wound active agent at one or second location in the wound following application of the matrix to the wound. For example, the concentrations of the wound active agents are layered in a wound bed in a gradient such that higher concentrations of a particular composition is greater proximal to the wound bed than distal to the wound bed in a vertical fashion. The converse, where concentrations of compositions is greater distal to the wound bed than proximal, is also contemplated. Concentration of compositions in a wound bed wherein a horizontal gradient is deposited is also contemplated. Topographical gradients are also contemplated, wherein compositions are deposited such that the concentrations of compositions in a wound bed or on a biocompatible particle follow the topography of the substrate, for example, a higher concentration of compositions is deposited in the valleys of undulations of an exemplary substrate compared to the peaks of the undulations.

In some embodiments, the gradient comprises a higher concentration of the wound active agent in the center of the matrix which transitions to a lower concentration of the wound active agent away from the center of the matrix. Accordingly, when the matrix is applied to a wound, the gradient results in a higher concentration of wound active agent in the center of the wound and a lower concentration of wound active agent as one moves to the periphery of the wound. In some embodiments, the gradient comprises a lower concentration of the wound active agent in the center of the matrix which transitions to a higher concentration of the wound active agent away from the center of the matrix. Accordingly, the gradient results in a lower concentration of wound active agent in the center of the wound and a higher concentration of wound active agent as one moves to the periphery of the wound. If two or more wound active agents are utilized, they can be presented as similar gradients or the gradients can be varied so that the concentrations of the two or more wound active agents vary across the wound. The gradients of high or low concentration can be any shape, such as circular, square, rectangular, oval, oblong, etc. so that the matrix and gradient can conform to a variety of wound shapes. For example, for long, incision type wound, the gradient may be centered on a longitudinal axis that extends along the length of the wound and can be centered on the wound. As another example, the gradient can be circular or oval-shaped for application to open type wounds, burns, sores and ulcers that are roughly circular or oval. In other embodiments, the gradients comprise a series of features arranged in a pattern. For example, the gradients can form a series of stripes or high and low concentrations of one or more wound active agents along a longitudinal axis of the matrix. Alternatively, the gradients can form a checkerboard pattern, array, concentric circles, overlapping circles or oval, etc.

D. Support Materials

In some embodiments, the matrices are formed on a support material. Suitable support materials include, but are not limited to, silicon, especially medical grade silicon, nylon, nylon mesh, Gortex, silk, polyurethane, Teflon, polyethylene oxide membranes, PVDF membranes, polyvinyl alcohol membranes, cotton gauze and biological materials such as amniotic membranes, cadaver skin, organotypically cultured skin equivalents, Dermagraft™, and the like. In some embodiments, the matrix and the support material are applied to the wound, while in other embodiments, the support material is used to apply the matrix to the wound and then removed in a stamping process.

E. Use of Matrices

In some embodiments, a matrix as described above is applied to a wound under conditions such that wound healing, as measured by wound contraction, is accelerated. In some embodiments, the matrix is functionalized just prior to application to a wound, while in other embodiments, the matrix is provided in a sterile package and is functionalized so that it is ready for application following removal from the sterile packaging. In some embodiments, the wound is pretreated or primed with a covalent modification agent that is reactive with the functionalization agent displayed by the functionalized matrix. For example, the wound may be modified as described in detail above with a covalent modification agent displaying a reactive azide group, while the matrix may be modified with a covalent modification agent displaying an alkyne group. In general, the wound may be modified with covalent modification agent A which displays reactive group X and the matrix displays covalent modification agent B which displays reactive group Y, wherein X and Y react with each other to form a covalent bond.

In some embodiments, the matrices are provided as kits, preferably with the matrix in a sterile package. In some embodiments, the matrix in the kit is pre-functionalized, while in other embodiments, the matrix is not functionalized and the kit comprises at least one functionalization agent along with instructions on how to functionalize the matrix. In some embodiments, the kits comprise a functionalization agent for functionalizing the wound bed prior to application of the matrix. In some embodiments the matrix providing in the kit comprises at least one wound active agent. In other embodiments, the kits comprise a wound active agent and instructions from applying the wound active agent to the matrix prior to application to a wound.

IV. Methods of Treating Wounds

A wound modifying agent with one or more wound active agents or matrix, as described above can be applied to all types of wounds. Furthermore, the compositions of the present invention can be applied to skin, mucous membranes, body cavities, and to internal surfaces of bones, tissues, etc. that have been damaged. A composition of the present invention can be used on wounds such as cuts, abrasions, ulcers, surgical incision sites, burns, and to treat other types of tissue damage. In some embodiments of the present invention, the compositions and methods described above enhance wound healing. The present invention contemplates that wound healing may be enhanced in a variety of ways. In some embodiments, the compositions and methods minimize contracture of the wound as to best favor function and cosmesis. In some embodiments, compositions and methods promote wound contracture to best favor function and cosmesis. In some embodiments, the compositions and methods promote vascularization. In some embodiments, the compositions and methods inhibit vascularization. In some embodiments, the compositions and methods promote fibrosis. In some embodiments, the compositions and methods inhibit fibrosis. In some embodiments, the compositions and methods promote epithelial coverage. In some embodiments, the compositions and methods inhibit epithelial coverage. In some embodiments, the compositions and methods of the present invention modulates one or properties of cells in the wound environment or in the immediate vicinity of the wound. The properties that are modulated, e.g., are increased or decreased, include, but are not limited to adhesion, migration, proliferation, differentiation, extracellular matrix secretion, phagocytosis, MMP activity, contraction, and combinations thereof.

The compositions of the present invention can be covered with a secondary dressing, or bandage, if desired to protect the layer or to provide additional moisture absorption, for example.

If desirable, the wound modifying agent with one or more wound active agents can be reapplied at a later time. It may be desirable to wound modifying agents having different formulations of wound active agents at different stages of wound healing.

In some embodiments, the immobilization of cytoactive factors and matrices immobilized on a wound bed using, for example, polyelectrolytes are evaluated in vitro and in vivo. In some embodiments, in vitro analysis comprising studying the ability of cytoactive factors to proliferate cell growth is evaluated in corneal epithelial cells and human vascular endothelial cells. In some embodiments, in vitro analysis comprises the construction of synthetic surfaces that mimic a wound bed, wherein said surfaces are created to comprise surface chemistries such as primary amine groups, carboxylic acids and thiol groups that are representative of the diversity of chemical functionality present in a wound bed. For example, ECM constituents and cytoactive factors are applied to the synthetic surfaces, and immobilization is confirmed by, for example, fluorescently labeled antibodies to the ECMs and cytoactive factors thereby immobilized. Further in vitro analysis includes, but is not limited to, proliferation dose response of the cytoactive factors and EMCs on the synthetic surfaces. In some embodiments, the in vitro assays are used to evaluate cytoactive factors that inhibit specific cell growth in a wound bed, thereby allowing for preferential recruitment and growth of those cell types optimal for wound healing and rapid return of tissue function and non-recruitment of antagonistic cell species.

In one embodiment, assays to evaluate immobilization strategies are performed ex vivo. In some embodiments, cutaneous wounds are harvested from mice. For example, a 6 mm surgical skin punch is used to create a cutaneous defect postmortem, followed by removal of the entire wound bed (e.g., with underlying stromal muscular elements). Similar to the model in vitro system as previously described, the ex vivo model system includes linker chemistries and the like, and the immobilization strategies are evaluated, for example, using fluoresceinated proteins. In some embodiments, the ex vivo model system comprises the immobilization of biotinylated BSA. In some embodiments, the surface of the wound bed is activated with a NHS ester by exposure to, for example, 1 mM $BS_3$. Biotinylated BSA (at, for example, 2 mg/ml) is subsequently added to the activated wound bed and allowed to attach for 2 hours. The biotinylated BSA immobilization is determined by FITC-labeled anti-biotin antibody. As such, once immobilization is verified (via fluorescence detection), evaluation of optimal chemical functionalities is determined for wound bed immobilization. For example, chemical functionalities are determined by replacing $BS_3$ in the ex vivo model system with heterobifunctional cross-linkers as described herein that react with, for example, carboxylic acids, amines, and thiol groups found in the wound bed. Further, upon determination of optimal cross-linkers, the immobilization of cytoactive agents and extracellular matrix compounds as described herein are evaluated (e.g., using fluorescently labeled antibodies to immobilized compounds). It is contemplated that key parameters to a successful ex vivo evaluation include, but are not limited to, concentration of all immobilization compositions, buffer systems, and incubation times. Ex vivo evaluations constitute additional validation of in vivo wound bed healing systems.

In one embodiment, in vivo experiments further validate the wound bed healing methods as described herein. In some embodiments, the diabetic transgenic mouse db/db are used, as a phenotype of the diabetic mice is impaired wound healing. Polyelectrolytes, cytoactive agents, and extracellular matrices as described herein are applied to the db/db mice for optimization of wound healing. The present invention is not limited to a particular mechanism. Indeed, an understanding of the mechanism is not necessary to practice the present invention. Nonetheless, it is contemplated that optimized wound healing in diabetic mice provides a model system that correlates to wound healing for normal, cutaneous wounds. In one example, skin wounds are created in tandem on diabetic mice using a surgical skin punch. After wounding, test compounds are immobilized in one of the wounds, leaving the other as a control (e.g., BSA only). The test compounds are evaluated, for example as described in Example 3, thereby providing further information for useful in vivo compositions for wound bed healing. Information on the impact of the test compounds on wound healing is also obtained by, for example, evaluation of the wound bed for epithelial coverage, extent of formation of granulation tissue, collagen content, inflammation, fibroblast population and vascularization. Test compounds include, but are not limited to, the polyelectrolytes as described herein, extracellular matrix components (e.g., collagen, laminin, MATRIGEL, fibronectin, etc.) and cytoactive agents (e.g., EGF, VEGF, PDGF). To further characterize the wound bed, confocal microscopy is used to visualize cellular components in a three-dimensional space, thereby allowing for the visualization of the wound bed treatments in a native state.

In some embodiments, the present invention provides for the development of personalized therapeutic protocols for would healing. For example, the compositions as described herein for wound healing are adapted for each individual wound, taking into account, for example, environmental factors, incubation times, application dynamics, wound bed structure, associated disease state (e.g., diabetes, etc.) and the like that make each wound bed unique. As such, the present invention provides for the alteration of surface chemistry/structure for each unique wound bed, using the compositions and methods as described herein.

EXPERIMENTAL

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. The examples are not intended to restrict the scope of the invention.

Example 1

Covalent Immobilization of a Protein to a Surface

To demonstrate that proteins can be covalently immobilized on model surfaces, bovine serum albumin (BSA) was used as the protein in the model system. Bovine serum albumin was biotinylated (BSA used as control) and covalently attached to gamma-amino propyl silanes (GAPS)-treated glass surfaces using the homobifunctional bifunctional cross-linker $BS_3$ (1 mM for 15 min.). $BS_3$ contains an amine-reactive N-hydroxysulfosuccinimide (NHS) ester at each end of an 8-carbon spacer arm. The NHS esters react with primary amines at pH 7-9 to form stable amide bonds, along with release of the N-hydroxysulfosuccinimide leaving group. For detection purposes, the biotinylated BSA was labeled with FITC-labeled anti-biotin antibodies and the BSA control was probed using FITC-antigoat antibodies.

Figure 3:
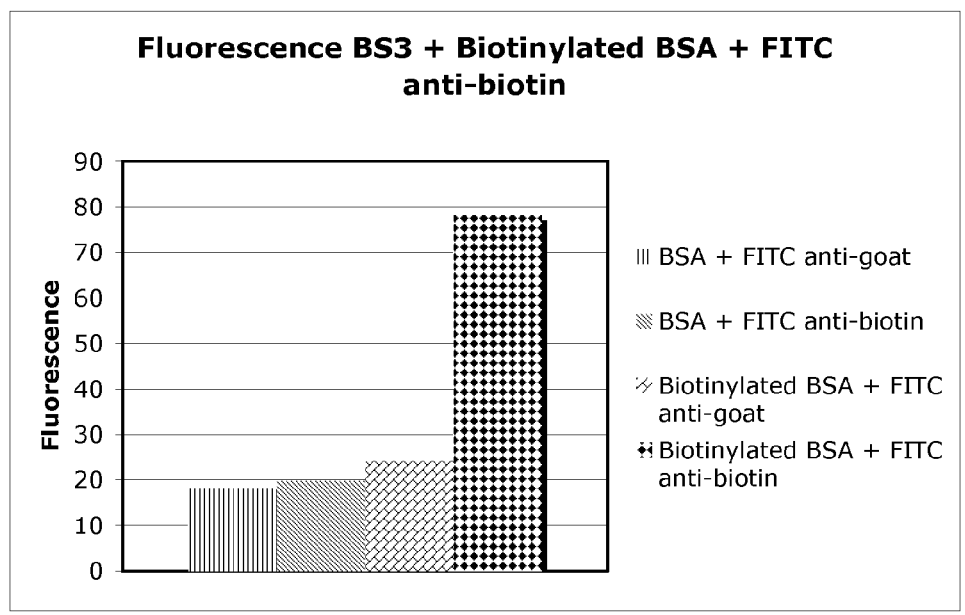
FIG. 3 exemplifies the covalent immobilization of proteins to model amine-terminated treated glass surfaces.

The large fluorescent signal seen in FIG. 3 from the surfaces treated with biotinylated BSA and FITC-antibiotin antibody (diamonds) relative to controls (vertical lines, diagonal lines, bricks) confirms covalent attachment of the biotinylated BSA to the surface.

Example 2

Layer by Layer Deposition of Polyelectrolytes in Ex Vivo Wound Beds

Figure 4:
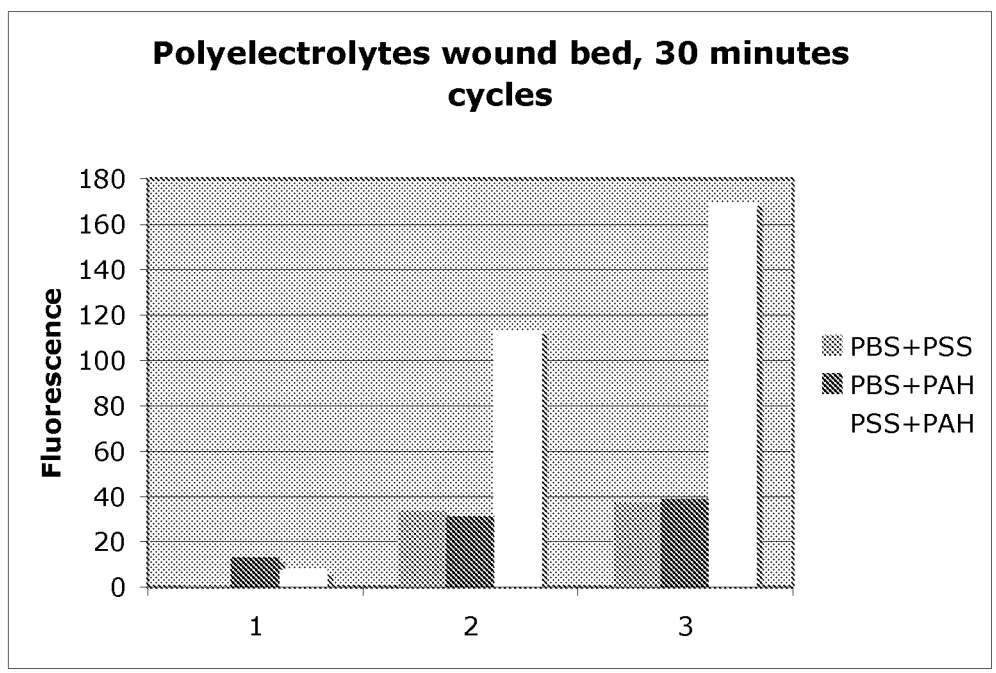
FIG. 4 shows ex vivo results for multilayer deposition of polyelectrolytes polystyrene sulfonate (PSS) and FITC-labelled poly(allylamine hydrochloride) (FITC-PAH).
Figure 5:
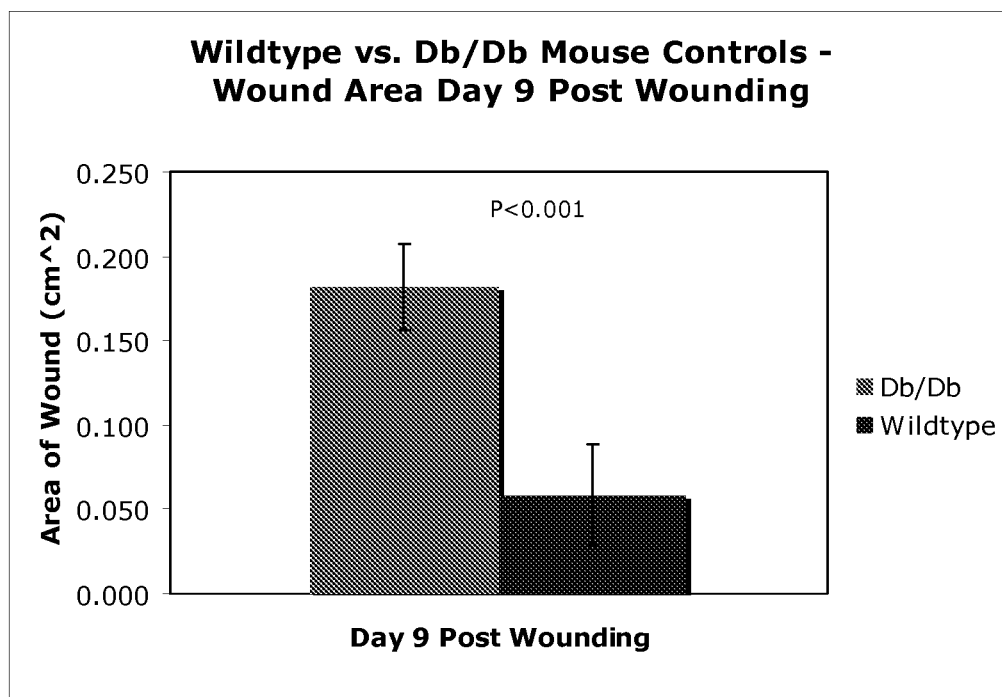
FIG. 5 demonstrates the difference in healing of full thickness cutaneous wounds in diabetic (db/db) mice compared to control (wild type) mice.

Experiments depositing polyelectrolytes in wound bed explants from mice were performed. Cutaneous wounds from euthanized mice were harvested. The excised wounds were sequentially treated with aqueous solutions (0.5M NaCl, PBS at pH 7.0) containing polystyrene sulfonate (PSS, 1 mg/ml) and FITC-labeled poly allylamine hydrochloride (FITC-PAH, 1 mg/ml). Between adsorption steps, the wounds were treated rinsed with PBS. After each treatment with FITC-PAH, the intensity of fluorescence was recorded. As seen in FIG. 4, the growth in fluorescence after each treatment cycle with PSS and FITC-PAH demonstrates growth of a multilayered polyelectrolyte film on the wound bed, relative to control treatments.

Example 3

Use of Mesoscopic Cross-Linkers in Ex Vivo Wound Beds

Skin wounds are created in tandem on diabetic mice using a surgical skin punch. After wounding, one of the wounds is treated by contact with activated 10-micrometer diameter polystyrene beads with surfaces terminated in carboxylic acid groups. The activation of the carboxylic acid groups is achieved by incubation in EDC/NHS solution (200 mM/50 mM) in phosphate buffered saline (PBS) (10 mM phosphate, 120 mM NaCl, 2.7 mM KCl; pH 7.6) for 1 h at room temperature. Following activation, the beads were pipetted into the wound beads and allowed to incubate within the wound beds for 1 hr. After incubation, the wound beds are washed exhaustively with PBS, and then incubated with collagen (10 micromolar in PBS). The remaining wound is used as a control and treated as described above, but without activation of the beads with NHS/EDC. The size of the wound is measured after 2, 4, 6, 8 and 10 days. It is observed that the treated wound decreases in size faster than the control wound.

Example 4

Delivery of the Wound Modifying Agents Using Aerosol Sprays

Experiments depositing polyelectrolytes in wound bed explants from mice are performed using aerosol sprays. Cutaneous wounds from euthanized mice are harvested. The excised wounds are sequentially treated by the spraying (using aerosol spray cans) of aqueous solutions (0.5M NaCl, PBS at pH 7.0) containing polystyrene sulfonate (PSS, 1 mg/ml) or FITC-labeled poly allylamine hydrochloride (FITC-PAH, 1 mg/ml). Between spraying steps, the wounds are treated rinsed with PBS. After each treatment with FITC-PAH, the intensity of fluorescence is recorded. A measurement of the growth in fluorescence after each treatment cycle with PSS and FITC-PAH demonstrates growth of a multilayered polyelectrolyte film on the wound bed, relative to control treatments.

Example 5

Delivery of the Wound Modifying Agents Using Pumps

Experiments depositing polyelectrolytes in wound bed explants from mice are performed by sequentially delivering the wound healing agent to the wound beds using pumps. Cutaneous wounds from euthanized mice are harvested. A peristaltic pump (Fischer Scientific) is used to pump the liquid. The excised wounds are sequentially treated by pumping of aqueous solutions (0.5M NaCl, PBS at pH 7.0) containing polystyrene sulfonate (PSS, 1 mg/ml) or FITC-labeled poly allylamine hydrochloride (FITC-PAH, 1 mg/ml). Between pumping steps involving the polyelectrolytes, the wounds are treated rinsed with PBS using pumps. After each treatment with FITC-PAH, the intensity of fluorescence is recorded. A measurement of the growth in fluorescence after each treatment cycle with PSS and FITC-PAH demonstrates growth of a multilayered polyelectrolyte film on the wound bed, relative to control treatments.

Example 6

Delivery of the Wound Modifying Agents Using Stamps

Experiments depositing polyelectrolytes in wound bed explants from mice are performed by stamping of polyelectrolytes into the wound bed from elastomeric stamps. Elastomeric stamps are prepared from PDMS using parts A and B of a kit purchased from Dow-Corning. After curing the stamps in an oven at 100° C. for 12 hrs, the surface of the PDMS stamp is incubated with aqueous solutions (0.5M NaCl, PBS at pH 7.0) containing polystyrene sulfonate (PSS, 1 mg/ml) or FITC-labeled poly allylamine hydrochloride (FITC-PAH, 1 mg/ml). Between incubation steps involving the polyelectrolytes, the PDMS stamp is rinsed with PBS. After 10 layers each of PSS and PAH are deposited onto the stamp, the stamp is mechanically contacted with the cutaneous wounds harvested from euthanized mice. After removal of the stamp from the wound bed, the intensity of fluorescence of the wound bed is recorded. A measurement of the fluorescence relative to control treatments (PBS free of polyelectrolytes is incubated with the stamps) verifies the deposition of the wound modifying agent into the wound bed.

Example 7

Delivery of the Wound Modifying Agents to Surfaces Using Inkjet Technology

To demonstrate that inkjet technology can be used to deliver wound modifying agents to surfaces, aqueous solutions (in PBS) of FITC-labelled collagen are inkjet printer onto gamma-amino propyl silanes (GAPS)-treated glass surfaces that are activated using the homobifunctional bifunctional cross-linker $BS_3$ (1 mM for 15 min.). $BS_3$ contains an amine-reactive N-hydroxysulfosuccinimide (NHS) ester at each end of an 8-carbon spacer arm. The NHS esters react with primary amines at pH 7-9 to form stable amide bonds, along with release of the N-hydroxysulfosuccinimide leaving group. The surfaces are exhaustively washed with PBS. The fluorescence intensity of the surface is measurements to indicate attachment of the FITC-labelled collagen to the surface relative to a control experiment in which the activated surface is pre-exposed to BSA (1 mg/ml in PBS for 2 hrs), prior to inject printing of the FITC-labelled collagen.

Example 8

Delivery of the Wound Modifying Agents Using Air Brushes

Experiments depositing polyelectrolytes in wound bed explants from mice are performed using airbrushes. Cutaneous wounds from euthanized mice are harvested. The excised wounds are sequentially treated by the airbrushing of aqueous solutions (0.5M NaCl, PBS at pH 7.0) containing polystyrene sulfonate (PSS, 1 mg/ml) or FITC-labeled poly allylamine hydrochloride (FITC-PAH, 1 mg/ml). The airbrushes are prepared by pouring the aqueous polyelectrolyte solutions into the air brushes. Between brushing steps, the wounds are rinsed with PBS. After each treatment with FITC-PAH, the intensity of fluorescence is recorded. A measurement of the growth in fluorescence after each treatment cycle with PSS and FITC-PAH demonstrates growth of a multilayered polyelectrolyte film on the wound bed, relative to control treatments in which PBS solutions free of polyelectrolytes are air brushed onto the surfaces.

Example 9

Method to Modify the Topography of the Wound Bed

Skin wounds are created in tandem on diabetic mice using a surgical skin punch. After wounding, one of the wounds is treated by contact with a 1:1 mixture of activated 100-nanometer and 1 micrometer diameter polystyrene beads with surfaces terminated in carboxylic acid groups. The activation of the carboxylic acid groups is achieved by incubation in EDC/NHS solution (200 mM/50 mM) in phosphate buffered saline (PBS) (10 mM phosphate, 120 mM NaCl, 2.7 mM KCl; pH 7.6) for 1 hour at room temperature. Following activation, the mixture of beads are pipetted into the wound beads and allowed to incubate within the wound beds for 1 hr. After incubation, the wound beds are washed exhaustively with PBS, and then incubated in albumin (10 micromolar in PBS). The remaining wound is used as a control and treated as described above, but without activation of the beads with NHS/EDC. The size of the wound is measured after 2, 4, 6, 8 and 10 days. It is observed that the treated wound decreases in size faster than the control wound.

Example 10

Method to Covalently Modify the Wound Bed Using a Combination of Polyelectrolytes and Covalent Cross-Linking Agents Skin wounds are created in tandem on diabetic mice using a surgical skin punch. After wounding, one of the wounds is treated by contact with activated 1-micrometer diameter polystyrene beads with surfaces terminated in carboxylic acid groups. The activation of the carboxylic acid groups is achieved by incubation in EDC/NHS solution (200 mM/50 mM) in phosphate buffered saline (PBS) (10 mM phosphate, 120 mM NaCl, 2.7 mM KCl; pH 7.6) for 1 hour at room temperature. Following activation, the beads are pipetted into the wound beds and allowed to incubate within the wound beds for 1 hr. After incubation, the wound beds are washed exhaustively with PBS, and then incubated with PAH, and then washed again in PBS. After PAH, the wound bed is sequentially treated with PSS and FITC-labelled PAH (as described above). Between each adsorption step, the wound bed is rinsed with PBS. Fluorescence measurements of the wound bed after each FITC-PAH adsorption step confirm immobilization of the PSS and PAH to the wound bed.

Example 11

Method to Modify the Mechanical Compliance of the Wound Bed

The mechanical compliance of the wound bed is modified by depositing polyelectrolytes into the wound bed and cross-linking the polyelectrolyte films. Experiments depositing polyelectrolytes in wound bed explants from mice are performed. Cutaneous wounds from euthanized mice are harvested. The excised wounds are sequentially treated with aqueous solutions (0.5M NaCl, PBS at pH 7.0) containing polystyrene sulfonate (PSS, 1 mg/ml) and FITC-labeled poly allylamine hydrochloride (FITC-PAH, 1 mg/ml). Between adsorption steps, the wounds are treated and rinsed with PBS. After treatment with the polyelectrolytes, BS3 (1 mM in PBS) is added to the wound bed and incubated for 1 hr. Upon poking with the end of a spatula, the rigidity of the wound bed is noticeably greater than a wound bed treated with polyelectrolytes without the final cross-linking step. The increase in ridigity (decreased compliance) is confirmed by Atomic Force Microscopy.

Example 12

Method to Alter Intrinsic Compliance of Wound Bed

The mechanical compliance of the wound bed is altered by controlled application of enzyme(s) capable of degrading constituents of the extracellular matrix. Cutaneous wounds from euthanized mice are harvested. 10 μM concentration of collagenase is applied to the wound and allowed to incubate at room temperature for times ranging from 0 min-1 hour. The wound beds are then rinsed copiously with PBS. Wet Field force microscopy of the wound beds confirms that application of degradative enzymes increases the compliance (decreases rigidity) of the wound beds in a time dependent fashion.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

What is claimed is:

1. A method of treatment comprising:
   a) providing a subject having a wound comprising a wound bed presenting amine and sulfhydryl groups, at least one bifunctional covalent modification agent that covalently reacts with a chemical entity selected from the group consisting of amine and sulfhydryl groups, and at least one wound active agent;
   b) contacting said wound with said at least one bifunctional covalent modification agent that covalently reacts with a chemical entity selected from the group consisting of amine and sulfhydryl groups in said wound bed to provide a covalently modified wound bed, and
   c) contacting said covalently modified wound bed with said at least one wound active agent under conditions such that said at least one wound active agent is incorporated into said modified wound bed by covalently binding to said bifunctional covalent modification agent and healing of said wound is enhanced, wherein said wound active agent is selected from the group consisting of trophic factors, enzymes, enzyme inhibitors, defensins, anti-infective agents, analgesics, anticoagulants, anti-inflammatory agents, vasoconstrictors, vasodilators, diuretics, and anti-cancer agents.

2. The method of claim 1, wherein said wound active agent is applied to said covalently modified wound bed to form a gradient.

3. The method of claim 1, wherein said bifunctional covalent modification agent is applied to said wound bed by a method selected from the group consisting of stamping, spraying, pumping, painting, smearing and printing.

4. The method of claim 1, wherein said bifunctional covalent modification agent comprises an alkyne group.

* * * * *

SEQUENCE LISTING

<160> NUMBER OF SEQ ID NOS: 95

<210> SEQ ID NO 1
<211> LENGTH: 64
<212> TYPE: PRT
<213> ORGANISM: Bos taurus

<400> SEQUENCE: 1

Met Arg Leu His His Leu Leu Leu Ala Leu Leu Phe Leu Val Leu Ser
1               5                   10                  15

Ala Gly Ser Gly Phe Thr Gln Gly Val Arg Asn Ser Gln Ser Cys Arg
            20                  25                  30

Arg Asn Lys Gly Ile Cys Val Pro Ile Arg Cys Pro Gly Ser Met Arg
        35                  40                  45

Gln Ile Gly Thr Cys Leu Gly Ala Gln Val Lys Cys Cys Arg Arg Lys
    50                  55                  60

<210> SEQ ID NO 2
<211> LENGTH: 24
<212> TYPE: PRT
<213> ORGANISM: Xenopus laevis

<400> SEQUENCE: 2

Gly Val Leu Ser Asn Val Ile Gly Tyr Leu Lys Lys Leu Gly Thr Gly
1               5                   10                  15

Ala Leu Asn Ala Val Leu Lys Gln
            20

<210> SEQ ID NO 3
<211> LENGTH: 81
<212> TYPE: PRT
<213> ORGANISM: Xenopus laevis

<400> SEQUENCE: 3

Met Tyr Lys Gly Ile Phe Leu Cys Val Leu Leu Ala Val Ile Cys Ala
1               5                   10                  15

Asn Ser Leu Ala Thr Pro Ser Ser Asp Ala Asp Glu Asp Asn Asp Glu
            20                  25                  30

Val Glu Arg Tyr Val Arg Gly Trp Ala Ser Lys Ile Gly Gln Thr Leu
        35                  40                  45

Gly Lys Ile Ala Lys Val Gly Leu Lys Glu Leu Ile Gln Pro Lys Arg
    50                  55                  60

Glu Ala Met Leu Arg Ser Ala Glu Ala Gln Gly Lys Arg Pro Trp Ile
65                  70                  75                  80

Leu

<210> SEQ ID NO 4
<211> LENGTH: 303
<212> TYPE: PRT
<213> ORGANISM: Xenopus laevis

<400> SEQUENCE: 4

Met Phe Lys Gly Leu Phe Ile Cys Ser Leu Ile Ala Val Ile Cys Ala
1               5                   10                  15

Asn Ala Leu Pro Gln Pro Glu Ala Ser Ala Asp Glu Asp Met Asp Glu
            20                  25                  30

Arg Glu Val Arg Gly Ile Gly Lys Phe Leu His Ser Ala Gly Lys Phe
        35                  40                  45

-continued

Gly Lys Ala Phe Val Gly Glu Ile Met Lys Ser Lys Arg Asp Ala Glu
        50                  55                  60

Ala Val Gly Pro Glu Ala Phe Ala Asp Glu Asp Leu Asp Glu Arg Glu
65                  70                  75                  80

Val Arg Gly Ile Gly Lys Phe Leu His Ser Ala Lys Lys Phe Gly Lys
                85                  90                  95

Ala Phe Val Gly Glu Ile Met Asn Ser Lys Arg Asp Ala Glu Ala Val
            100                 105                 110

Gly Pro Glu Ala Phe Ala Asp Glu Asp Leu Asp Glu Arg Glu Val Arg
        115                 120                 125

Gly Ile Gly Lys Phe Leu His Ser Ala Lys Lys Phe Gly Lys Ala Phe
    130                 135                 140

Val Gly Glu Ile Met Asn Ser Lys Arg Asp Ala Glu Ala Val Gly Pro
145                 150                 155                 160

Glu Ala Phe Ala Asp Glu Asp Leu Asp Glu Arg Glu Val Arg Gly Ile
                165                 170                 175

Gly Lys Phe Leu His Ser Ala Lys Lys Phe Gly Lys Ala Phe Val Gly
            180                 185                 190

Glu Ile Met Asn Ser Lys Arg Asp Ala Glu Ala Val Gly Pro Glu Ala
        195                 200                 205

Phe Ala Asp Glu Asp Phe Asp Glu Arg Glu Val Arg Gly Ile Gly Lys
    210                 215                 220

Phe Leu His Ser Ala Lys Lys Phe Gly Lys Ala Phe Val Gly Glu Ile
225                 230                 235                 240

Met Asn Ser Lys Arg Asp Ala Glu Ala Val Gly Pro Glu Ala Phe Ala
                245                 250                 255

Asp Glu Asp Leu Asp Glu Arg Glu Val Arg Gly Ile Gly Lys Phe Leu
            260                 265                 270

His Ser Ala Lys Lys Phe Gly Lys Ala Phe Val Gly Glu Ile Met Asn
        275                 280                 285

Ser Lys Arg Asp Ala Glu Ala Val Asp Asp Arg Arg Trp Val Glu
    290                 295                 300

<210> SEQ ID NO 5
<211> LENGTH: 17
<212> TYPE: PRT
<213> ORGANISM: Tachypleus gigas

<400> SEQUENCE: 5

Lys Trp Cys Phe Arg Val Cys Tyr Arg Gly Ile Cys Tyr Arg Arg Cys
1               5                   10                  15

Arg

<210> SEQ ID NO 6
<211> LENGTH: 17
<212> TYPE: PRT
<213> ORGANISM: Tachypleus gigas

<400> SEQUENCE: 6

Arg Trp Cys Phe Arg Val Cys Tyr Arg Gly Ile Cys Tyr Arg Lys Cys
1               5                   10                  15

Arg

<210> SEQ ID NO 7
<211> LENGTH: 129
<212> TYPE: PRT
<213> ORGANISM: Bufo bufo gagarizans -continued

<400> SEQUENCE: 7

Met Ser Gly Arg Gly Lys Gln Gly Gly Lys Val Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ala Gln Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Val Arg Asn Asp Glu Glu Leu Asn Lys
                85                  90                  95

Leu Leu Gly Gly Val Thr Ile Ala Gln Gly Gly Val Leu Pro Asn Ile
            100                 105                 110

Gln Ala Val Leu Leu Pro Lys Thr Glu Ser Ser Lys Pro Ala Lys Ser
        115                 120                 125

Lys

<210> SEQ ID NO 8
<211> LENGTH: 21
<212> TYPE: PRT
<213> ORGANISM: Bufo bufo gagarizans

<400> SEQUENCE: 8

Thr Arg Ser Ser Arg Ala Gly Leu Gln Phe Pro Val Gly Arg Val His
1               5                   10                  15

Arg Leu Leu Arg Lys
            20

<210> SEQ ID NO 9
<211> LENGTH: 63
<212> TYPE: PRT
<213> ORGANISM: Bombyx mori

<400> SEQUENCE: 9

Met Asn Phe Val Arg Ile Leu Ser Phe Val Phe Ala Leu Val Leu Ala
1               5                   10                  15

Leu Gly Ala Val Ser Ala Ala Pro Glu Pro Arg Trp Lys Leu Phe Lys
            20                  25                  30

Lys Ile Glu Lys Val Gly Arg Asn Val Arg Asp Gly Leu Ile Lys Ala
        35                  40                  45

Gly Pro Ala Ile Ala Val Ile Gly Gln Ala Lys Ser Leu Gly Lys
    50                  55                  60

<210> SEQ ID NO 10
<211> LENGTH: 63
<212> TYPE: PRT
<213> ORGANISM: Bombyx mori

<400> SEQUENCE: 10

Met Asn Phe Ala Lys Ile Leu Ser Phe Val Phe Ala Leu Val Leu Ala
1               5                   10                  15

Leu Ser Met Thr Ser Ala Ala Pro Glu Pro Arg Trp Lys Ile Phe Lys
            20                  25                  30

Lys Ile Glu Lys Met Gly Arg Asn Ile Arg Asp Gly Ile Val Lys Ala
        35                  40                  45

Gly Pro Ala Ile Glu Val Leu Gly Ser Ala Lys Ala Ile Gly Lys
    50                  55                  60

<210> SEQ ID NO 11
<211> LENGTH: 63
<212> TYPE: PRT
<213> ORGANISM: Drosophila melanogaster

<400> SEQUENCE: 11

Met Asn Phe Tyr Lys Ile Phe Val Phe Val Ala Leu Ile Leu Ala Ile
1               5                   10                  15

Ser Ile Gly Gln Ser Glu Ala Gly Trp Leu Lys Lys Leu Gly Lys Arg
            20                  25                  30

Ile Glu Arg Ile Gly Gln His Thr Arg Asp Ala Thr Ile Gln Gly Leu
        35                  40                  45

Gly Ile Ala Gln Gln Ala Ala Asn Val Ala Ala Thr Ala Arg Gly
    50                  55                  60

<210> SEQ ID NO 12
<211> LENGTH: 31
<212> TYPE: PRT
<213> ORGANISM: Sus scrofa

<400> SEQUENCE: 12

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 13
<211> LENGTH: 13
<212> TYPE: PRT
<213> ORGANISM: Bos taurus

<400> SEQUENCE: 13

Ile Leu Pro Trp Lys Trp Pro Trp Trp Pro Trp Arg Arg
1               5                   10

<210> SEQ ID NO 14
<211> LENGTH: 34
<212> TYPE: PRT
<213> ORGANISM: Lactococcus lactis

<400> SEQUENCE: 14

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 15
<211> LENGTH: 20
<212> TYPE: PRT
<213> ORGANISM: Rana catesbeiana

<400> SEQUENCE: 15

Phe Leu Gly Gly Leu Ile Lys Ile Val Pro Ala Met Ile Cys Ala Val
1               5                   10                  15

Thr Lys Lys Cys
            20

<210> SEQ ID NO 16
<211> LENGTH: 25

```
<212> TYPE: PRT
<213> ORGANISM: Bos taurus

<400> SEQUENCE: 16

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 17
<211> LENGTH: 19
<212> TYPE: PRT
<213> ORGANISM: Sus scrofa
<220> FEATURE:
<221> NAME/KEY: misc_feature
<222> LOCATION: (19)..(19)
<223> OTHER INFORMATION: Xaa can be any naturally occurring amino acid

<400> SEQUENCE: 17

Arg Gly Gly Arg Leu Cys Tyr Cys Arg Arg Phe Cys Val Cys Val
1               5                   10                  15

Gly Arg Xaa

<210> SEQ ID NO 18
<211> LENGTH: 16
<212> TYPE: PRT
<213> ORGANISM: Sus scrofa

<400> SEQUENCE: 18

Gly Gly Arg Leu Cys Tyr Cys Arg Arg Phe Cys Ile Cys Val Gly
1               5                   10                  15

<210> SEQ ID NO 19
<211> LENGTH: 51
<212> TYPE: PRT
<213> ORGANISM: Homo sapiens

<400> SEQUENCE: 19

Met Lys Phe Phe Val Phe Ala Leu Ile Leu Ala Leu Met Leu Ser Met
1               5                   10                  15

Thr Gly Ala Asp Ser His Ala Lys Arg His His Gly Tyr Lys Arg Lys
            20                  25                  30

Phe His Glu Lys His His Ser His Arg Gly Tyr Arg Ser Asn Tyr Leu
        35                  40                  45

Tyr Asp Asn
    50

<210> SEQ ID NO 20
<211> LENGTH: 38
<212> TYPE: PRT
<213> ORGANISM: Macaca fascicularis

<400> SEQUENCE: 20

Asp Ser His Glu Glu Arg His His Gly Arg His Gly His His Lys Tyr
1               5                   10                  15

Gly Arg Lys Phe His Glu Lys His His Ser His Arg Gly Tyr Arg Ser
            20                  25                  30

Asn Tyr Leu Tyr Asp Asn
        35

<210> SEQ ID NO 21
<211> LENGTH: 33
<212> TYPE: PRT
```

<213> ORGANISM: Phyllomedusa sauvagei

<400> SEQUENCE: 21

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Thr
            20                  25                  30

Gln

<210> SEQ ID NO 22
<211> LENGTH: 34
<212> TYPE: PRT
<213> ORGANISM: Phyllomedusa sauvagei

<400> SEQUENCE: 22

Ala Leu Trp Phe Thr Met Leu Lys Lys Leu Gly Thr Met Ala Leu His
1               5                   10                  15

Ala Gly Lys Ala Ala Leu Gly Ala Ala Ala Asn Thr Ile Ser Gln Gly
            20                  25                  30

Thr Gln

<210> SEQ ID NO 23
<211> LENGTH: 30
<212> TYPE: PRT
<213> ORGANISM: Phyllomedusa sauvagei

<400> SEQUENCE: 23

Ala Leu Trp Lys Asn Met Leu Lys Gly Ile Gly Lys Leu Ala Gly Lys
1               5                   10                  15

Ala Ala Leu Gly Ala Val Lys Lys Leu Val Gly Ala Glu Ser
            20                  25                  30

<210> SEQ ID NO 24
<211> LENGTH: 21
<212> TYPE: PRT
<213> ORGANISM: Misgurnus anguillicaudatus

<400> SEQUENCE: 24

Arg Gln Arg Val Glu Glu Leu Ser Lys Phe Ser Lys Lys Gly Ala Ala
1               5                   10                  15

Ala Arg Arg Arg Lys
            20

<210> SEQ ID NO 25
<211> LENGTH: 27
<212> TYPE: PRT
<213> ORGANISM: Apis mellifera

<400> SEQUENCE: 25

Gly Ile Gly Ala Val Leu Lys Val Leu Thr Thr Gly Leu Pro Ala Leu
1               5                   10                  15

Ile Ser Trp Ile Ser Arg Lys Lys Arg Gln Gln
            20                  25

<210> SEQ ID NO 26
<211> LENGTH: 33
<212> TYPE: PRT
<213> ORGANISM: Pardachirus pavoninus

<400> SEQUENCE: 26

Gly Phe Phe Ala Leu Ile Pro Lys Ile Ile Ser Ser Pro Leu Phe Lys
1               5                   10                  15

```
Thr Leu Leu Ser Ala Val Gly Ser Ala Leu Ser Ser Ser Gly Glu Gln
            20                  25                  30
Glu

<210> SEQ ID NO 27
<211> LENGTH: 33
<212> TYPE: PRT
<213> ORGANISM: Pardachirus pavoninus

<400> SEQUENCE: 27

Gly Phe Phe Ala Leu Ile Pro Lys Ile Ile Ser Ser Pro Ile Phe Lys
1               5                   10                  15

Thr Leu Leu Ser Ala Val Gly Ser Ala Leu Ser Ser Ser Gly Gly Gln
            20                  25                  30

Glu

<210> SEQ ID NO 28
<211> LENGTH: 176
<212> TYPE: PRT
<213> ORGANISM: Bos taurus

<400> SEQUENCE: 28

Met Glu Thr Gln Arg Ala Ser Leu Ser Leu Gly Arg Cys Ser Leu Trp
1               5                   10                  15

Leu Leu Leu Leu Gly Leu Val Leu Pro Ser Ala Ser Ala Gln Ala Leu
            20                  25                  30

Ser Tyr Arg Glu Ala Val Leu Arg Ala Val Asp Gln Phe Asn Glu Arg
        35                  40                  45

Ser Ser Glu Ala Asn Leu Tyr Arg Leu Leu Glu Leu Asp Pro Thr Pro
    50                  55                  60

Asn Asp Asp Leu Asp Pro Gly Thr Arg Lys Pro Val Ser Phe Arg Val
65                  70                  75                  80

Lys Glu Thr Asp Cys Pro Arg Thr Ser Gln Gln Pro Leu Glu Gln Cys
                85                  90                  95

Asp Phe Lys Glu Asn Gly Leu Val Lys Gln Cys Val Gly Thr Val Thr
            100                 105                 110

Leu Asp Pro Ser Asn Asp Gln Phe Asp Ile Asn Cys Asn Glu Leu Gln
        115                 120                 125

Ser Val Arg Phe Arg Pro Pro Ile Arg Arg Pro Pro Ile Arg Pro Pro
    130                 135                 140

Phe Tyr Pro Pro Phe Arg Pro Pro Ile Arg Pro Pro Ile Phe Pro Pro
145                 150                 155                 160

Ile Arg Pro Pro Phe Arg Pro Pro Leu Gly Pro Phe Pro Gly Arg Arg
                165                 170                 175

<210> SEQ ID NO 29
<211> LENGTH: 155
<212> TYPE: PRT
<213> ORGANISM: Bos taurus

<400> SEQUENCE: 29

Met Glu Thr Pro Arg Ala Ser Leu Ser Leu Gly Arg Trp Ser Leu Trp
1               5                   10                  15

Leu Leu Leu Leu Gly Leu Ala Leu Pro Ser Ala Ser Ala Gln Ala Leu
            20                  25                  30

Ser Tyr Arg Glu Ala Val Leu Arg Ala Val Asp Gln Leu Asn Glu Gln
        35                  40                  45
```

```
Ser Ser Glu Pro Asn Ile Tyr Arg Leu Leu Glu Leu Asp Gln Pro Pro
    50                  55                  60

Gln Asp Asp Glu Asp Pro Asp Ser Pro Lys Arg Val Ser Phe Arg Val
65                  70                  75                  80

Lys Glu Thr Val Cys Ser Arg Thr Thr Gln Gln Pro Pro Glu Gln Cys
                85                  90                  95

Asp Phe Lys Glu Asn Gly Leu Leu Lys Arg Cys Glu Gly Thr Val Thr
            100                 105                 110

Leu Asp Gln Val Arg Gly Asn Phe Asp Ile Thr Cys Asn Asn His Gln
        115                 120                 125

Ser Ile Arg Ile Thr Lys Gln Pro Trp Ala Pro Gln Ala Ala Arg
    130                 135                 140

Leu Cys Arg Ile Val Val Ile Arg Val Cys Arg
145                 150                 155

<210> SEQ ID NO 30
<211> LENGTH: 29
<212> TYPE: PRT
<213> ORGANISM: Ceratitis capitata

<400> SEQUENCE: 30

Ser Ile Gly Ser Ala Leu Lys Lys Ala Leu Pro Val Ala Lys Lys Ile
1               5                   10                  15

Gly Lys Ile Ala Leu Pro Ile Ala Lys Ala Ala Leu Pro
            20                  25

<210> SEQ ID NO 31
<211> LENGTH: 29
<212> TYPE: PRT
<213> ORGANISM: Ceratitis capitata

<400> SEQUENCE: 31

Ser Ile Gly Ser Ala Phe Lys Lys Ala Leu Pro Val Ala Lys Lys Ile
1               5                   10                  15

Gly Lys Ala Ala Leu Pro Ile Ala Lys Ala Ala Leu Pro
            20                  25

<210> SEQ ID NO 32
<211> LENGTH: 170
<212> TYPE: PRT
<213> ORGANISM: Homo sapiens

<400> SEQUENCE: 32

Met Lys Thr Gln Arg Asn Gly His Ser Leu Gly Arg Trp Ser Leu Val
1               5                   10                  15

Leu Leu Leu Leu Gly Leu Val Met Pro Leu Ala Ile Ile Ala Gln Val
            20                  25                  30

Leu Ser Tyr Lys Glu Ala Val Leu Arg Ala Ile Asp Gly Ile Asn Gln
        35                  40                  45

Arg Ser Ser Asp Ala Asn Leu Tyr Arg Leu Leu Asp Leu Asp Pro Arg
    50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125
```

```
Asn Lys Arg Phe Ala Leu Leu Gly Asp Phe Arg Lys Ser Lys Glu
        130                 135                 140
Lys Ile Gly Lys Glu Phe Lys Arg Ile Val Gln Arg Ile Lys Asp Phe
145                 150                 155                 160
Leu Arg Asn Leu Val Pro Arg Thr Glu Ser
                165                 170

<210> SEQ ID NO 33
<211> LENGTH: 170
<212> TYPE: PRT
<213> ORGANISM: Equus caballus

<400> SEQUENCE: 33

Met Glu Thr Gln Arg Asn Thr Arg Cys Leu Gly Arg Trp Ser Pro Leu
1               5                   10                  15
Leu Leu Leu Leu Gly Leu Val Ile Pro Pro Ala Thr Gln Ala Leu
                20                  25                  30
Ser Tyr Lys Glu Ala Val Leu Arg Ala Val Asp Gly Leu Asn Gln Arg
                35                  40                  45
Ser Ser Asp Glu Asn Leu Tyr Arg Leu Leu Glu Leu Asp Pro Leu Pro
            50                  55                  60
Lys Gly Asp Lys Asp Ser Asp Thr Pro Lys Pro Val Ser Phe Met Val
65                  70                  75                  80
Lys Glu Thr Val Cys Pro Arg Ile Met Lys Gln Thr Pro Glu Gln Cys
                        85                  90                  95
Asp Phe Lys Glu Asn Gly Leu Val Lys Gln Cys Val Gly Thr Val Ile
                100                 105                 110
Leu Asp Pro Val Lys Asp Tyr Phe Asp Ala Ser Cys Asp Glu Pro Gln
                115                 120                 125
Arg Val Lys Arg Phe His Ser Val Gly Ser Leu Ile Gln Arg His Gln
        130                 135                 140
Gln Met Ile Arg Asp Lys Ser Glu Ala Thr Arg His Gly Ile Arg Ile
145                 150                 155                 160
Ile Thr Arg Pro Lys Leu Leu Leu Ala Ser
                165                 170

<210> SEQ ID NO 34
<211> LENGTH: 159
<212> TYPE: PRT
<213> ORGANISM: Bos taurus

<400> SEQUENCE: 34

Met Glu Thr Gln Arg Ala Ser Leu Ser Leu Gly Arg Trp Ser Leu Trp
1               5                   10                  15
Leu Leu Leu Leu Gly Leu Ala Leu Pro Ser Ala Ser Ala Gln Ala Leu
                20                  25                  30
Ser Tyr Arg Glu Ala Val Leu Arg Ala Val Asp Gln Leu Asn Glu Lys
                35                  40                  45
Ser Ser Glu Ala Asn Leu Tyr Arg Leu Leu Glu Leu Asp Pro Pro Pro
            50                  55                  60
Lys Glu Asp Asp Glu Asn Pro Asn Ile Pro Lys Pro Val Ser Phe Arg
65                  70                  75                  80
Val Lys Glu Thr Val Cys Pro Arg Thr Ser Gln Gln Ser Pro Glu Gln
                    85                  90                  95
Cys Asp Phe Lys Glu Asn Gly Leu Leu Lys Glu Cys Val Gly Thr Val
                100                 105                 110
```

```
Thr Leu Asp Gln Val Gly Ser Asn Phe Asp Ile Thr Cys Ala Val Pro
        115                 120                 125

Gln Ser Val Gly Gly Leu Arg Ser Leu Gly Arg Lys Ile Leu Arg Ala
130                 135                 140

Trp Lys Lys Tyr Gly Pro Ile Ile Val Pro Ile Ile Arg Ile Gly
145                 150                 155

<210> SEQ ID NO 35
<211> LENGTH: 156
<212> TYPE: PRT
<213> ORGANISM: Equus caballus

<400> SEQUENCE: 35

Met Glu Thr Gln Arg Asn Thr Arg Cys Leu Gly Arg Trp Ser Pro Leu
1               5                   10                  15

Leu Leu Leu Leu Gly Leu Val Ile Pro Pro Ala Thr Gln Ala Leu
            20                  25                  30

Ser Tyr Lys Glu Ala Val Leu Arg Ala Val Asp Gly Leu Asn Gln Arg
        35                  40                  45

Ser Ser Asp Glu Asn Leu Tyr Arg Leu Leu Glu Leu Asp Pro Leu Pro
    50                  55                  60

Lys Gly Asp Lys Asp Ser Asp Thr Pro Lys Pro Val Ser Phe Met Val
65                  70                  75                  80

Lys Glu Thr Val Cys Pro Arg Ile Met Lys Gln Thr Pro Glu Gln Cys
                85                  90                  95

Asp Phe Lys Glu Asn Gly Leu Val Lys Gln Cys Val Gly Thr Val Ile
                100                 105                 110

Leu Gly Pro Val Lys Asp His Phe Asp Val Ser Cys Gly Glu Pro Gln
            115                 120                 125

Arg Val Lys Arg Phe Gly Arg Leu Ala Lys Ser Phe Leu Arg Met Arg
130                 135                 140

Ile Leu Leu Pro Arg Arg Lys Ile Leu Leu Ala Ser
145                 150                 155

<210> SEQ ID NO 36
<211> LENGTH: 160
<212> TYPE: PRT
<213> ORGANISM: Ovis aries

<400> SEQUENCE: 36

Met Glu Thr Gln Arg Ala Ser Leu Ser Leu Gly Arg Cys Ser Leu Trp
1               5                   10                  15

Leu Leu Leu Leu Gly Leu Ala Leu Pro Ser Ala Ser Ala Gln Val Leu
            20                  25                  30

Ser Tyr Arg Glu Ala Val Leu Arg Ala Ala Asp Gln Leu Asn Glu Lys
        35                  40                  45

Ser Ser Glu Ala Asn Leu Tyr Arg Leu Leu Glu Leu Asp Pro Pro Pro
    50                  55                  60

Lys Gln Asp Asp Glu Asn Ser Asn Ile Pro Lys Pro Val Ser Phe Arg
65                  70                  75                  80

Val Lys Glu Thr Val Cys Pro Arg Thr Ser Gln Gln Pro Ala Glu Gln
                85                  90                  95

Cys Asp Phe Lys Glu Asn Gly Leu Leu Lys Cys Val Gly Thr Val
                100                 105                 110

Thr Leu Asp Gln Val Arg Asn Asn Phe Asp Ile Thr Cys Ala Glu Pro
            115                 120                 125

Gln Ser Val Arg Gly Leu Arg Arg Leu Gly Arg Lys Ile Ala His Gly
```

```
                130                 135                 140
Val Lys Lys Tyr Gly Pro Thr Val Leu Arg Ile Ile Arg Ile Ala Gly
145                 150                 155                 160

<210> SEQ ID NO 37
<211> LENGTH: 12
<212> TYPE: PRT
<213> ORGANISM: Bos taurus

<400> SEQUENCE: 37

Arg Leu Cys Arg Ile Val Val Ile Arg Val Cys Arg
1               5                   10

<210> SEQ ID NO 38
<211> LENGTH: 30
<212> TYPE: PRT
<213> ORGANISM: Homo sapiens

<400> SEQUENCE: 38

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 39
<211> LENGTH: 29
<212> TYPE: PRT
<213> ORGANISM: Homo sapiens

<400> SEQUENCE: 39

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 40
<211> LENGTH: 30
<212> TYPE: PRT
<213> ORGANISM: Homo sapiens

<400> SEQUENCE: 40

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 41
<211> LENGTH: 33
<212> TYPE: PRT
<213> ORGANISM: Homo sapiens

<400> SEQUENCE: 41

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val

<210> SEQ ID NO 42
<211> LENGTH: 33
<212> TYPE: PRT
<213> ORGANISM: Oryctolagus cuniculus
```

-continued

```
<400> SEQUENCE: 42

Val Val Cys Ala Cys Arg Arg Ala Leu Cys Leu Pro Arg Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 43
<211> LENGTH: 33
<212> TYPE: PRT
<213> ORGANISM: Oryctolagus cuniculus

<400> SEQUENCE: 43

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 44
<211> LENGTH: 34
<212> TYPE: PRT
<213> ORGANISM: Oryctolagus cuniculus

<400> SEQUENCE: 44

Gly Ile Cys Ala Cys Arg Arg Arg Phe Cys Pro Asn Ser Glu Arg Phe
1               5                   10                  15

Ser Gly Tyr Cys Arg Val Asn Gly Ala Arg Tyr Val Arg Cys Cys Ser
            20                  25                  30

Arg Arg

<210> SEQ ID NO 45
<211> LENGTH: 34
<212> TYPE: PRT
<213> ORGANISM: Oryctolagus cuniculus

<400> SEQUENCE: 45

Gly Arg Cys Val Cys Arg Lys Gln Leu Leu Cys Ser Tyr Arg Glu Arg
1               5                   10                  15

Arg Ile Gly Asp Cys Lys Ile Arg Gly Val Arg Phe Pro Phe Cys Cys
            20                  25                  30

Pro Arg

<210> SEQ ID NO 46
<211> LENGTH: 34
<212> TYPE: PRT
<213> ORGANISM: Oryctolagus cuniculus

<400> SEQUENCE: 46

Val Ser Cys Thr Cys Arg Arg Phe Ser Cys Gly Phe Gly Glu Arg Ala
1               5                   10                  15

Ser Gly Ser Cys Thr Val Asn Gly Gly Val Arg His Thr Leu Cys Cys
            20                  25                  30

Arg Arg

<210> SEQ ID NO 47
<211> LENGTH: 33
<212> TYPE: PRT
<213> ORGANISM: Oryctolagus cuniculus
```

-continued

<400> SEQUENCE: 47

Val Phe Cys Thr Cys Arg Gly Phe Leu Cys Gly Ser Gly Glu Arg Ala
1               5                   10                  15

Ser Gly Ser Cys Thr Ile Asn Gly Val Arg His Thr Leu Cys Cys Arg
            20                  25                  30

Arg

<210> SEQ ID NO 48
<211> LENGTH: 32
<212> TYPE: PRT
<213> ORGANISM: Rattus norvegicus

<400> SEQUENCE: 48

Val Thr Cys Tyr Cys Arg Arg Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30

<210> SEQ ID NO 49
<211> LENGTH: 30
<212> TYPE: PRT
<213> ORGANISM: Rattus norvegicus

<400> SEQUENCE: 49

Cys Ser Cys Arg Tyr Ser Ser Cys Arg Phe Gly Glu Arg Leu Leu Ser
1               5                   10                  15

Gly Ala Cys Arg Leu Asn Gly Arg Ile Tyr Arg Leu Cys Cys
            20                  25                  30

<210> SEQ ID NO 50
<211> LENGTH: 31
<212> TYPE: PRT
<213> ORGANISM: Rattus norvegicus

<400> SEQUENCE: 50

Ala Cys Thr Cys Arg Ile Gly Ala Cys Val Ser Gly Glu Arg Leu Thr
1               5                   10                  15

Gly Ala Cys Gly Leu Asn Gly Arg Ile Tyr Arg Leu Cys Cys Arg
            20                  25                  30

<210> SEQ ID NO 51
<211> LENGTH: 31
<212> TYPE: PRT
<213> ORGANISM: Guinea pig

<400> SEQUENCE: 51

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30

<210> SEQ ID NO 52
<211> LENGTH: 67
<212> TYPE: PRT
<213> ORGANISM: Homo sapiens

<400> SEQUENCE: 52

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

```
Cys Arg Val Arg Gly Gly Arg Cys Ala Val Leu Ser Cys Leu Pro Lys
            35                  40                  45

Glu Glu Gln Ile Gly Lys Cys Ser Thr Arg Gly Arg Lys Cys Cys Arg
 50                  55                  60

Arg Lys Lys
 65

<210> SEQ ID NO 53
<211> LENGTH: 18
<212> TYPE: PRT
<213> ORGANISM: Macaca mulatta

<400> SEQUENCE: 53

Arg Cys Ile Cys Thr Arg Gly Phe Cys Arg Cys Leu Cys Arg Arg Gly
 1               5                  10                  15

Val Cys

<210> SEQ ID NO 54
<211> LENGTH: 78
<212> TYPE: PRT
<213> ORGANISM: Helianthus annuus

<400> SEQUENCE: 54

Met Lys Ser Ser Met Lys Met Phe Ala Ala Leu Leu Leu Val Val Met
 1               5                  10                  15

Cys Leu Leu Ala Asn Glu Met Gly Gly Pro Leu Val Val Glu Ala Arg
            20                  25                  30

Thr Cys Glu Ser Gln Ser His Lys Phe Lys Gly Thr Cys Leu Ser Asp
            35                  40                  45

Thr Asn Cys Ala Asn Val Cys His Ser Glu Arg Phe Ser Gly Gly Lys
 50                  55                  60

Cys Arg Gly Phe Arg Arg Arg Cys Phe Cys Thr Thr His Cys
 65                  70                  75

<210> SEQ ID NO 55
<211> LENGTH: 78
<212> TYPE: PRT
<213> ORGANISM: Helianthus annuus

<400> SEQUENCE: 55

Met Lys Ser Ser Met Lys Met Phe Ala Ala Leu Leu Leu Val Val Met
 1               5                  10                  15

Cys Leu Leu Ala Asn Glu Met Gly Gly Pro Leu Val Val Glu Ala Arg
            20                  25                  30

Thr Cys Glu Ser Gln Ser His Lys Phe Lys Gly Thr Cys Leu Ser Asp
            35                  40                  45

Thr Asn Cys Ala Asn Val Cys His Ser Glu Arg Phe Ser Gly Gly Lys
 50                  55                  60

Cys Arg Gly Phe Arg Arg Arg Cys Phe Cys Thr Thr His Cys
 65                  70                  75

<210> SEQ ID NO 56
<211> LENGTH: 30
<212> TYPE: PRT
<213> ORGANISM: Macaca mulatta

<400> SEQUENCE: 56

Ala Cys Tyr Cys Arg Ile Pro Ala Cys Leu Ala Gly Glu Arg Arg Tyr
 1               5                  10                  15

Gly Thr Cys Phe Tyr Met Gly Arg Val Trp Ala Phe Cys Cys
```

```
<210> SEQ ID NO 57
<211> LENGTH: 37
<212> TYPE: PRT
<213> ORGANISM: Androctonus australis hector

<400> SEQUENCE: 57

Gly Phe Gly Cys Pro Phe Asn Gln Gly Ala Cys His Arg His Cys Arg
1               5                   10                  15

Ser Ile Arg Arg Arg Gly Gly Tyr Cys Ala Gly Leu Phe Lys Gln Thr
            20                  25                  30

Cys Thr Cys Tyr Arg
        35

<210> SEQ ID NO 58
<211> LENGTH: 38
<212> TYPE: PRT
<213> ORGANISM: Mytilus galloprovincialis
<220> FEATURE:
<221> NAME/KEY: misc_feature
<222> LOCATION: (28)..(28)
<223> OTHER INFORMATION: Xaa can be any naturally occurring amino acid

<400> SEQUENCE: 58

Gly Phe Gly Cys Pro Asn Asn Tyr Gln Cys His Arg His Cys Lys Ser
1               5                   10                  15

Ile Pro Gly Arg Cys Gly Gly Tyr Cys Gly Gly Xaa His Arg Leu Arg
            20                  25                  30

Cys Thr Cys Tyr Arg Cys
        35

<210> SEQ ID NO 59
<211> LENGTH: 54
<212> TYPE: PRT
<213> ORGANISM: Heuchera sanguinea

<400> SEQUENCE: 59

Asp Gly Val Lys Leu Cys Asp Val Pro Ser Gly Thr Trp Ser Gly His
1               5                   10                  15

Cys Gly Ser Ser Ser Lys Cys Ser Gln Gln Cys Lys Asp Arg Glu His
            20                  25                  30

Phe Ala Tyr Gly Gly Ala Cys His Tyr Gln Phe Pro Ser Val Lys Cys
        35                  40                  45

Phe Cys Lys Arg Gln Cys
    50

<210> SEQ ID NO 60
<211> LENGTH: 49
<212> TYPE: PRT
<213> ORGANISM: Clitoria ternatea

<400> SEQUENCE: 60

Asn Leu Cys Glu Arg Ala Ser Leu Thr Trp Thr Gly Asn Cys Gly Asn
1               5                   10                  15

Thr Gly His Cys Asp Thr Gln Cys Arg Asn Trp Glu Ser Ala Lys His
            20                  25                  30

Gly Ala Cys His Lys Arg Gly Asn Trp Lys Cys Phe Cys Tyr Phe Asn
        35                  40                  45

Cys
```

```
<210> SEQ ID NO 61
<211> LENGTH: 91
<212> TYPE: PRT
<213> ORGANISM: Mus musculus

<400> SEQUENCE: 61

Met Lys Lys Leu Val Leu Leu Phe Ala Leu Val Leu Leu Ala Phe Gln
1               5                   10                  15

Val Gln Ala Asp Ser Ile Gln Asn Thr Asp Glu Glu Thr Lys Thr Glu
            20                  25                  30

Glu Gln Pro Gly Glu Lys Asp Gln Ala Val Ser Val Ser Phe Gly Asp
        35                  40                  45

Pro Gln Gly Ser Ala Leu Gln Asp Ala Ala Leu Gly Trp Gly Arg Arg
    50                  55                  60

Cys Pro Gln Cys Pro Arg Cys Pro Ser Cys Pro Ser Cys Pro Arg Cys
65                  70                  75                  80

Pro Arg Cys Pro Arg Cys Lys Cys Asn Pro Lys
                85                  90

<210> SEQ ID NO 62
<211> LENGTH: 40
<212> TYPE: PRT
<213> ORGANISM: Bos taurus

<400> SEQUENCE: 62

Gln Gly Val Arg Asn Phe Val Thr Cys Arg Ile Asn Arg Gly Phe Cys
1               5                   10                  15

Val Pro Ile Arg Cys Pro Gly His Arg Arg Gln Ile Gly Thr Cys Leu
            20                  25                  30

Gly Pro Gln Ile Lys Cys Cys Arg
        35                  40

<210> SEQ ID NO 63
<211> LENGTH: 40
<212> TYPE: PRT
<213> ORGANISM: Bos taurus

<400> SEQUENCE: 63

Gln Gly Val Arg Asn Phe Val Thr Cys Arg Ile Asn Arg Gly Phe Cys
1               5                   10                  15

Val Pro Ile Arg Cys Pro Gly His Arg Arg Gln Ile Gly Thr Cys Leu
            20                  25                  30

Gly Pro Arg Ile Lys Cys Cys Arg
        35                  40

<210> SEQ ID NO 64
<211> LENGTH: 42
<212> TYPE: PRT
<213> ORGANISM: Bos taurus

<400> SEQUENCE: 64

Gln Gly Val Arg Asn His Val Thr Cys Arg Ile Tyr Gly Gly Phe Cys
1               5                   10                  15

Val Pro Ile Arg Cys Pro Gly Arg Thr Arg Gln Ile Gly Thr Cys Phe
            20                  25                  30

Gly Arg Pro Val Lys Cys Cys Arg Arg Trp
        35                  40

<210> SEQ ID NO 65
<211> LENGTH: 40
<212> TYPE: PRT
```

<213> ORGANISM: Bos taurus

<400> SEQUENCE: 65

Gln Val Val Arg Asn Pro Gln Ser Cys Arg Trp Asn Met Gly Val Cys
1               5                   10                  15

Ile Pro Ile Ser Cys Pro Gly Asn Met Arg Gln Ile Gly Thr Cys Phe
            20                  25                  30

Gly Pro Arg Val Pro Cys Cys Arg
        35                  40

<210> SEQ ID NO 66
<211> LENGTH: 41
<212> TYPE: PRT
<213> ORGANISM: Bos taurus

<400> SEQUENCE: 66

Gln Arg Val Arg Asn Pro Gln Ser Cys Arg Trp Asn Met Gly Val Cys
1               5                   10                  15

Ile Pro Phe Leu Cys Arg Val Gly Met Arg Gln Ile Gly Thr Cys Phe
            20                  25                  30

Gly Pro Arg Val Pro Cys Cys Arg Arg
        35                  40

<210> SEQ ID NO 67
<211> LENGTH: 42
<212> TYPE: PRT
<213> ORGANISM: Bos taurus

<400> SEQUENCE: 67

Gln Gly Val Arg Asn His Val Thr Cys Arg Ile Asn Arg Gly Phe Cys
1               5                   10                  15

Val Pro Ile Arg Cys Pro Gly Arg Thr Arg Gln Ile Gly Thr Cys Phe
            20                  25                  30

Gly Pro Arg Ile Lys Cys Cys Arg Ser Trp
        35                  40

<210> SEQ ID NO 68
<211> LENGTH: 40
<212> TYPE: PRT
<213> ORGANISM: Bos taurus

<400> SEQUENCE: 68

Gln Gly Val Arg Ser Tyr Leu Ser Cys Trp Gly Asn Arg Gly Ile Cys
1               5                   10                  15

Leu Leu Asn Arg Cys Pro Gly Arg Met Arg Gln Ile Gly Thr Cys Leu
            20                  25                  30

Ala Pro Arg Val Lys Cys Cys Arg
        35                  40

<210> SEQ ID NO 69
<211> LENGTH: 42
<212> TYPE: PRT
<213> ORGANISM: Bos taurus

<400> SEQUENCE: 69

Ser Gly Ile Ser Gly Pro Leu Ser Cys Gly Arg Asn Gly Gly Val Cys
1               5                   10                  15

Ile Pro Ile Arg Cys Pro Val Pro Met Arg Gln Ile Gly Thr Cys Phe
            20                  25                  30

Gly Arg Pro Val Lys Cys Cys Arg Ser Trp
        35                  40

<210> SEQ ID NO 70
<211> LENGTH: 38
<212> TYPE: PRT
<213> ORGANISM: Bos taurus

<400> SEQUENCE: 70

Asp Phe Ala Ser Cys His Thr Asn Gly Gly Ile Cys Leu Pro Asn Arg
1               5                   10                  15

Cys Pro Gly His Met Ile Gln Ile Gly Ile Cys Phe Arg Pro Arg Val
            20                  25                  30

Lys Cys Cys Arg Ser Trp
        35

<210> SEQ ID NO 71
<211> LENGTH: 74
<212> TYPE: PRT
<213> ORGANISM: Zophobas atratus

<400> SEQUENCE: 71

Ser Leu Gln Gly Gly Ala Pro Asn Phe Pro Gln Pro Ser Gln Gln Asn
1               5                   10                  15

Gly Gly Trp Gln Val Ser Pro Asp Leu Gly Arg Asp Asp Lys Gly Asn
            20                  25                  30

Thr Arg Gly Gln Ile Glu Ile Gln Asn Lys Gly Lys Asp His Asp Phe
        35                  40                  45

Asn Ala Gly Trp Gly Lys Val Ile Arg Gly Pro Asn Lys Ala Lys Pro
    50                  55                  60

Thr Trp His Val Gly Gly Thr Tyr Arg Arg
65                  70

<210> SEQ ID NO 72
<211> LENGTH: 67
<212> TYPE: PRT
<213> ORGANISM: Homo sapiens

<400> SEQUENCE: 72

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65

<210> SEQ ID NO 73
<211> LENGTH: 40
<212> TYPE: PRT
<213> ORGANISM: Aedes aegypti

<400> SEQUENCE: 73

Ala Thr Cys Asp Leu Leu Ser Gly Phe Gly Val Gly Asp Ser Ala Cys
1               5                   10                  15

Ala Ala His Cys Ile Ala Arg Gly Asn Arg Gly Gly Tyr Cys Asn Ser
            20                  25                  30

Lys Lys Val Cys Val Cys Arg Asn
        35                  40

<210> SEQ ID NO 74
<211> LENGTH: 35
<212> TYPE: PRT
<213> ORGANISM: Mytilus edulis
<220> FEATURE:
<221> NAME/KEY: misc_feature
<222> LOCATION: (28)..(28)
<223> OTHER INFORMATION: Xaa can be any naturally occurring amino acid

<400> SEQUENCE: 74

Gly Phe Gly Cys Pro Asn Asp Tyr Pro Cys His Arg His Cys Lys Ser
1               5                   10                  15

Ile Pro Gly Arg Tyr Gly Gly Tyr Cys Gly Gly Xaa His Arg Leu Arg
            20                  25                  30

Cys Thr Cys
        35

<210> SEQ ID NO 75
<211> LENGTH: 40
<212> TYPE: PRT
<213> ORGANISM: Sarcophaga peregrina

<400> SEQUENCE: 75

Ala Thr Cys Asp Leu Leu Ser Gly Ile Gly Val Gln His Ser Ala Cys
1               5                   10                  15

Ala Leu His Cys Val Phe Arg Gly Asn Arg Gly Gly Tyr Cys Thr Gly
            20                  25                  30

Lys Gly Ile Cys Val Cys Arg Asn
        35                  40

<210> SEQ ID NO 76
<211> LENGTH: 95
<212> TYPE: PRT
<213> ORGANISM: Oryctolagus cuniculus

<400> SEQUENCE: 76

Met Arg Thr Leu Ala Leu Leu Ala Ala Ile Leu Leu Val Ala Leu Gln
1               5                   10                  15

Ala Gln Ala Glu His Val Ser Val Ser Ile Asp Glu Val Val Asp Gln
            20                  25                  30

Gln Pro Pro Gln Ala Glu Asp Gln Asp Val Ala Ile Tyr Val Lys Glu
        35                  40                  45

His Glu Ser Ser Ala Leu Glu Ala Leu Gly Val Lys Ala Gly Val Val
    50                  55                  60

Cys Ala Cys Arg Arg Ala Leu Cys Leu Pro Arg Glu Arg Arg Ala Gly
65                  70                  75                  80

Phe Cys Arg Ile Arg Gly Arg Ile His Pro Leu Cys Cys Arg Arg
                85                  90                  95

<210> SEQ ID NO 77
<211> LENGTH: 92
<212> TYPE: PRT
<213> ORGANISM: Mus musculus

<400> SEQUENCE: 77

Met Lys Pro Leu Val Leu Leu Ser Ala Leu Val Leu Leu Ser Phe Gln
1               5                   10                  15

Val Gln Ala Asp Pro Ile Gln Asn Thr Asp Glu Glu Thr Lys Thr Glu
            20                  25                  30

Glu Gln Ser Gly Glu Glu Asp Gln Ala Val Ser Val Ser Phe Gly Asp

```
                35                  40                  45
Arg Glu Gly Ala Ser Leu Gln Glu Ser Leu Arg Asp Leu Val Cys
 50                  55                  60

Tyr Cys Arg Thr Arg Gly Cys Lys Arg Glu Arg Met Asn Gly Thr
 65                  70                  75                  80

Cys Arg Lys Gly His Leu Met Tyr Thr Leu Cys Cys
                 85                  90

<210> SEQ ID NO 78
<211> LENGTH: 93
<212> TYPE: PRT
<213> ORGANISM: Mus musculus

<400> SEQUENCE: 78

Met Lys Thr Phe Val Leu Leu Ser Ala Leu Val Leu Ala Phe Gln
  1               5                  10                  15

Val Gln Ala Asp Pro Ile His Lys Thr Asp Glu Glu Thr Asn Thr Glu
                 20                  25                  30

Glu Gln Pro Gly Glu Glu Asp Gln Ala Val Ser Ile Ser Phe Gly Gly
                 35                  40                  45

Gln Glu Gly Ser Ala Leu His Glu Glu Leu Ser Lys Lys Leu Ile Cys
 50                  55                  60

Tyr Cys Arg Ile Arg Gly Cys Lys Arg Arg Glu Arg Val Phe Gly Thr
 65                  70                  75                  80

Cys Arg Asn Leu Phe Leu Thr Phe Val Phe Cys Cys Ser
                 85                  90

<210> SEQ ID NO 79
<211> LENGTH: 35
<212> TYPE: PRT
<213> ORGANISM: Mus musculus

<400> SEQUENCE: 79

Leu Arg Asp Leu Val Cys Tyr Cys Arg Ala Arg Gly Cys Lys Gly Arg
  1               5                  10                  15

Glu Arg Met Asn Gly Thr Cys Arg Lys Gly His Leu Leu Tyr Met Leu
                 20                  25                  30

Cys Cys Arg
        35

<210> SEQ ID NO 80
<211> LENGTH: 43
<212> TYPE: PRT
<213> ORGANISM: Pyrrhocoris apterus

<400> SEQUENCE: 80

Ala Thr Cys Asp Ile Leu Ser Phe Gln Ser Gln Trp Val Thr Pro Asn
  1               5                  10                  15

His Ala Gly Cys Ala Leu His Cys Val Ile Lys Gly Tyr Lys Gly Gly
                 20                  25                  30

Gln Cys Lys Ile Thr Val Cys His Cys Arg Arg
        35                  40

<210> SEQ ID NO 81
<211> LENGTH: 32
<212> TYPE: PRT
<213> ORGANISM: Rattus norvegicus

<400> SEQUENCE: 81

Val Thr Cys Tyr Cys Arg Ser Thr Arg Cys Gly Phe Arg Glu Arg Leu
```

```
                 1               5                  10                 15
Ser Gly Ala Cys Gly Tyr Arg Gly Arg Ile Tyr Arg Leu Cys Cys Arg
                20                 25                 30

<210> SEQ ID NO 82
<211> LENGTH: 31
<212> TYPE: PRT
<213> ORGANISM: Rattus norvegicus

<400> SEQUENCE: 82

Val Thr Cys Ser Cys Arg Thr Ser Ser Cys Arg Phe Gly Glu Arg Leu
1               5                  10                 15

Ser Gly Ala Cys Arg Leu Asn Gly Arg Ile Tyr Arg Leu Cys Cys
                20                 25                 30

<210> SEQ ID NO 83
<211> LENGTH: 34
<212> TYPE: PRT
<213> ORGANISM: Oryctolagus cuniculus

<400> SEQUENCE: 83

Gly Ile Cys Ala Cys Arg Arg Arg Phe Cys Leu Asn Phe Glu Gln Phe
1               5                  10                 15

Ser Gly Tyr Cys Arg Val Asn Gly Ala Arg Tyr Val Arg Cys Cys Ser
                20                 25                 30

Arg Arg

<210> SEQ ID NO 84
<211> LENGTH: 64
<212> TYPE: PRT
<213> ORGANISM: Pan troglodytes

<400> SEQUENCE: 84

Met Arg Val Leu Tyr Leu Leu Phe Ser Phe Leu Phe Ile Phe Leu Met
1               5                  10                 15

Pro Leu Pro Gly Val Phe Gly Gly Ile Ser Asp Pro Val Thr Cys Leu
                20                 25                 30

Lys Ser Gly Ala Ile Cys His Pro Val Phe Cys Pro Arg Arg Tyr Lys
                35                 40                 45

Gln Ile Gly Thr Cys Gly Leu Pro Gly Thr Lys Cys Cys Lys Lys Pro
                50                 55                 60

<210> SEQ ID NO 85
<211> LENGTH: 64
<212> TYPE: PRT
<213> ORGANISM: Homo sapiens

<400> SEQUENCE: 85

Met Arg Val Leu Tyr Leu Leu Phe Ser Phe Leu Phe Ile Phe Leu Met
1               5                  10                 15

Pro Leu Pro Gly Val Phe Gly Gly Ile Gly Asp Pro Val Thr Cys Leu
                20                 25                 30

Lys Ser Gly Ala Ile Cys His Pro Val Phe Cys Pro Arg Arg Tyr Lys
                35                 40                 45

Gln Ile Gly Thr Cys Gly Leu Pro Gly Thr Lys Cys Cys Lys Lys Pro
                50                 55                 60

<210> SEQ ID NO 86
<211> LENGTH: 68
<212> TYPE: PRT
<213> ORGANISM: Homo sapiens
```

```
<400> SEQUENCE: 86

Met Arg Thr Ser Tyr Leu Leu Leu Phe Thr Leu Cys Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65

<210> SEQ ID NO 87
<211> LENGTH: 64
<212> TYPE: PRT
<213> ORGANISM: Capra hircus

<400> SEQUENCE: 87

Met Arg Leu His His Leu Leu Leu Val Leu Phe Phe Leu Val Leu Ser
1               5                   10                  15

Ala Gly Ser Gly Phe Thr Gln Gly Ile Arg Ser Arg Ser Cys His
            20                  25                  30

Arg Asn Lys Gly Val Cys Ala Leu Thr Arg Cys Pro Arg Asn Met Arg
        35                  40                  45

Gln Ile Gly Thr Cys Phe Gly Pro Pro Val Lys Cys Cys Arg Lys Lys
    50                  55                  60

<210> SEQ ID NO 88
<211> LENGTH: 64
<212> TYPE: PRT
<213> ORGANISM: Capra hircus

<400> SEQUENCE: 88

Met Arg Leu His His Leu Leu Leu Ala Leu Phe Phe Leu Val Leu Ser
1               5                   10                  15

Ala Gly Ser Gly Phe Thr Gln Gly Ile Ile Asn His Arg Ser Cys Tyr
            20                  25                  30

Arg Asn Lys Gly Val Cys Ala Pro Ala Arg Cys Pro Arg Asn Met Arg
        35                  40                  45

Gln Ile Gly Thr Cys His Gly Pro Pro Val Lys Cys Cys Arg Lys Lys
    50                  55                  60

<210> SEQ ID NO 89
<211> LENGTH: 96
<212> TYPE: PRT
<213> ORGANISM: Macaca mulatta

<400> SEQUENCE: 89

Met Arg Thr Leu Val Ile Leu Ala Ala Ile Leu Leu Val Ala Leu Gln
1               5                   10                  15

Ala Gln Ala Glu Pro Leu Gln Ala Arg Thr Asp Glu Ala Thr Ala Ala
            20                  25                  30

Gln Glu Gln Ile Pro Thr Asp Asn Pro Glu Val Val Ser Leu Ala
        35                  40                  45

Trp Asp Glu Ser Leu Ala Pro Lys Asp Ser Val Pro Gly Leu Arg Lys
    50                  55                  60

Asn Met Ala Cys Tyr Cys Arg Ile Pro Ala Cys Leu Ala Gly Glu Arg
65                  70                  75                  80
```

```
Arg Tyr Gly Thr Cys Phe Tyr Arg Arg Val Trp Ala Phe Cys Cys
                85                  90                  95
```

<210> SEQ ID NO 90
<211> LENGTH: 96
<212> TYPE: PRT
<213> ORGANISM: Macaca mulatta

<400> SEQUENCE: 90

```
Met Arg Thr Leu Val Ile Leu Ala Ala Ile Leu Leu Val Ala Leu Gln
 1               5                  10                  15

Ala Gln Ala Glu Pro Leu Gln Ala Arg Thr Asp Glu Ala Thr Ala Ala
            20                  25                  30

Gln Glu Gln Ile Pro Thr Asp Asn Pro Glu Val Val Val Ser Leu Ala
        35                  40                  45

Trp Asp Glu Ser Leu Ala Pro Lys Asp Ser Val Pro Gly Leu Arg Lys
    50                  55                  60

Asn Met Ala Cys Tyr Cys Arg Ile Pro Ala Cys Leu Ala Gly Glu Arg
65                  70                  75                  80

Arg Tyr Gly Thr Cys Phe Tyr Leu Gly Arg Val Trp Ala Phe Cys Cys
                85                  90                  95
```

<210> SEQ ID NO 91
<211> LENGTH: 33
<212> TYPE: PRT
<213> ORGANISM: Mesocricetus auratus

<400> SEQUENCE: 91

```
Val Thr Cys Phe Cys Arg Arg Arg Gly Cys Ala Ser Arg Glu Arg His
 1               5                  10                  15

Ile Gly Tyr Cys Arg Phe Gly Asn Thr Ile Tyr Arg Leu Cys Cys Arg
            20                  25                  30

Arg
```

<210> SEQ ID NO 92
<211> LENGTH: 31
<212> TYPE: PRT
<213> ORGANISM: Mesocricetus auratus

<400> SEQUENCE: 92

```
Cys Phe Cys Lys Arg Pro Val Cys Asp Ser Gly Glu Thr Gln Ile Gly
 1               5                  10                  15

Tyr Cys Arg Leu Gly Asn Thr Phe Tyr Arg Leu Cys Cys Arg Gln
            20                  25                  30
```

<210> SEQ ID NO 93
<211> LENGTH: 39
<212> TYPE: PRT
<213> ORGANISM: Gallus gallus

<400> SEQUENCE: 93

```
Gly Arg Lys Ser Asp Cys Phe Arg Lys Asn Gly Phe Cys Ala Phe Leu
 1               5                  10                  15

Lys Cys Pro Tyr Leu Thr Leu Ile Ser Gly Lys Cys Ser Arg Phe His
            20                  25                  30

Leu Cys Cys Lys Arg Ile Trp
        35
```

<210> SEQ ID NO 94
<211> LENGTH: 43

-continued

```
<212> TYPE: PRT
<213> ORGANISM: Allomyrina dichotoma

<400> SEQUENCE: 94

Val Thr Cys Asp Leu Leu Ser Phe Glu Ala Lys Gly Phe Ala Ala Asn
1               5                   10                  15

His Ser Leu Cys Ala Ala His Cys Leu Ala Ile Gly Arg Arg Gly Gly
                20                  25                  30

Ser Cys Glu Arg Gly Val Cys Ile Cys Arg Arg
        35                  40

<210> SEQ ID NO 95
<211> LENGTH: 31
<212> TYPE: PRT
<213> ORGANISM: Cavia porcellus

<400> SEQUENCE: 95

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
                20                  25                  30
```